United States Patent
Helekar et al.

(10) Patent No.: US 11,571,585 B2
(45) Date of Patent: Feb. 7, 2023

(54) METHOD AND APPARATUS FOR ONCOMAGNETIC TREATMENT

(71) Applicant: THE METHODIST HOSPITAL, Houston, TX (US)

(72) Inventors: Santosh Anand Helekar, Sugar Land, TX (US); David Stuart Baskin, Houston, TX (US); Martyn Alun Sharpe, Houston, TX (US); Kumar Pichumani, Sugar Land, TX (US)

(73) Assignee: THE METHODIST HOSPITAL, Houston, TX (US)

( * ) Notice: Subject to any disclaimer, the term of this patent is extended or adjusted under 35 U.S.C. 154(b) by 0 days.

(21) Appl. No.: 17/567,101

(22) Filed: Dec. 31, 2021

(65) Prior Publication Data

US 2022/0193436 A1   Jun. 23, 2022

Related U.S. Application Data

(63) Continuation of application No. PCT/US2021/038052, filed on Jun. 18, 2021.

(60) Provisional application No. 63/201,681, filed on May 7, 2021, provisional application No. 63/041,658, filed on Jun. 19, 2020.

(51) Int. Cl.
*A61N 2/00* (2006.01)
*A61N 2/06* (2006.01)
*A61N 2/12* (2006.01)

(52) U.S. Cl.
CPC ............... *A61N 2/004* (2013.01); *A61N 2/06* (2013.01); *A61N 2/12* (2013.01)

(58) Field of Classification Search
CPC ... A61N 2/00; A61N 2/02; A61N 2/06; A61N 2/002; A61N 2/004; A61N 2/006; A61N 2/008; A61N 2/12
See application file for complete search history.

(56) References Cited

U.S. PATENT DOCUMENTS

| | | |
|---|---|---|
| 4,537,198 A | 8/1985 | Corbett |
| 4,967,038 A | 10/1990 | Gevins |
| 6,032,677 A | 3/2000 | Blechman et al. |
| 6,046,046 A | 4/2000 | Hassanein |
| 6,100,082 A | 8/2000 | Hassanein |

(Continued)

FOREIGN PATENT DOCUMENTS

| | | |
|---|---|---|
| CN | 2796743 Y | 7/2006 |
| CN | 201216819 Y | 4/2009 |

(Continued)

OTHER PUBLICATIONS

Aleman, A., Use of Repetitive Transcranial Magnetic Stimulation for Treatment in Psychiatry, Clinical Psychopharmacology and Neuroscience, 2013, vol. 11, No. 2, pp. 53-59.

(Continued)

*Primary Examiner* — Samuel G Gilbert
(74) *Attorney, Agent, or Firm* — Marshall, Gerstein & Borun LLP

(57) ABSTRACT

The disclosure provides methods of cancer treatment and apparatus and, more particularly, to non-invasive cancer treatments utilizing oscillating magnetic fields to disrupt mitochondrial function or induce apoptosis or another mechanism of cell death in cancer cells. The disclosure also provides a device for providing an OMF treatment to a subject.

20 Claims, 42 Drawing Sheets

(56) References Cited

U.S. PATENT DOCUMENTS

| | | | |
|---|---|---|---|
| 6,123,657 A | 9/2000 | Ishikawa et al. | |
| 6,443,883 B1 * | 9/2002 | Ostrow | A61N 2/008 600/14 |
| 6,447,449 B1 | 9/2002 | Fleischman et al. | |
| 6,488,617 B1 | 12/2002 | Katz | |
| 6,673,623 B1 | 1/2004 | Huberman | |
| 6,868,289 B2 | 3/2005 | Palti | |
| 6,953,655 B1 | 10/2005 | Hassanein et al. | |
| 7,013,177 B1 | 3/2006 | Whitehurst | |
| 7,016,725 B2 | 3/2006 | Palti | |
| 7,089,054 B2 | 8/2006 | Palti | |
| 7,136,699 B2 | 11/2006 | Palti | |
| 7,146,210 B2 | 12/2006 | Palti | |
| 7,333,852 B2 | 2/2008 | Palti | |
| 7,467,011 B2 | 12/2008 | Palti | |
| 7,519,420 B2 | 4/2009 | Palti | |
| 7,565,205 B2 | 7/2009 | Palti | |
| 7,565,206 B2 | 7/2009 | Palti | |
| 7,572,622 B2 | 8/2009 | Hassanein et al. | |
| 7,599,745 B2 | 10/2009 | Palti | |
| 7,599,746 B2 | 10/2009 | Palti | |
| 7,651,835 B2 | 1/2010 | Hassanein et al. | |
| 7,706,890 B2 | 4/2010 | Palti | |
| 7,715,921 B2 | 5/2010 | Palti | |
| 7,805,201 B2 | 9/2010 | Palti | |
| 7,890,183 B2 | 2/2011 | Palti et al. | |
| 7,912,540 B2 | 3/2011 | Palti | |
| 7,917,227 B2 | 3/2011 | Palti | |
| 8,019,414 B2 | 9/2011 | Palti | |
| 8,027,738 B2 | 9/2011 | Palti | |
| 8,170,684 B2 | 5/2012 | Palti | |
| 8,175,698 B2 | 5/2012 | Palti et al. | |
| 8,229,555 B2 | 7/2012 | Palti | |
| RE43,618 E | 8/2012 | Palti | |
| 8,244,345 B2 | 8/2012 | Palti | |
| 8,304,181 B2 | 11/2012 | Hassanein et al. | |
| 8,406,870 B2 | 3/2013 | Palti | |
| 8,409,846 B2 | 4/2013 | Hassanein et al. | |
| 8,420,380 B2 | 4/2013 | Fishman et al. | |
| 8,447,395 B2 | 5/2013 | Palti et al. | |
| 8,447,396 B2 | 5/2013 | Palti et al. | |
| 8,465,533 B2 | 6/2013 | Palti | |
| 8,465,970 B2 | 6/2013 | Hassanein et al. | |
| 8,535,934 B2 | 9/2013 | Hassanein et al. | |
| 8,560,073 B2 | 10/2013 | Osorio | |
| 8,585,380 B2 | 11/2013 | Hassanein et al. | |
| 8,706,261 B2 | 4/2014 | Palti | |
| 8,715,203 B2 | 5/2014 | Palti | |
| 8,718,756 B2 | 5/2014 | Palti | |
| 8,764,675 B2 | 7/2014 | Palti | |
| 8,822,203 B2 | 9/2014 | Hassanein et al. | |
| 8,888,672 B2 | 11/2014 | Phillips et al. | |
| 9,023,090 B2 | 5/2015 | Palti | |
| 9,023,091 B2 | 5/2015 | Palti | |
| 9,039,674 B2 | 5/2015 | Palti et al. | |
| 9,055,740 B2 | 6/2015 | Hassanein et al. | |
| 9,056,203 B2 | 6/2015 | Palti et al. | |
| 9,078,428 B2 | 7/2015 | Hassanein et al. | |
| 9,215,867 B2 | 12/2015 | Hassanein et al. | |
| 9,247,728 B2 | 2/2016 | Fishman et al. | |
| 9,272,159 B2 | 3/2016 | Phillips et al. | |
| 9,301,519 B2 | 4/2016 | Hassanein et al. | |
| 9,440,068 B2 | 9/2016 | Palti et al. | |
| 9,456,784 B2 | 10/2016 | Helekar et al. | |
| 9,457,179 B2 | 10/2016 | Hassanein et al. | |
| 9,462,802 B2 | 10/2016 | Fishman et al. | |
| 9,516,875 B2 | 12/2016 | Fishman et al. | |
| 9,655,669 B2 | 5/2017 | Palti et al. | |
| 9,750,934 B2 | 9/2017 | Palti et al. | |
| 9,756,849 B2 | 9/2017 | Hassanein et al. | |
| 9,756,850 B2 | 9/2017 | Hassanein et al. | |
| 9,756,851 B2 | 9/2017 | Hassanein et al. | |
| 9,814,230 B2 | 11/2017 | Fishman et al. | |
| 9,894,894 B2 | 2/2018 | Hassanein et al. | |
| 9,910,453 B2 | 3/2018 | Wasserman et al. | |
| 10,039,276 B2 | 8/2018 | Hassanein et al. | |
| 10,076,112 B2 | 9/2018 | Hassanein et al. | |
| 10,188,851 B2 | 1/2019 | Wenger et al. | |
| 10,194,655 B2 | 2/2019 | Ritchie et al. | |
| 10,314,303 B2 | 6/2019 | Hassanein et al. | |
| 10,321,676 B2 | 6/2019 | Hassanein et al. | |
| 10,327,443 B2 | 6/2019 | Hassanein et al. | |
| 10,398,907 B2 | 9/2019 | Helekar et al. | |
| 10,500,408 B2 | 12/2019 | Helekar et al. | |
| 10,874,870 B2 | 12/2020 | Helekar et al. | |
| 2002/0151760 A1 | 10/2002 | Paturu | |
| 2004/0193001 A1 | 9/2004 | Miller | |
| 2005/0228209 A1 | 10/2005 | Schneider et al. | |
| 2006/0015153 A1 | 1/2006 | Gliner et al. | |
| 2006/0094924 A1 | 5/2006 | Riehl | |
| 2006/0122454 A1 | 6/2006 | Riehl et al. | |
| 2006/0265022 A1 | 11/2006 | John | |
| 2006/0282122 A1 | 12/2006 | Palti | |
| 2007/0093706 A1 | 4/2007 | Gevins | |
| 2007/0260107 A1 | 11/2007 | Mishelevich et al. | |
| 2008/0014285 A1 | 1/2008 | Di Mauro et al. | |
| 2008/0312706 A1 | 12/2008 | Zangen et al. | |
| 2009/0082690 A1 | 3/2009 | Phillips et al. | |
| 2009/0083071 A1 * | 3/2009 | Phillips | A61N 2/006 705/2 |
| 2010/0185042 A1 | 7/2010 | Schneider et al. | |
| 2010/0210894 A1 | 8/2010 | Pascual-Leone et al. | |
| 2010/0249488 A1 | 9/2010 | Kardos et al. | |
| 2011/0015469 A1 | 1/2011 | Walter et al. | |
| 2011/0034822 A1 | 2/2011 | Phillips et al. | |
| 2011/0105826 A1 | 5/2011 | Mishelevich et al. | |
| 2011/0112427 A1 | 5/2011 | Phillips et al. | |
| 2011/0118536 A1 | 5/2011 | Phillips et al. | |
| 2011/0118636 A1 | 5/2011 | Kitamura et al. | |
| 2011/0137104 A1 | 6/2011 | Phillips et al. | |
| 2011/0184223 A1 | 7/2011 | Peterchev et al. | |
| 2011/0270345 A1 | 11/2011 | Johnston et al. | |
| 2012/0053449 A1 | 3/2012 | Moses et al. | |
| 2012/0057752 A1 | 3/2012 | Li et al. | |
| 2012/0157752 A1 | 6/2012 | Nishikawa | |
| 2013/0090545 A1 | 4/2013 | Flynn | |
| 2013/0137918 A1 | 5/2013 | Phillips et al. | |
| 2014/0163305 A1 | 6/2014 | Watterson | |
| 2014/0179980 A1 | 6/2014 | Phillips et al. | |
| 2014/0200388 A1 | 7/2014 | Schneider et al. | |
| 2014/0276182 A1 | 9/2014 | Helekar et al. | |
| 2014/0276812 A1 | 9/2014 | Batchelor et al. | |
| 2016/0008620 A1 | 1/2016 | Stubbeman | |
| 2016/0193476 A1 | 7/2016 | Helekar et al. | |
| 2017/0136255 A1 | 5/2017 | Helekar et al. | |
| 2017/0215939 A1 | 8/2017 | Palti et al. | |
| 2017/0224990 A1 | 8/2017 | Goldwasser et al. | |
| 2017/0281934 A1 | 10/2017 | Giladi et al. | |
| 2018/0001075 A1 | 1/2018 | Kirson et al. | |
| 2018/0001078 A1 | 1/2018 | Kirson et al. | |
| 2018/0008708 A1 | 1/2018 | Giladi et al. | |
| 2018/0050200 A1 | 2/2018 | Wasserman et al. | |
| 2018/0078780 A1 * | 3/2018 | Sun | H01F 7/0221 |
| 2018/0160933 A1 | 6/2018 | Urman et al. | |
| 2018/0202991 A1 | 7/2018 | Giladi et al. | |
| 2018/0214710 A1 | 8/2018 | Charles et al. | |
| 2018/0229049 A1 | 8/2018 | Phillips et al. | |
| 2018/0350451 A1 | 12/2018 | Ohnemus et al. | |
| 2019/0117956 A1 | 4/2019 | Wenger et al. | |
| 2019/0209855 A1 * | 7/2019 | Helekar | A61B 5/4836 |
| 2019/0381333 A1 | 12/2019 | Helekar et al. | |
| 2020/0139147 A1 | 5/2020 | Helekar et al. | |

FOREIGN PATENT DOCUMENTS

| | | |
|---|---|---|
| CN | 105188844 A | 12/2015 |
| DE | 10 2011 050507 A1 | 11/2012 |
| EP | 2 968 968 A2 | 1/2016 |
| EP | 3 033 007 A4 | 5/2017 |
| WO | WO-2005/051306 A2 | 6/2005 |
| WO | WO-2009/033150 A1 | 3/2009 |
| WO | WO-2009/036040 A1 | 3/2009 |
| WO | WO-2010/025114 A1 | 3/2010 |
| WO | WO-2011/017466 A1 | 2/2011 |

(56) References Cited

FOREIGN PATENT DOCUMENTS

| WO | WO-2012/126044 A1 | 9/2012 |
|---|---|---|
| WO | WO-2014/152827 A2 | 9/2014 |
| WO | WO-2015/023980 A2 | 2/2015 |
| WO | WO-2016/059556 A1 | 4/2016 |
| WO | WO-2020/102312 A1 | 5/2020 |

OTHER PUBLICATIONS

Amassian, V. E et al., Transcranial Magnetic Stimulation in Study of the Visual Pathway, Journal of Clinical Neurophysiology, 1998, 15(4): 288-304.
Antal, A. et al., Electrical Stimulation and Visual Network Plasticity, Restorative Neurology and Neuroscience, 2011, vol. 29, pp. 365-374.
Azanon, E. et al., Somatosensory processing and body representation, Cortex 45, 2009, 1078-1084.
Beauchamp, M. S. et al., fMRI-Guided Transcranial Magnetic Stimulation Reveals That the Superior Temporal Sulcus is a Cortical Locus of the McGurk Effect,The Journal of Neuroscience, 2010, 30(7): 2414-7.
Beckers, G. et al., Cerebral visual motion blindness: transitory akinetopsia induced by transcranial magnetic stimulation of human area V5, Proceedings: Biological Sciences, 1992, 249(1325): 173-8.
Bikson, M. et al., Effects of Uniform Extracellular DC Electric Fields on Excitabiity in Rai Hippocampal Slices in Vitro, Journal of Physiology, 2004, vol. 557, pp. 175-190.
Buch, E. R. et al., Noninvasive Associative Plasticity Induction in a Corticocortical Pathway of the Human Brain, The Journal of Neuroscience, 2011, 31(48): 17669-79.
Cardenas-Morales, L. et al., Mechanisms and Applications of Theta-Burst rTMS on the Human Motor Cortex, Brain Topogr, 2010, vol. 22, pp. 294-306.
Chen, R. et al., The Clinical Diagnostic Utility of Transcranial Magnetic Stimulation: Repost of an IFCN Committee, Clinical Neurophysiology, 2008, vol. 119, pp. 504-532.
Dayan, Eran et al., Noninvasive brain stimulation: from physiology to network dynamics and back, Nature Neuroscience, Jul. 2013, vol. 16, No. 7.
De Pasquale et al., A Cortical Core for Dynamic Integration of Functional Networks in the Resting Human Brain, Neuron, 2012, 74(4): 753-64.
De Ridder, D. et al., Primary and Secondary Auditory Cortex Stimulation for Intractable Tinnitus, ORL, 2006, 68(1): 48-54.
Deans, J.K. et al,, Sensitivity of Coherent Oscillations in Rat Hippocampus to AC Electric Fields, Journal of Physiology, 2007, vol. 583, pp. 555-565.
Deco, G. et al., Ongoing Cortical Activity at Rest: Criticality, Multistability, and Ghost Attractors, The Journal of Neuroscience, 2012, 32(10): 3366-75.
Dell'Osso, B. et al., Meta-Review of Metanalytic Studies with Repetitive Transcranial Magnetic Stimulation (rTMS) for the Treatment of Major Depression, Clinical Practice & Epidemiology in Mental Health, 2011, 7, 167-77.
Delvendahl, I. et al., Plasticity of motor threshold and motor-evoked potential amplitude—A model of intrinsic and synaptic plasticity in human motor cortex?, Brain Stimulation 5, 2012, 586-593.
Devlin, J. T. et al., Stimulating language: insights from TMS, Brain, 2007, 130, 610-22.
Di Lazzaro, V. et al., Modulation of Motor Cortex Neuronal Networks by rTMS: Comparison of Local and Remote Effects of Six Different Protocols of Stimulation, Journal of Neurophysiology, 2011, vol. 105, pp. 2150-2156.
Esser, S.K. et al., Modeling the Effects of Transcranial Magnetic Stimulation on Cortical Circuits, Journal of Physiology, 2005, vol. 94, pp. 622-639.
Examination Report for BR Application No. 112015022834-8, dated Jul. 5, 2020.
Examination Report for BR Application No. 112016003147-4, dated Aug. 11, 2020.
Extended European Search Report for Application No. 14771163.4, dated Jan. 3, 2017.
Extended European Search Report for Application No. 14836452.4, dated May 2, 2017.
Farina, D. et al., Detecting the Unique representation of the Motor-Unit Action Potentials in the Surface Electromyogram, Journal of Neurophysiology, 2008, vol. 100, pp. 1223-1233.
First Examination Report for IN Application No. 201617008498, dated May 19, 2020.
First Examination Report for IN Application No. 9216/DELNP/2015, dated Jun. 5, 2020.
First Office Action for Chinese Application No. 201480027788.3, dated Oct. 10, 2016.
First Office Action for Chinese Application No. 201480057016.4, dated May 28, 2018.
Fitzgerald, P. B. et al., GABA and cortical inhibition in motor and non-motor regions using combined TMS-EEG: A time analysis, Clinical Neurophysiology 120, 2009, 1706-1710.
Fox, M. D. et al., The human brain is intrinsically organized into dynamic, anticorrelated functional networks, Proceedings of the National Academy of Sciences of the USA, 2005, vol. 102, No. 27, 9673-8.
Fregni, F. et al., Technology Insight: NonInvasice Brain Stimulation in Neurology: Perspectives on the Therapeutic Potential of rTMS and tDCS, Nature Clinical Practice Neurology, 2007, vol. 3, pp. 1-11.
Frohlich, F. et al., Endogenous Electric Fields May Guide Neocortlcai Network Activity, Neuron, Jul. 15, 2010, Voi. 67, pp. 129-143.
Frye, R.E. et al., Transcranial Magnetic Stimulation in Child Neurology: Current and Future Directions, Journal of Child Neurology, Jan. 2008, vol. 23, No. 1, pp. 79-96.
George, M.S. et al,, the Expanding Evidence Base for rTMS Treatment of Depression, Current Opinion on Psychiatry, Jan. 2013, vol. 26, No. 1, pp. 13-18.
Gonzalez-Rosa, J.J. et al.., Static Magnetic Field Stimulation over the Visual Cortex increases Alpha Oscillations and Slows Visual Search in Humans, The Journal of Neuroscience, Jun. 17, 2015, vol. 35, No. 24, pp. 9182-9193.
Guse, B. et al., Cognitive effects of high-frequency repetitive transcranial magnetic stimulation: a systematic review, Journal of Neural Transmission, 2010, 117: 105-22.
Helekar Santosh A., In Defense of Experience—Coding Nonarbitrary Temporal Neural Activity Patterns, Consciousness and Cognition, Dec. 1999, pp. 455-461, vol. 8, issue 4.
Helekar, S.A. et al., Electromyographic motor-evoked potentials elicited by transcranial magnetic stimulation with rapidly moving permanent magnets mounted on a multisite stimulator cap, Presentation Abstract, Nov. 13, 2013.
Helekar, Santosh A., On the Possibility of Universal Neural Coding of Subjective Experience, Consciousness and Cognition, Dec. 1999, pp. 423-446, vol. 8, Issue 4.
Helekar, Santosh et al., Transcranial Brain Simulation With Rapidly Spinning High-Field Permanent Magnets, IEEE Access, vol. 4, May 19, 2016, pp. 2520-2527.
Helfrich, R.F. et al., Entrainment of Brain Oscillations by Transcranial Alternating Current Stimulation, Current Biology, Feb. 3, 2014, vol. 24, pp. 333-339.
Huerta, P. T. et al., Transcranial magnetic stimulation, synaptic plasticity and network oscillations, Journal of NeuroEngineering and Rehabilitation, 2009, 6:7.
Ilic, T. V. et al., Exploring Motor Cortical Plasticity Using Transcranial Magnetic Stimulation in Humans, Annals of the New York Academy of Sciences, 2005, vol. 1048(1): 175-184.
International Preliminary Reporton Patentability for Application No. PCT/US2014/027900, dated Sep. 15, 2015.
International Preliminary Reporton Patentability for Application No. PCT/US2014/051340, dated Feb. 16, 2016.
International Preliminary Reporton Patentability for Application No. PCT/US2017/031413, dated Nov. 15, 2018.
International Search Report and Written Opinion for Application No. PCT/US2014/027900, dated Sep. 4, 2014.

(56) References Cited

OTHER PUBLICATIONS

International Search Report and Written Opinion for Application No. PCT/US2014/051340, dated Apr. 15, 2015.
International Search Report and Written Opinion for Application No. PCT/US2017/031413, dated Aug. 14, 2017.
International Search Report and Written Opinion for Application No. PCT/US2019/061131, dated Apr. 28, 2020.
International Search Report and Written Opinion for Application No. PCT/US2021/038052, dated Oct. 13, 2021.
Jin, Y. et al., A Pilot Study of the Use of EEG-Based SynchornIzed Transcranial Magnetic Stimulation (sTMS) for Treatment of Major Depression, BMC Psychiatry, 2014, Voi. 14, No. 13, pp. 1-6.
Kamitani, Y. et al., Manifestation of scotomas created by transcranial magnetic stimulation of human visual cortex, Nature Neuroscience, 1999, 2(8): 767-71.
Kamke, M. R. et al., Parietal disruption alters audiovisual binding in the sound-induced flash illusion, NeuroImage 62, 2012, 1334-1341.
Kammer, T., Masking visual stimuli by transcranial magnetic stimulation, Psychological Research, 2007, 71: 659-66.
Leuchter, A. F. et al., Synchronized Transcranial Magnetic Stimulation (sTMS) Efficacy and Safety of Low-field Synchronized Transcranial Magnetic Stimulation (sTMS) for Treatment of Major Depression, Brain Stimulation, 2015, 1-8.
Levasseur-Moreau, J. et al., Translational application of neuromodulation of decision-making, Brain Stimulation 5, 2012, 77-83.
Lipton, R. B. et al., Transcranial Magnetic Simulation in the Treatment of Migraine, Neurotherapeutics: The Journal of the American Society for Experimental NeuroTherapeutics, 2010, vol. 7, 204-12.
Muller, P. A. et al., Safety and tolerability of repetitive transcranial magnetic stimulation in patients with pathologic positive sensory phenomena: a review of literature, Brain Stimulation, 2012, 5(3): 320-329.
Muller-Dahlhaus, F. et al., Plasticity resembling spike-timing dependent synaptic plasticity: the evidence in human cortex, Frontiers in Synaptic Neuroscience, 2010, vol. 2, Article 34, 1-11.
Nakatani-Enomoto, S. et al., Bidirectional modulation of sensory cortical excitability by quadripulse transcranial magnetic stimulation (QPS) in humans, Clinical Neurophysiology 123, 2012, 1415-1421.
Office Action for Canadian Application No. 2,942,653, dated Aug. 7, 2020.
Office Action for Canadian Application No. 2,942,653, dated Jul. 19, 2019.
Office Action for Canadian Application No. 2,942,653, dated Jun. 18, 2021.
Office Action, European Patent Application No. 14771163.4, dated Mar. 20, 2019.
Olivierg, A. et al., Transcranial Static Magnetic Field Stimulation of the Human Motor Cortex, Journal of Physiology, 2011, vol. 589, No. 20, pp. 4949-4958.
Pitcher, D. et al., Transcranial Magnetic Stimulation Disrupts the Perception and Embodiment of Facial Expressions, The Journal of Neuroscience, 2008, 28(36): 8929-33.
Rivadulla, C. et al., Magnetic Field Strength and Reproducibility of Neodymium Magnets Usefui for Transcranial Static Magnetic Field Stimulation of the Human Cortex, Neuromodulation: Technology at the Neural interface, 2014, vol. 17, No. 5, pp. 438-442.
Rossi S. et al., Safety, ethical considerations, and application guidelines for the use of transcranial magnetic stimulation in clinical practice and research, Clinical Neurophysiology, 2009, 2008-2039.
Sanchez, Alvaro et al., Antimagnets: Controlling Magnetic Fields With Superconductor—Metamaterial Hybrids, New Journal of Physics, 2011, vol. 13.
Sandrini, M. et al., The use of transcranial magnetic stimulation in cognitive neuroscience: A new synthesis of methodological issues, Neuroscience and Biobehavioral Reviews 35, 2011, 516-536.
Second Office Action for Chinese Application No. 201480027788.3, dated Aug. 14, 2017.
Second Office Action for Chinese Application No. 201480057016.4, dated Apr. 3, 2019.
Thielscher, A, et al., Linking Physics with Physiology in TMS: A Sphere Field Model to Determine the Cortical Stimulation Site in TMS, Neuroimage, 2002, vol. 17, pp. 1117-1130.
Third Office Action for Chinese Application No. 201480027788.3, dated Mar. 6, 2018.
Third Office Action for Chinese Application No. 201480057016.4, dated Sep. 12, 2019.
Wassermann, E. M. et al., Transcranial Magnetic Brain Stimulation: Therapeutic Promises and Scientific Gaps, Pharmacology and Therapeutics, 2012, 133(1): 98-107.
Wassermann, E. M., Risk and safety of repetitive transcranial magnetic stimulation: report and suggested guidelines from the International Workshop on the Safety of Repetitive Transcranial Magnetic Stimulation, Jun. 5-7, 1996, Electroencephalographyand Clinical Neurophysiology, 1998, 108, 1-16.
Zaehle, T. et al., Transcranial Alternating Current Stimulation Enhances Individual Alpha Activity in Human EEG, PloS one, Nov. 2010, vol. 5, No. 11, pp. 1-7.

* cited by examiner

METHOD AND APPARATUS FOR ONCOMAGNETIC TREATMENT

CROSS REFERENCE TO RELATED APPLICATIONS

This application is a continuation patent application of PCT application US2021/038052, filed on Jun. 18, 2021 and titled "Method and Apparatus for Oncomagnetic Treatment," which claims the benefit of priority to provisional U.S. application No. 63/201,681 filed on May 7, 2021 and provisional U.S. application No. 63/041,658 filed on Jun. 19, 2020. Each of the foregoing applications are herein incorporated by reference in their entirety for all purposes.

FIELD OF THE DISCLOSURE

This disclosure generally relates to cancer treatment methods and apparatus and, more particularly, to non-invasive cancer treatments utilizing oscillating magnetic fields.

BACKGROUND

Cancer is one of the biggest health problems facing modern society, and improvements in aggressive treatments for some forms of cancer, including glioblastoma—(GBM) remain dismal. Common forms of cancer treatment include chemotherapy and radiotherapy which can be devastating to the patient's body, causing severe physical and mental trauma. The heavy toll on patients can result in a patient deciding not to complete the suggested chemotherapy or radiation treatment cycles. Thus, there is a need for a cancer treatment approach with better life-expectancy outcome and less toxicity.

Recently, applying alternating electric fields (AEFs) to the scalp, a treatment called Tumor Treating Field (TTF) therapy or Optune® therapy, has shown therapeutic benefit in patients with GBM. TTF therapy has been approved by the U.S. Food and Drug Administration as monotherapy for GBM and in combination with other therapies for newly diagnosed GBM. TTF therapy is commonly administered to patients by attaching electrodes to a patient's head, which requires shaving the patient's head at electrode sites. Moreover, electrodes often cause lesions on the skin, rashes, other dermatological adverse effects, and in some cases even cause burns due to applied electrical currents.

SUMMARY

Generally speaking, the system of this disclosure causes apoptosis, or another mechanism of cell death, in cancer cells by rapidly oscillating one or more magnets to generate an oscillating magnetic field (OMF) to disrupt electron flow; for example in the mitochondrial electron transport chain (ETC), thereby disrupting mitochondrial function. The system can apply OMFs without directly contacting the subject's scalp when used treat to a brain tumor, or the subject's skin when used with other parts of the body.

The system can include one or more stimulators, each including a permanent magnet and an electric motor configured to communicate oscillating motion (e.g., rotation, translational oscillation) to the permanent magnet. Advantageously, these techniques do not require passing a large current through coils or solenoids, for example. In some implementations, the stimulators are miniaturized and are referred to as "microstimulators." When the system includes multiple stimulators, the controlling hardware can cause the stimulators to operate at different times, at different frequencies, at different pulse rates, etc. to define a particular stimulation pattern, which can be subject-specific.

One embodiment of these techniques is a method for disrupting mitochondrial function or inducing apoptosis, or another mechanism of cell death, in cancer cells. The method includes causing, by controlling hardware, a one or more magnets along (i) a first axis and a (ii) a second axis substantially orthogonal to the first axis, to oscillate so as to generate an oscillating magnetic field, and applying the oscillating magnetic field to a tissue comprising cancer cells. In various embodiments the cancer cells have mitochondrial impairment to trigger apoptosis, or another mechanism of cell death, in the cancer cells with mitochondrial impairment. In related embodiments, causing the one or more magnets to oscillate further comprises causing the one or more magnets to oscillate along a third axis substantially orthogonal to the first axis and the second axis. In a related embodiments, applying the oscillating magnetic field to the tissue increases the production of reactive oxygen species (ROS) and/or induces an alteration of electron flow in the tissue. In a related embodiments, the alteration of electron flow in the tissue induces apoptosis, or another mechanism of cell death, in cancer cells with mitochondrial impairment and not in non-cancerous cells without mitochondrial impairment.

Another embodiment of these techniques is a method for inducing apoptosis, or another mechanism of cell death, in cancer cells. The method includes generating an oscillating magnetic field by controlling hardware and applying the oscillating magnetic field to a tissue comprising cancer cells for inducing apoptosis, or another mechanism of cell death, in the cancer cells through the increased production of reactive oxygen species (ROS).

Another embodiment of these techniques is a method for oncomagnetic treatment of a tumor. The method includes introducing a chemical into a tissue comprising the tumor; generating, by controlling hardware, an electromagnetic signal parameterized to treat the tumor by (i) preventing cell division or growth, and/or (ii) causing cell death; and applying the electromagnetic signal to the tissue to alter electron flow in the tissue, wherein the chemical potentiates the treatment of the tumor.

In various embodiments, the chemical includes, but is not limited to, a ketone body (e.g. β-hydroxybutyrate or acetoacetate), or acetate, or free fatty acid (e.g. octanoate, stearic acid, or palmitate), or branched chain amino acid (e.g. leucine, isoleucine or valine), or cryptochrome agonist (e.g. KL001), O(6)-Methylguanine-DNA methyltransferase (MGMT) inhibitor (e.g. O6-benzylguanine), or DNA alkylating agent, or DNA methylating agent may be provided to a region of tissue or cell, tumor, or cancer cells in addition to the oncomagnetic therapy to complement the oncomagnetic therapy.

Another embodiment of these techniques is a system for disrupting mitochondrial function in cells. The system includes at least one stimulator/oscillator including one or more magnets and a controlling hardware configured to cause one or more magnets along (i) a first axis and a (ii) a second axis substantially orthogonal to the first axis, to oscillate so as to generate an oscillating magnetic field that, when applied to a tissue comprising cells with mitochondrial impairment, triggers apoptosis, or another mechanism of cell death, in the cells with the mitochondrial impairment.

Another embodiment of these techniques is a device for providing an OMF treatment to a subject/patient. The device includes a plurality of ribs configured to articulate relative to a frame so as to fit around a head of a patient and a plurality of inserts, each configured to attach to at least one of the plurality of ribs and support one or more magnetic stimulators to generate an oscillating magnetic field for application to the head of the patient.

Yet another embodiment of these techniques is a method for disrupting mitochondrial function in cancer cells. The method includes generating, in a tissue including cancer cells, the disruption of electrons to cause apoptosis, or another mechanism of cell death, in the cancer cells through (i) a decrease in mitochondrial glucose oxidation in glucose oxidation in a tricarboxylic acid (TCA) cycle, (ii) an increase in a metabolic flux of glycolysis, (iii) an increase in superoxide, peroxide and other reactive oxygen species generation, (iv) the opening of the mitochondrial membrane permeability transition pore, (v) an increase in fission of mitochondrial networks in the cancer cells, and/or (vi) activation of caspase-3-mediated apoptotic pathway or an alternate apoptotic mechanism in the cancer cells.

In other embodiments, the disclosure provides for a use for disrupting mitochondrial function in cells. The use includes causing, by controlling hardware, a one or more magnets along (i) a first axis and a (ii) a second axis substantially orthogonal to the first axis, to oscillate so as to generate an oscillating magnetic field, and applying the oscillating magnetic field to a tissue comprising cells with mitochondrial impairment to trigger apoptosis, or another mechanism of cell death, in the cells with mitochondrial impairment. In a related embodiments, causing the one or more magnets to oscillate further comprises causing the one or more magnets to oscillate along a third axis substantially orthogonal to the first axis and the second axis.

In other embodiments, the disclosure provides a use for inducing apoptosis, or another mechanism of cell death, in cancer cells. The use includes generating an oscillating magnetic field by controlling hardware and applying the oscillating magnetic field to a tissue comprising cancer cells for inducing apoptosis, or another mechanism of cell death, in the cancer cells through the increased production of reactive oxygen species (ROS).

In other embodiments, the disclosure provides a use for oncomagnetic treatment of a tumor. The use includes introducing a chemical into a tissue comprising the tumor; generating, by controlling hardware, an electromagnetic signal parameterized to treat the tumor by (i) preventing cell division or growth, and/or (ii) causing cell death; and applying the electromagnetic signal to the tissue to alter electron flow in the tissue, wherein the chemical potentiates the treatment of the tumor.

Yet another embodiment of these techniques is a use for disrupting mitochondrial function in cancer cells. The use includes generating, in a tissue including cancer cells, the disruption of electrons to cause apoptosis, or another mechanism of cell death, in the cancer cells through (i) a decrease in mitochondrial glucose oxidation in glucose oxidation in a tricarboxylic acid (TCA) cycle, (ii) an increase in a metabolic flux of glycolysis, (iii) an increase in superoxide, peroxide and other reactive oxygen species generation, (iv) the opening of the mitochondrial membrane permeability transition pore, (v) an increase in fission of mitochondrial networks in the cancer cells, and/or (vi) activation of caspase-3-mediated apoptotic pathway or an alternate apoptotic mechanism in the cancer cells.

Throughout this disclosure and the claims which follow, unless the context requires otherwise, the word "comprise", and variations such as "comprises" and "comprising", will be understood to imply the inclusion of a stated feature or step or group of features or steps but not the exclusion of any other feature or step or group of features or steps. When used herein the term "comprising" can be substituted with the term "containing" or "including" or sometimes when used herein with the term "having." When used herein, "consisting essentially of" does not exclude features or steps that do not materially affect the basic and novel characteristics of the claim. When used herein, "consisting of" excludes any feature or step not specified in the claim element. In each instance herein any of the terms "comprising", "consisting essentially of" and "consisting of" may be replaced with either of the other two terms. With respect to aspects of the disclosure described or claimed with "a" or "an," it should be understood that these terms mean "one or more" unless context unambiguously requires a more restricted meaning.

BRIEF DESCRIPTION OF THE DRAWINGS

in FIG. 5A, images of GBM cells stained with MitoTracker show no changes in the cells undergoing sham-stimulation; in FIG. 5B, the images show fission of mitochondrial network after 10 min of OMF stimulation; in FIG. 5C, the images of OMF-stimulated cells stained with MitoSOX™ show that the intensity of fluorescent mitochondria increases; tracking the strand (arrow in second panel) between two cells shows thinning during OMF stimulation, which continues post stimulation.

in FIG. 23A, the second half of the Q-cycle begins with electron transfer to the Rieske center; in FIG. 23B, the formation of 3 biradical pairs during the operation of the Q-cycle; in FIG. 23C, electron transfer events between the two semiquinones and reduction of cytochrome $c_1$; in FIG. 23D, the redox state of the fully oxidized $bc_1$ complex before the next cycle begins; in FIG. 23E, the conversion of the singlet to triplet state of the Rieske/$c_1$ biradical pair by interaction with the imposed field generates a spin-forbidden electron pairing; in FIG. 23F, the conversion of the singlet to triplet state of the Qp semiquinone/$b_L$ heme biradical pair by interaction with the imposed field generates a spin-forbidden electron pairing and increases the probability that superoxide will be generated by the reaction of $O_2$ and the semiquinone; in FIG. 23G, the conversion of the singlet to triplet state of the QN semiquinone/$b_H$ heme biradical pair by interaction with the imposed field generates a spin-forbidden electron pairing and, again, increases the probability that superoxide will be generated by the reaction of $O_2$ and the semiquinone.

DETAILED DESCRIPTION

Figure 1:
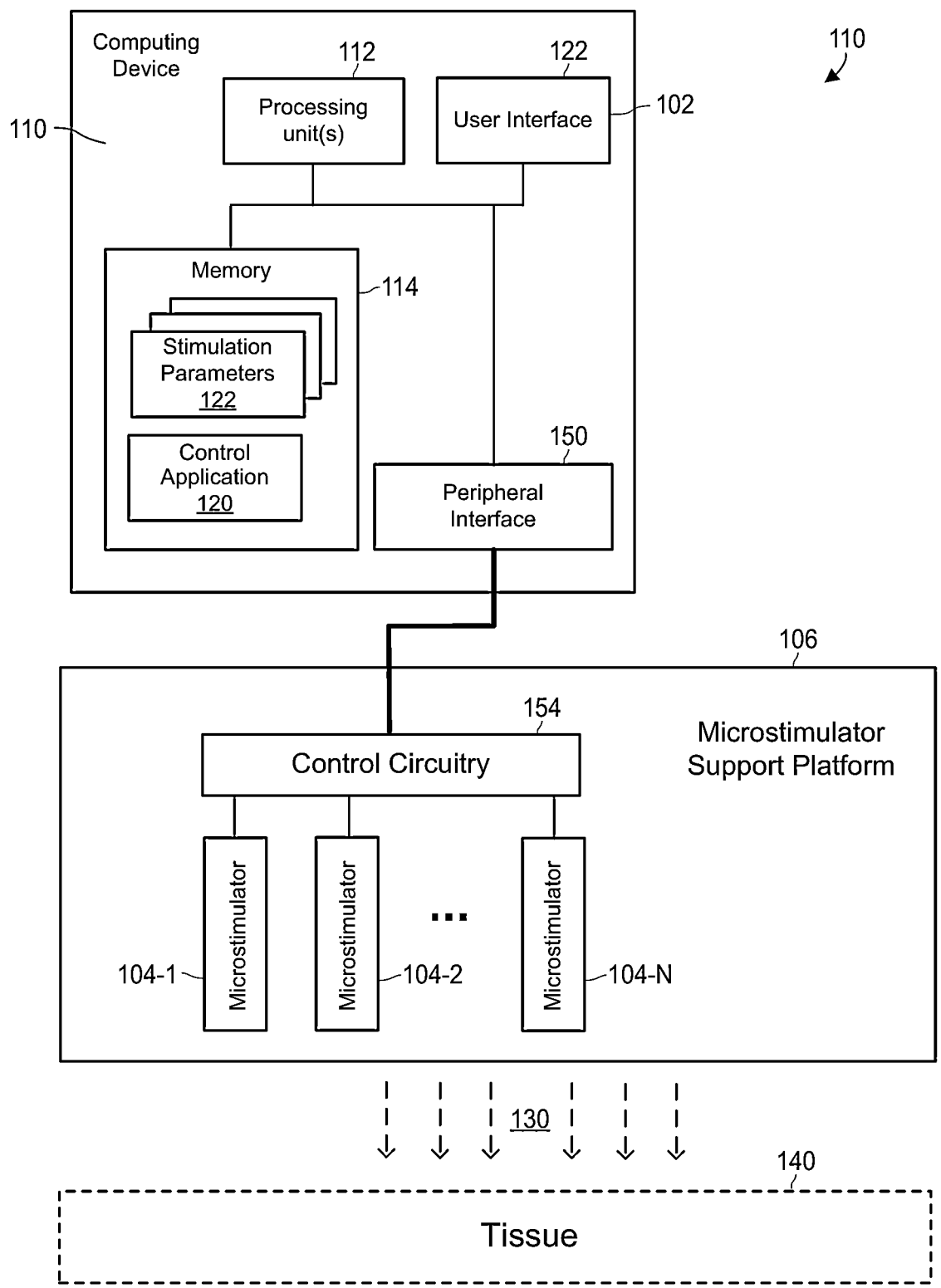
FIG. 1 is a block diagram of a system for disrupting mitochondrial function in certain cells by applying a rapidly changing magnetic field, according to one example implementation.

Effect of Oscillating Electromagnetic Fields on Tumors

A system of this disclosure applies oscillating magnetic fields, and more particularly, rapidly changing magnetic fields, to tissue so as to target cancer cells. Generally speaking, cancer cells have altered bioenergetics, mitochondrial function, and a reduced number of mitochondria due to uncontrolled cell division. One such alteration seen in these cells due to mutations in the electron transport chain which may play a role in carcinogenicity (i.e., inducing of tumors). The system of disclosure uses the anti-cancer effects of oscillating magnetic fields on tumors. Evidence suggests that these anti-cancer effects are due to changes in the fluxes through bioenergetic and redox mechanisms in cancer cells. The methods and apparatus disclosed employ oscillating magnetic fields generated by rapid rotation or translation of strong permanent magnets with high field strengths. The application of the oscillating magnetic field causes a substantial decrease in the flux through the reductive carboxylation pathway in patient-derived GBM cells, which might be related to the anti-cancer effect.

Glutamine is an essential amino acid with many functions including being a major bioenergetic nutrient for cancer cells. Glutamine provides energy and carbon precursors for macromolecular synthesis that is required for biomass production, and specifically glutamine acts as an energy source for rapidly dividing cells. Aside from glucose, glutamine is the most rapidly consumed nutrient by many types of cultured cancer cells. Glutamine is converted to glutamate upon entering the cells by glutaminase (GLS), which enters the tricarboxylic acid (TCA) cycle through the conversion into α-ketoglutarate (α-KG) by glutamate to generate oxaloacetate (OAA), citrate and other TCA cycle intermediates. Citrate is an important 6 carbon TCA cycle intermediate that is necessary to maintain mitochondrial oxidative metabolism and cytosolic biomolecular synthesis. Mitochondrial citrate is generated through multiple nutrient sources. Glucose-derived pyruvate produces acetyl-CoA via pyruvate dehydrogenase (PDH) that condenses with OAA to generate citrate. In many cancer cells, pyruvate carboxylase acts as a major anaplerotic pathway that also generates citrate from pyruvate through the production of OAA in the TCA cycle. Cancer cells with altered mitochondrial function (due to either mutations in electron transport chain (ETC) or tricarboxylic acid cycle enzymes) are capable of generating citrate through reductive carboxylation of glutamine-derived α-ketoglutarate. ATP-citrate lyase (ACL) cleaves exported citrate in the cytosol to produce acetyl-CoA which is further used as precursor for lipid de novo synthesis.

The system of this disclosure uses electromagnetic fields (EMF) to modulate cellular metabolism. Long exposures to repeated EMF pulses, radiating radiofrequency waves, or non-radiating local field oscillations have varying degrees of efficacy against cancer cells in culture. Cancer cells are oxidatively stressed, compared to normal cells of the same tissue, and have high levels of reactive oxygen species (ROS) which, if accentuated further, leads to cancer cell apoptosis, or another mechanism of cell death. The application of EMF pulses on cells causes an increase in the intracellular levels of ROS leading to cell apoptosis, or another mechanism of cell death. Disclosed herein are methods and systems for generating an oscillating magnetic field (OMF) for in vitro and in vivo treatment of tumors and cancerous tissue by inducing the generation of ROS and causing cancer cell apoptosis, or another mechanism of cell death.

As described herein, "magnetic stimulators" or "microstimulators" generate OMFs through the rotation of permanent magnets at high speeds. The microstimulators are configured to produce patterns of magnetic field oscillations that cause selective apoptosis, or another mechanism of cell death, of cultured GBM cells, without causing apoptosis, or another mechanism of cell death, in normal astrocytes. The lack of lethality in normal cells is due to an abundance of mitochondria, absent or reduced oxidative stress, and much lower demand for ATP compared to rapidly dividing malignant cells. In fact, repetitive magnetic stimulation has shown decreased apoptosis in non-cancerous cells. By applying OMFs at certain ranges of frequencies applied in defined pulsed patterns, the system causes the disruption of electron flow in the mitochondrial electron transfer chain (ETC), in turn causing the generation of ROS. The ROS cause the opening of the mitochondrial permeability transition pore (MPTP), resulting in mitochondrial membrane depolarization and extrusion of cytochrome C, and triggering caspase-dependent cell death by an alternate mechanism in the cancer cell. The microstimulators may also be referred to herein as oncoscillators due to the tumor-tissue selective nature of the treatment methods and systems described herein. In various embodiments, the systems can include microstimulator probes, wearable apparatus with multiple oncoscillators, and fixtures for surrounding a patient or body of tissue for treatment.

The OMF therapy methods and systems described do not have the limitations of chemotherapeutic agents such as the need for adequate blood supply to all parts of the malignant tumor, the ability to penetrate the blood brain barrier in case of brain cancers, a high enough bioavailability, a favorably tuned pharmacokinetic profile, a sufficiently large therapeutic index, etc. In addition, a variety of OMF treatment delivery mechanisms are available with great flexibility and versatility to have a substantial impact on all types of primary and metastatic solid neoplasms, and possibly systemic malignancies as well. Additionally, it is possible to administer OMF treatment sessions as only one to three hours of application a day, whereas TTF therapy requires 18 to 20 hours of treatment each day. The proposed methods and systems for OMF therapy cost much less than TTF therapy. The specific OMF frequencies and amplitudes selectively kill cancer cells in any stage of the cell cycle and do not depend on cell division, depend on being in a mitotic state, or depend on any other state. In fact, the methods and systems disclosed can selectively kill cancer cells in the G0 phase of the cell cycle. The method and systems for oncomagnetic therapy described herein can be drug-free, ionizing radiation-free, and non-invasive, or oncomagnetic therapy may be performed in conjunction with other forms of therapy such as with chemotherapy, other forms of radiative therapy, with drugs and prescriptions, etc.

According to at least some of the techniques of this disclosure, a system generates oscillating magnetic fields to induce alteration of electron flow in a tissue. However, it is believed that at least some of these techniques also can be used with AEF techniques to eliminate the need to directly apply electrodes to the patient's skin, for example. More particularly, it may be possible to use oscillating magnets to generate AEFs with properties similar to those used in TTF therapy.

An Example System for Disrupting Mitochondrial Function in Cells

FIG. 1 illustrates an example implementation system 100 for disrupting mitochondrial function in certain cells by applying a rapidly changing magnetic field. The system 100 includes a computing device 102 that controls magnetic stimulators 104-1, 104-2, ... 104-N mounted on a stimulator support platform 106, which can be a probe, helmet, a brace, a belt, mechanical frame, room, bed, cubicle, etc. Because the stimulators 104 can be miniaturized to be, for example, 500 millimeters, 1 cm, 2 cm, etc. along the longest dimension, the magnetic stimulators 104 are referred to below as microstimulators 104. Further, due to the particular application of the magnetic fields discussed herein, the magnetic stimulators 104 can be referred to as "oncoscillators." The computing device 102 includes controlling hardware 110 that can include one or more processing units 112 coupled to a non-transitory computer-readable memory 114 storing a control application 120 and stimulation parameters 122.

In operation, the controlling hardware 110 causes the microstimulators 104 to generate an oscillating magnetic field 130 and, using the stimulator support platform 106, apply the oscillating magnetic field 130 to a tissue 140. The microstimulators 104 generate the oscillating magnetic field 130 in a manner that causes disruption of mitochondrial function in cells of the tissue 140. As discussed in more detail below, the oscillating magnetic field 130 disrupts electron flow in the cells, such that apoptosis, or another mechanism of cell death, is triggered in the cancer cells, but no apoptosis or cell death is triggered in the healthy cells of the tissue 140.

In addition to being capable of altering electron flow in cell tissue without directly contacting the subject's scalp or skin on other parts of the body, the system 100 provides an additional advantage of being configurable for a variety of different solid cancers. As discussed below, various stimulation parameters and stimulation parameters can generate different configurations of OMF, which can be tailored for a specific cell type and/or specific subject to implement a personalized treatment protocol. Further, the system has the advantage of an imperceptible sham treatment capability to serve as a placebo control in double-blind trials. In particular, high-field strength magnets in the microstimulators discussed below can be replaced with demagnetized magnets. Because a human subject cannot sense the magnetic field, research subject and investigators cannot distinguish between an operational instance of the system 100 and a sham stimulation system by inspection or during a treatment session.

The computing device 102 can be a general-purpose computing device such as a desktop computer, a laptop computer, a table computer, a smartphone, a wearable device such as a smartwatch, etc. The one or more processing units 112 in these implementations can be central processing units (CPUs), and the memory 114 can include persistent components (e.g., a flash drive, a disk) as well as non-persistent components (e.g., Random Access Memory (RAM)). In other implementations, the computing device 102 is a special-purpose medical device configured specifically to control the one or more microstimulators 104. The processing units 112 in this case can include a field programmable gate array (FPGA), an application-specific integrated circuit (ASIC), or any other type of special-purpose hardware. Further, the controlling hardware 110 in some implementations is embedded in the stimulator support platform 106.

The control application 120 can and one or more sets of stimulation parameters 122 which can specify, for a certain stimulation session, at least some of: the duration of the session, pulse width (length) of stimulus pulses, the duration of stimulus pulse intervals, and the frequency of oscillation of the magnets. The stimulation parameters 122 in some cases can define separate sets of values for different microstimulators 104-1, 104-2, . . . 104-N, to define a particular stimulation pattern. More particularly, the stimulation pattern can specify a certain time of activation and operational parameters (frequency, pulse parameters) for the microstimulator 104-1, specify a different time of activation and different operational parameters for the microstimulator 104-2, etc. These parameters in some cases can depend on the relative positioning of the microstimulators 104, so that for example a microstimulator 104-i and a microstimulator 104-j positioned at a certain distance and oriented at a certain angle relative to each other generate stimulation pulses with a certain phase offset, so as to generate an oscillating magnetic field with certain desired characteristics.

In the example of FIG. 1, the computing device 102 includes a peripheral interface 150 and a user interface 152, in addition to the one or more processors 112 and the memory 114. The peripheral interface 152 can be Serial Peripheral Interface (SPI), a Universal Serial Bus (USB), or any suitable wireless interface such as Wireless Personal Area Network (WPAN) interface (e.g., Bluetooth®), a Wireless Local Area Network (WLAN) interface (e.g., Wi-Fi®), etc. The computing device 102 can use the peripheral interface 150 to transmit commands to the microstimulators 104. More particularly, the computing device 102 in the example implementation of FIG. 1 provides commands to the microstimulators 104 via the peripheral interface 150 and a control circuitry 154 of the stimulator support platform 106.

The control circuitry 154 can be configured to receive commands for the individual microstimulators 104-1, 104-02, etc. and turn on or off the motors in the microstimulators 104-1, 104-02, etc., vary the speed of rotation or other type of oscillation in the motors, etc. The control circuitry 154 thus can operate as a demultiplexer. Further, as indicated above, in some implementations the controlling hardware 110 is embedded in the stimulator support platform 106, and thus the entire control functionality of the system 100 can be provided in the control circuitry 154. More generally, control functionality of the system 100, such as the control logic for activating the microstimulators 104 in accordance with various stimulation patterns, can be distributed between the computing device 102 and the control circuitry 154 in any suitable manner, including providing the entire control functionality entirely in the computing device 102 or entirely in the control circuitry 154.

The user interface 152 can include a touchscreen configured to receive input and display output or separate input (e.g., a keyboard, a pointing device) and output (e.g., a display) components. An operator can use the user interface 152 to provide commands to select the desired particular stimulation parameters 122 for a particular microstimulator or a stimulation pattern that includes multiple stimulation parameters 122 for the respective microstimulators. Further, the system 100 in some implementations can include one or more magnetic sensors such as microelectromechanical system (MEMS) sensors, and the user device 102 can provide readings from these magnetic sensors via the user interface 152.

The microstimulator platform 106 can be a harness, a helmet, a brace, etc. Further, the microstimulator platform 106 can be a part of a hospital bed, and the system 100 in some cases can apply stimulation to a sleeping subject. Still further, the microstimulator platform 106 in some implementations can be an intraoperative probe which a clinician can guide manually. In some implementations, the microstimulator platform 106 includes one or more magnetic sensors to provide sensor readings to the operator as discussed above and/or provide a feedback signal to the controlling hardware 110, so that the controlling hardware 110 can tune certain operational parameters to achieve the desired strength of the magnetic field.

The microstimulator platform 106 in some implementations can include a power storage device, such as a battery, to power the microstimulators 104. In other implementations, the computing device 102 can be configured to provide electric power to the microstimulator platform 106 via the peripheral interface 150.

The system 100 in various scenarios can generate stimulation sessions that are intermittent or continuous, ranging in duration from 1 minute to 20 hours for a given therapy session, depending on the amount of desired stimulation determined by a treatment plan. In various aspects, the oscillating magnetic field intermittently or continuously during of a period of between about 20-30 hours. The frequency of each oscillatory stimulus, and therefore the oscillatory motion of the motor, can range from 5 Hertz to 400 Hertz. In various aspects, the frequency of each oscillatory stimulus, and therefore the oscillatory motion of the motor is 30-300 Hertz. In various aspects, the frequency of each oscillatory stimulus, and therefore the oscillatory motion of the motor is about 300 Hertz. The microstimulators 104 can provide oscillatory stimulus as one or more pulses in a series. In some example implementations, the pulse lengths range from about 10 milliseconds to about 5 seconds, with inter-stimulus pulse intervals ranging from about 10 milliseconds to about 10 minutes, resulting in pulse train duty cycles ranging from 0.001% to 50%. The oscillatory frequency, timing, pulse duration, and inter-stimulus pulse interval of the oscillatory stimulus any of the microstimulators 104 provide may be kept the same, varied in groups, and/or varied independently for each microstimulators 104. The oscillatory stimulus pulses may vary in temporal length and inter-stimulus pulse interval from pulse to pulse as required to provide adequate field intensity to a target site or volume. The stimulus pulses may have amplitude envelopes whose shapes are square, Gaussian, sinusoidal, ramp, sawtooth, etc., to provide adequate field amplitude to a target site or volume. Additionally, the system 100 can ramp the oscillatory frequency up and/or down to maximum desired frequencies or between frequencies for a given therapeutic session.

In some implementations, the controlling hardware 110 can activate the microstimulators 104 one at a time, simultaneously, sequentially, in-pairs, in groups, or according to any combination thereof (e.g. sequentially in pairs, one group at a time). In fact, the controlling hardware 110 can activate any number of microstimulators 104 in any sequence able to deliver the desired OMF to a target site or volume.

The controlling hardware 110 in some cases can implement a beat frequency stimulation when generating OMF in a target site or volume. According to the beat frequency stimulation approach, the controlling hardware 110 causes the magnets in two microstimulators to oscillate at different frequencies so as to produce a beat frequency at a target site or volume. For example, the microstimulator 104-1 can oscillate at 320 Hz, while the microstimulator 104-2 can oscillate at 400 Hz. Due to electromagnetic interference, the microstimulator 104-1 and 104-2 generate a beat frequency of 80 Hz (which is the difference between the frequencies of 320 Hz and 400 Hz) at a target site or volume. The amplitude of the OMF at this beat frequency is twice the amplitude of the OMF the microstimulator 104-1 or 104-02 induces independently. The system 100 can implement beat frequency stimulation when high-amplitude low-frequency fields are required or desirable in treatment.

Due to the small dimensions of the magnets and motors in the microstimulators 104, as well as the ability to operate using a battery, the system 100 can be portable. Therefore, treatment may be performed at any time or location. Moreover, the control application 120 can be installed on a smartphone, a tablet computer, or a portable computer device as discussed above.

As discussed above, the control application 120 can operate according to the stimulation parameters 122 and various stimulation patterns or preprogrammed therapy sessions. The control application 120 additionally can implement safety features such as limiting the amount of treatment a patient can receive daily, weekly, or monthly, limiting how often or when a patient can apply treatment (e.g., only on weekdays, only on a specific day of the week, only for a period of four weeks).

Next, the mechanisms by which the system 100 causes apoptosis, or another mechanism of cell death, in certain cells of the tissue 140, and certain test results produced when the system 100 in one example implementation operated on certain samples, are discussed with reference to FIGS. 2-8.

Figure 2:
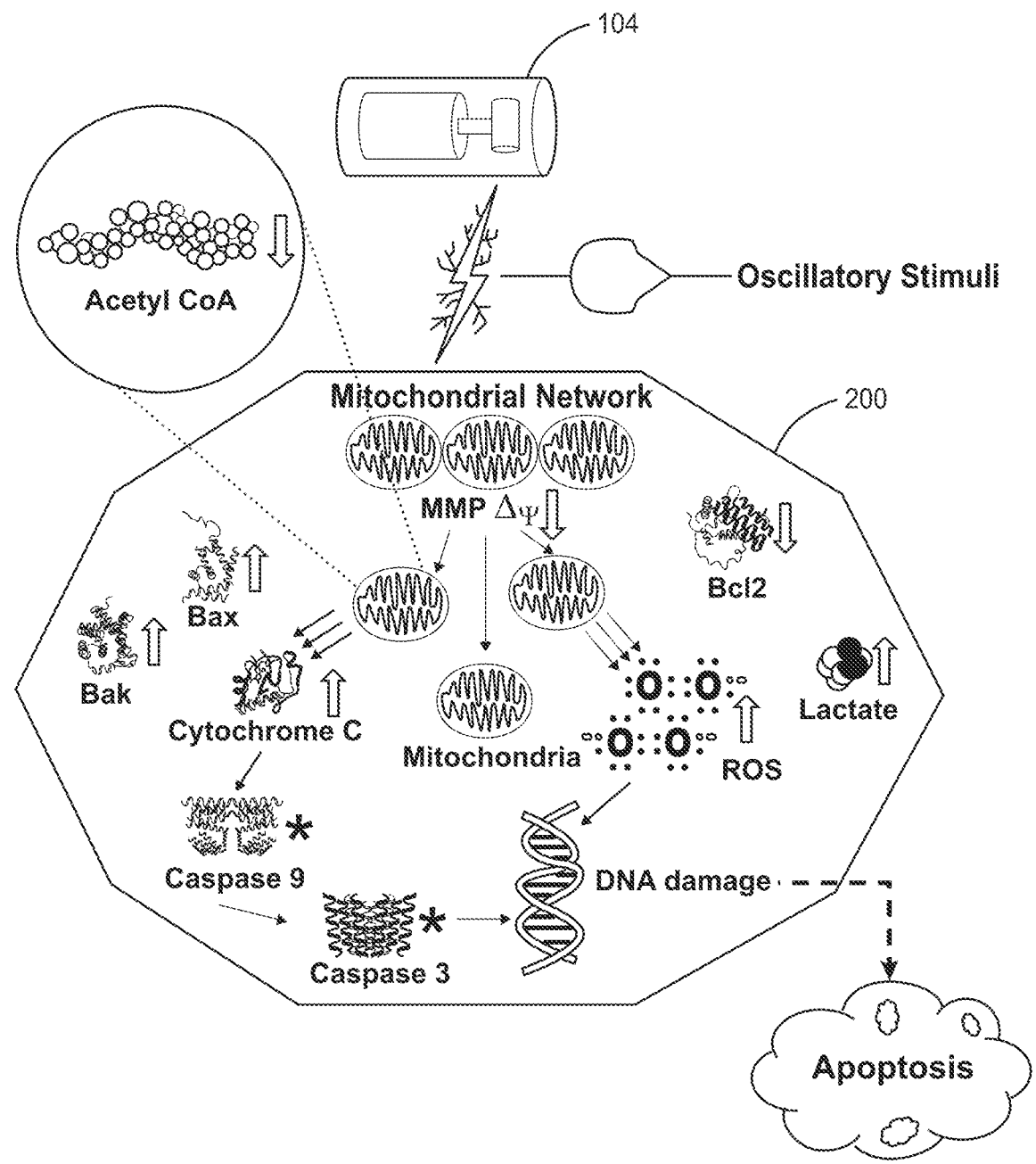
FIG. 2 schematically illustrates the interaction between the system of FIG. 1 and mitochondrial function of a cell.

FIG. 2 schematically illustrates interaction between the system 100, here represented by an example microstimulator 104, and mitochondrial function of an example GBM cell 200. The microstimulator 104 (or several such microstimulators, as discussed above) generates OMFs that decrease mitochondrial glucose oxidation in the tricarboxylic acid (TCA) cycle (or "Krebs cycle") via the production of [1,2-$^{13}$C]acetyl-CoA, increase metabolic flux of glycolysis (determined via $^{13}$C enrichment of lactate from $^{1}$H NMR spectrum of the cell extracts), disrupts electron flow in the ETC, increases superoxide, peroxide, and other reactive oxygen species generation, opens the MPTP and activates caspase-3-mediated or an alternate apoptotic pathway in GBM cells.

In particular, the system 100 causes one or more stimulators 104 to generate a rapidly changing magnetic field, which in turn disrupts electron flow in the cells 200 present in the tissue exposed to the magnetic field. As schematically illustrated in FIG. 2, the system 100 creates electrical perturbation of mitochondria, which are intracellular energy-producing components, and generates localized release of harmful chemicals (reactive oxygen species and cytochrome C) within cells with impaired mitochondrial function including, but not limited to, cancer cells. This localized release of harmful chemicals triggers apoptosis, or a molecular cell death process.

More particularly, cancer cells demand more energy in the form of adenosine triphosphate (ATP) produced by mitochondria due to uncontrolled cell divisions, and thus are under heightened stress. The system generates the OMF which in turn produces rapidly fluctuating or sustained depolarizations of the mitochondrial membrane potential (MMP) in the tissue. This process leads to fragmentation of mitochondrial networks and disruption of ATP generating proton flux/electron transport in individual mitochondria. Further, this process cases leakage of cytochrome C and reactive oxygen species (ROS) which depolarize the MMP further and cause degradation of mitochondria. These events collectively trigger the molecular pathway that leads to DNA damage and apoptosis, or another mechanism of cell death, in the cancer cells. Because normal cells (e.g., healthy cells) have a larger amount of mitochondria, have lower demand for ATP, and are not under stress, disruption of electron flow and small amount of ROS formation and MMP depolarization does not trigger apoptosis, or another mechanism of cell death, in normal cells. The lack of apoptosis, or another mechanism of cell death, might also be due to triggering of antioxidant mechanisms that counteract ROS increase.

During several tests discussed below, the system 100 in one implementation generated oscillating magnetic fields which, when applied to GBM cells, caused the breakdown of mitochondrial networks, disintegration of mitochondria due to MMP depolarization, and a decrease in Krebs cycle metabolites. The system 100 in this implementation included a single microstimulator with a neodymium magnet magnetized at 1.48 Tesla. The motor rotated the magnet at approximately 350 Hz. The system 100 generated stimulus pulses of approximately 500 ms duration, with an inter-stimulus interval of 1000 ms (as measured from the beginning of one pulse to the beginning of the next pulse). The microstimulator was placed at a distance of approximately 1 cm from the cells in a slide chamber. Intermittent stimulation with these 500 ms pulses, separated by 1000 ms, was conducted for 60 to 90 minutes.

In some embodiments, the microstimulators 104 oscillate at frequencies in the range of 250 to 350 HZ, to generate OMFs with frequencies of 250-350 Hz. In some cases, the frequencies at which the microstimulators 104 oscillate include subharmonic and superharmonic frequencies. The system 100 can apply OMFs as approximately 250 millisecond pulses with a 50 percent duty cycle (i.e., with an approximately 250 ms ON subcycle or pulse length followed by an approximately 250 ms OFF subcycle or inter-stimulus pulse interval), for example. The system 100 can nest these pulses (or other suitable pulses) in a supercycle that includes an ON period $P_{ON}$ followed by an OFF period $P_{OFF}$. In some implementations, $P_{ON}$ lasts between 5 and 900 seconds, and $P_{OFF}$ lasts between 1 and 300 seconds. Additionally, the system 100 can ramp up the OMF frequency may be ramped up over a 75 to 100 millisecond period to a peak frequency, and subsequently ramped the OMF frequency down from the peak frequency over a 250 millisecond period.

Further, some effects have been shown to occur when the system 100 operates at strengths of ~30 µT to ~200 mT and frequencies ranging from <300 Hz to >9 MHz.

Mitochondria in the experiments outlined below were stained with MitoTracker™ and MitoSOX™ dyes. During repetitive stimulation and real-time imaging of live GBM cells over 10 and 90 minutes, and in fixed cells after 3 hours of stimulation, the fluorescence of these dyes changed, confirming the breakdown of mitochondrial networks, disintegration of mitochondria due to MMP depolarization, and a decrease in Krebs cycle metabolites due to the system 100 generating OMFs. Further, a decrease of approximately 10% in mitochondrial acetyl-CoA formation, combined with a similar increase in lactate (a byproduct of glycolysis in the cytoplasm) was observed using nuclear magnetic resonance spectroscopy.

Figure 3A:
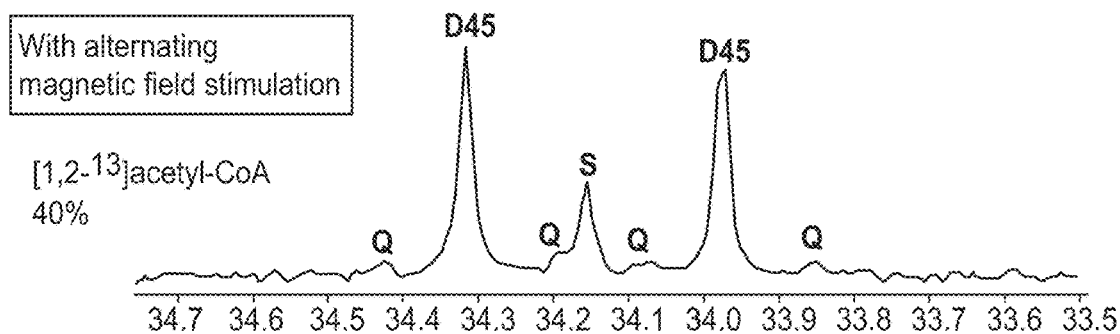
FIGS. 3A and 3B illustrate a $^{13}$C-NMR spectrum of glutamate in a sample of GBM cells to which the system of FIG. 1 applied oscillating magnetic fields (OMFs) for a certain of time, and the $^{13}$C-NMR spectrum of glutamate in a corresponding control sample.
Figure 3B:
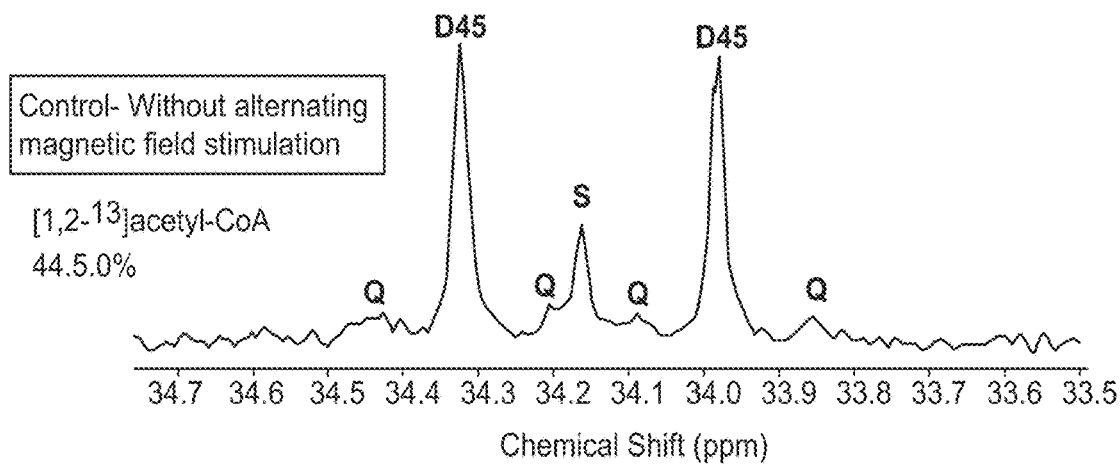

More particularly, FIGS. 3A and 3B illustrate a $^{13}$C-NMR spectrum of glutamate in GBM cells for two samples. In the first instance illustrated in FIG. 3A, the system 100 disrupted electron flow through an oscillating magnetic field in the first sample for three hours. In the second (control) instance illustrated in FIG. 3B, the second sample was not exposed to OMF. As illustrated in FIGS. 3A and 3B, the OMFs generated by the system 100 decreased the synthesis of glucose-derived 13C-acetyl-CoA.

Figure 4A:
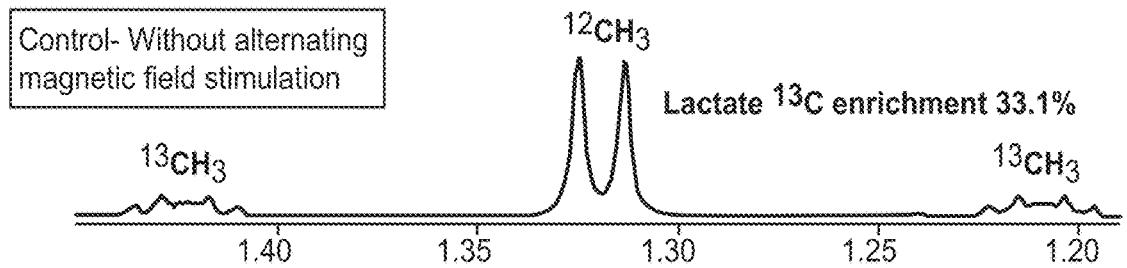
FIGS. 4A and 4B illustrate a $^1$H-NMR spectrum of methyl protons of lactate in a sample of GBM cells to which the system of FIG. 1 applied OMF for a certain of time, and the $^1$H-NMR spectrum of methyl protons of lactate in a corresponding control sample.
Figure 4B:
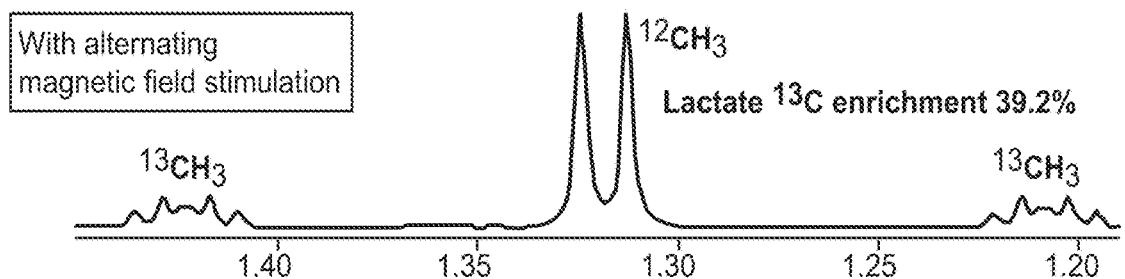

FIGS. 4A and 4B illustrate an $^1$H-NMR spectrum of methyl protons of lactate in GBM cells for two samples. $^{13}$C satellite signals here arise from 13C-1H J-coupling. In the first (control) instance illustrated in FIG. 4A, the first sample was not exposed to OMF generated by the system 100. In the second instance of FIG. 4B, the system 100 generated OMFs in the second sample for three hours, using an oscillating magnetic field. As illustrated in FIG. 4D, the OMFs increased glycolytic flux, which in turn lead to an increased level of 13C enrichment in the tumor lactate pool.

OMF Disrupts Mitochondrial Function and Network

Figure 5A:
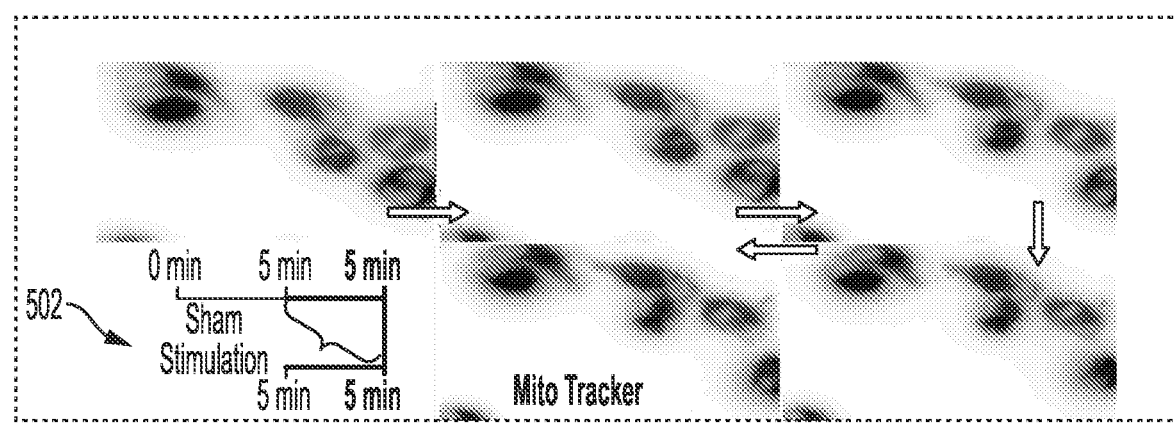
FIGS. 5A-5C illustrates changes in the morphology of mitochondrial networks in GBM cells in response to the OMF which the system of FIG. 1 generated, in particular.
Figure 5B:
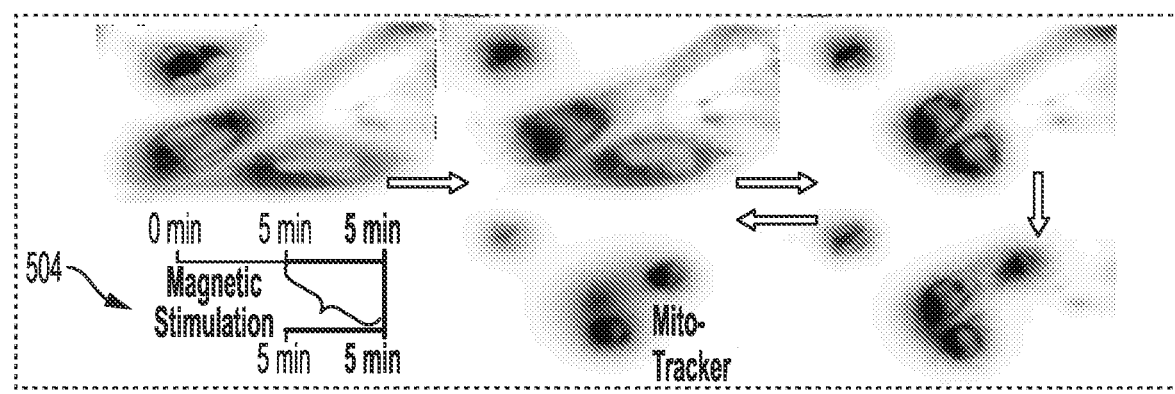
Figure 5C:
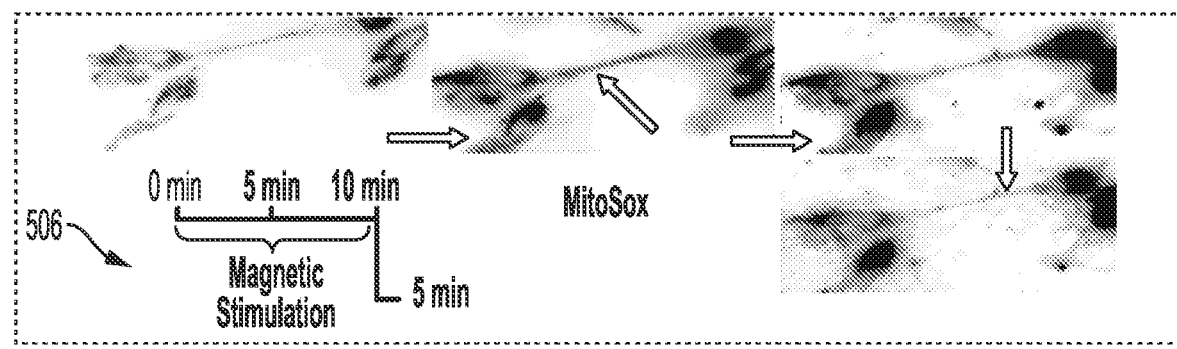

FIGS. 5A-5C illustrate changes in the morphology of mitochondrial networks in GBM cells in response to a rotating magnetic field, which the system 100 generated. In the experiments of FIGS. 5A-5C, a mitochondrial membrane potential probe, MitoTracker™, was used in labeling.

FIGS. 5A-5C provides evidence for a breakdown of the mitochondrial network. In all panels, a non-linear, pixel brightness algorithm was used to allow easier observation of the mitochondrial network. FIGS. 5A and 5B are images of GBM cells, recorded at a magnification of 90×, labeled with MitoTracker™. Images were collected over a 25-min period and at t=10 min a sham or active oncoscillator was turned on for 10 min. No pronounced morphological changes are seen in the cells undergoing sham stimulation (FIG. 5A) Small changes are due to a combination of light flux and singlet oxygen generation due to the fluorescence of MitoTracker™. When the active rotating magnetic field is applied (FIG. 5B) fission of the mitochondrial network was observed, so that after 10 min there are almost no structured clusters of mitochondria seen.

In FIG. 5C, cells were preloaded with the mitochondrial superoxide probe, MitoSOX™, and then subjected to 10-min OMF stimulation. Of note is an increase in the rate of fluorescence signal development compared to the no stimulation control. In the long thin cytosolic strand between two cells, extremely bright mitochondria within a long-range network (arrow, second panel) were observed. However, after 10 min it was observed that the network underwent complete dissipation and there is no recovery after 5 min post-stimulation.

The cells in sample 502 went through sham-stimulation and manifested almost no changes. However, when the system applied 100 a rotating magnetic field to sample 504, fission of mitochondrial networks was observed. After 10 minutes of stimulation, almost no mitochondrial networks or structured clusters were observable.

In sample 506, cells were preloaded with a mitochondrial superoxide probe, MitoSOX™, and were subjected to 10 minutes of magnetic stimulation. In the long thin cytosolic strand between the cells, extremely bright mitochondria were seen within a long-range network (arrow second panel). However, after 10 minutes of stimulation, the network is observed to undergo complete dissipation, with no recovery after 5 minutes, post stimulation.

Figure 6A:
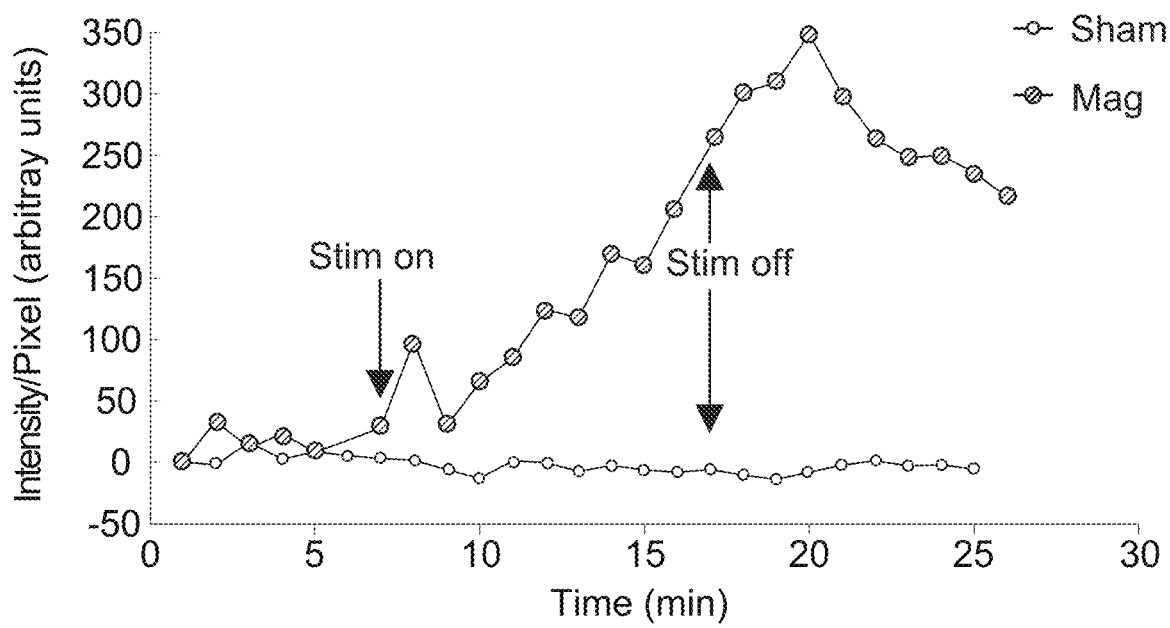
FIGS. 6A and 6B illustrate increased release of the superoxide component of reactive oxygen (ROS) species in response to the OMF generated by the system of FIG. 1.
Figure 6B:
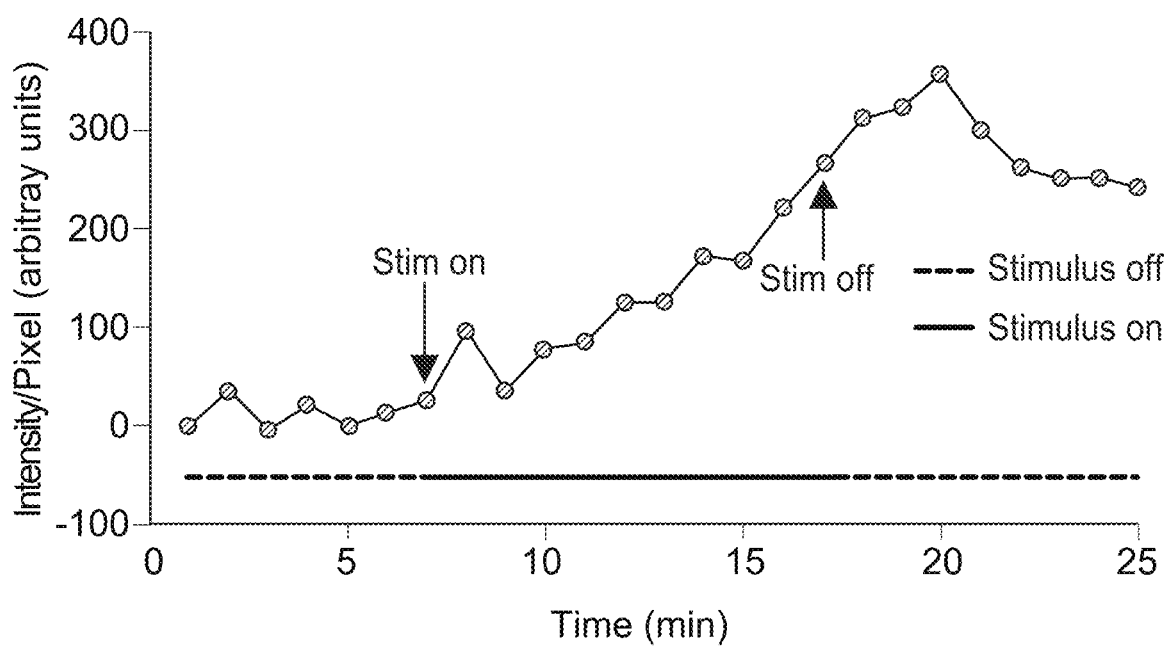

Next, FIGS. 6A and 6B illustrate increased release of the superoxide component of reactive oxygen species in response to a rotating magnetic field generated by the system 100. FIG. 6A illustrates measurements of fluorescence of MitoSOX™ stain for superoxide at different points in time, in relation to activating magnetic or sham stimulation. FIG. 6B illustrates the difference between magnetic and sham stimulation, revealing an increase in superoxide levels in GBM cells following application of stimulation and decrease in superoxide levels in GBM cells following deactivation of the stimulus.

Figure 7A:
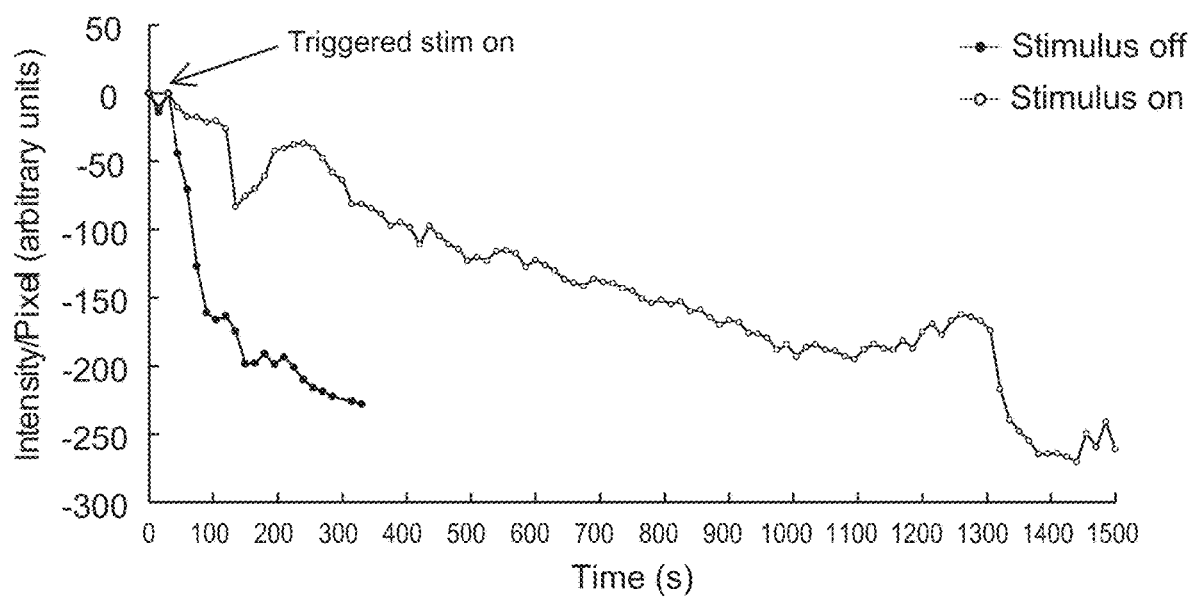
FIGS. 7A and 7B illustrate increase release of the peroxide component of ROS in response to the OMF generated by the system of FIG. 1.
Figure 7B:
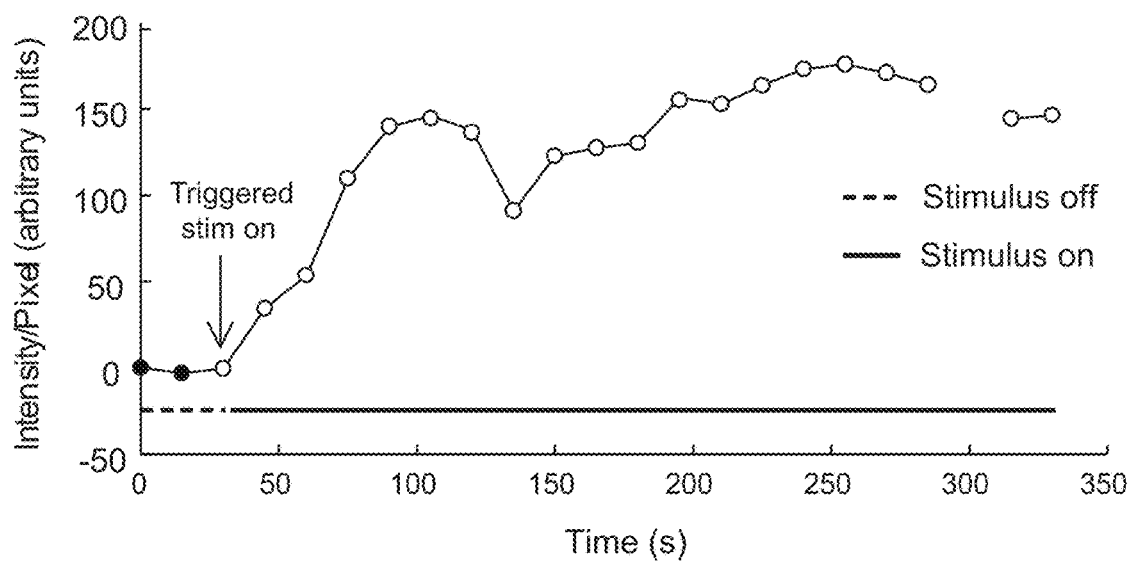

FIGS. 7A and 7B illustrate an increased release of the peroxide component of reactive oxygen specifies in response to a rotating magnetic field generated by the system 100. The graph of FIG. 7A illustrates the fluorescence of an $H_2$DCF-AM probe for peroxide measured at different points in time. To rule out any effects of a static magnetic field, here magnetic stimulation triggered the system 100 rotating the magnet is compared to the magnet being static. The graph of FIG. 7B illustrates the difference in fluorescence between "stimulus on" and "stimulus off" states, revealing an increase in peroxide levels in GBM cells following stimulation by the system 100 using a rotating magnet.

Figure 8:
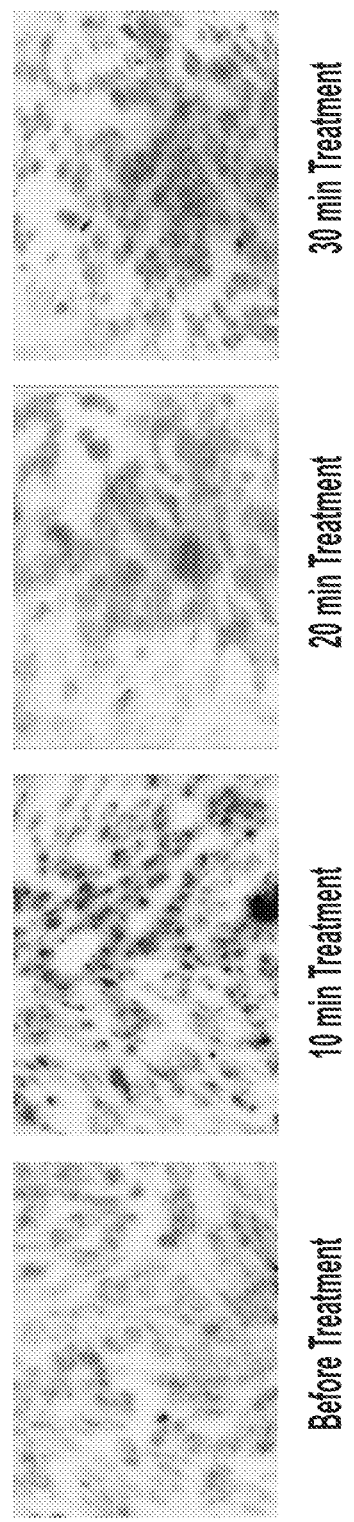
FIG. 8 illustrates increased level of Caspase-3 Activity in response to the to the OMF generated by the system of FIG. 1.

FIG. 8 illustrates an increase in the level of Caspase-3 Activity in response to the OMFs generated by the system 100. In particular, FIG. 8 illustrates that treatment with an oscillating (e.g., rotating) magnetic field causes progressive increase in staining for caspace-3 in GBM cells. The four panels in FIG. 8 illustrate a sample of GBM cells before treatment, after 10 minutes, 20 minutes of treatment, and 30 minutes of treatment. Before OMF stimulation there is no activation of caspase. However, after 10 min of stimulation cells with activated caspase begin to appear. The caspase staining rises progressively until after 30 min most of the cells fluoresce positive for caspase, revealing activation of this enzyme. Each successive panel displays a greater amount of staining for caspace-3, reflecting an increase in the level of activity of this enzyme, which is a final step in the apoptotic pathway. As set out above, the techniques described in this disclosure can apply to various cells having mitochondrial impairment, and are not solely applicable only to cancer cells. Although the examples are drawn to GBM cells, it is expected that the systems and methods described herein are applicable to all types of cancer cells, including other brain cancer cells, carcinomas of the pancreas, breast (including estrogen receptor positive (ER+), ER- and triple negative breast cancer), lung, colon, ovary, esophagus and other cancer cells within other parts of the body of a subject. Additionally, magnetic fields penetrate all magnetically inert materials and tissues equally and therefore, OMF may be used as an effective form of therapy for tumors deep within body structures.

Example Application of OMF in Conjunction with a Chemical Agent

In embodiments and implementations of the oncomagnetic therapy methods and systems described herein, oncomagnetic therapy may be performed in conjunction with the administration of other chemicals, drugs, or radiations to complement the oncomagnetic therapy. In various embodiments, the combination of a chemical, drug, or radiations with OMF therapy potentiates the effect of the oncomagnetic therapy to disrupt mitochondrial function, inducing apoptosis, or another mechanism of cell death, in cancer cells, or otherwise enhancing the oncomagnetic treatment of a tumor. In various embodiments, the chemical includes, but is not limited to, a ketone body (e.g. β-hydroxybutyrate or acetoacetate), or acetate, or free fatty acid (e.g. octanoate, stearic acid, or palmitate), or branched chain amino acid (e.g. leucine, isoleucine or valine), or cryptochrome agonist (e.g. KL001), or MGMT inhibitor (e.g. O 6-benzylguanine), or DNA alkylating agent, or DNA methylating agent may be provided to a region of tissue or cell, tumor, or cancer cells in addition to the oncomagnetic therapy to complement the oncomagnetic therapy. For example, there is evidence that β-hydroxybutyrate (BHB) a well-known ketone body component of the low-carb ketogenic diet, octanoate, stearic acid, or palmitate, commonly found free fatty acids in the circulation, potentiates the anti-cancer effects of OMF. Therefore, embodiments are envisioned that combine the administration of BHB, or acetoacetate, or free fatty acid, or branched chain amino acid, or cryptochrome agonist, or MGMT inhibitor, or DNA alkylating agent, or DNA methylating agent, and OMF as a more effective treatment of cancer compared to OMF alone. It is envisioned that other bodies, chemicals, or treatments may be applied in addition to oncomagnetic therapy to provide treatment to a region of tissue, tumor, or cancer cells.

Descriptions and Examples of Microstimulators

Next, several example implementations of a microstimulator that can operate in the system of FIG. 1, and example implementations of a support platform on which these microstimulator can be mounted, are discussed with reference to FIGS. 9-13.

Figure 9:
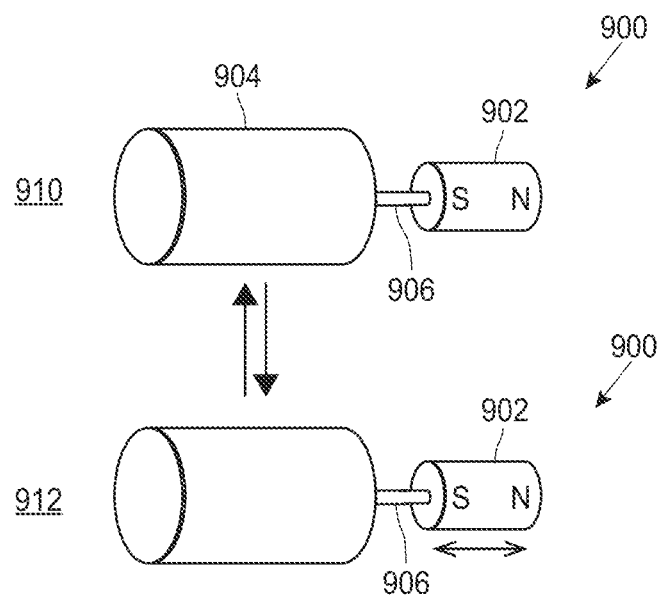
FIG. 9 illustrates a microstimulator that can operate in the system of FIG. 1, according to one example implementation.

Referring first to FIG. 9, an example microstimulator 900 can operate in the system of FIG. 1 as a microstimulator 134-1, 134-2, . . . 134-N. The microstimulator 900 may include a magnet 902 and an electric motor 904. The motor 904 controls motion and position of the magnet 902. The magnet 902 can be affixed to a drive shaft 906 of the motor 904 to allow the motor 904 to oscillate the magnet 902. In this example implementation, oscillation of the magnet 902 includes translation of the magnet along the axis of the drive shaft 906.

FIG. 9 illustrates the stimulator 900 in two operational states: in top half of the figure, the magnet 902 in resting position, with the motor 704 not oscillating the magnet 902; in the bottom half of the figure, the motor 904 is active and oscillates the magnet 902, thereby generating an oscillating, rapidly changing magnetic field about the magnet.

The magnet 902 may have dimensions on the order of centimeters. For example, the magnet 902 can be a cylindrical magnet that is less than one centimeter long, and less than a half a centimeter in diameter. In various implementations, the magnet 902 may be shaped as a disc, a cylinder, a block, a ring, a sphere, or any other suitable solid.

The magnet 902 in various implementations can be permanent magnet, such as a rare earth permanent magnet, a ferrite magnet, an alnico magnet, or any other type of compact magnet. When the magnet 902 is a rare earth magnet, the magnet 902 can be a neodymium magnet, a samarium-cobalt magnet, or a magnetostrictive magnet, as these types of magnets have strong magnetic fields, typically greater than 1.2 Tesla. In other implementations, the magnet 902 may be a small electromagnet, when the requisite high-strength magnetic field as well as the appropriate amount of cooling to prevent heating and melting of the magnet coils can be achieved.

Further, the magnet 902 can be magnetized through thickness, axially, diametrically, north on the outside face, south on the outside face, through circumference, or using any other magnetization polarization. The specific shape and magnetization may determine the position and orientation of the magnet in relation to the desired treatment region or target site, which in turn may determine the type of motor and motion applied to the magnet.

The motor 904 can be a high-speed motor operating at 19,000 RPM or more, for example. The motor 904 of FIG. 9 is a oscillates the magnet translationally, in other embodiments the motor 904 may rotate the magnet 902. The magnet 902 can be a permanent magnet, such that rotation of the magnet 902 produces a rapidly changing magnetic field. Further, the motor 902 can be a variable-speed motor capable of oscillating the magnet 902 faster or slower to adjust the amplitude of the OMF at a target site or volume. More generally, the motor 904 can be a linear DC solenoid, a rotary solenoid, a push-pull solenoid, any brush or brushless motor, or any other kind of compact motor. The motor 904 can require a voltage of 3-12 volts and a current on the order of hundreds of milliamps to operate. Further, the motor 904 can be sufficiently small so that one or more motors 904 can be mounted on the support platform 106 implemented as a wearable cap, a belt, or a brace structure to be worn by or affixed to a subject, a frame attached to parts of a bed, chair, etc.

Figure 10:
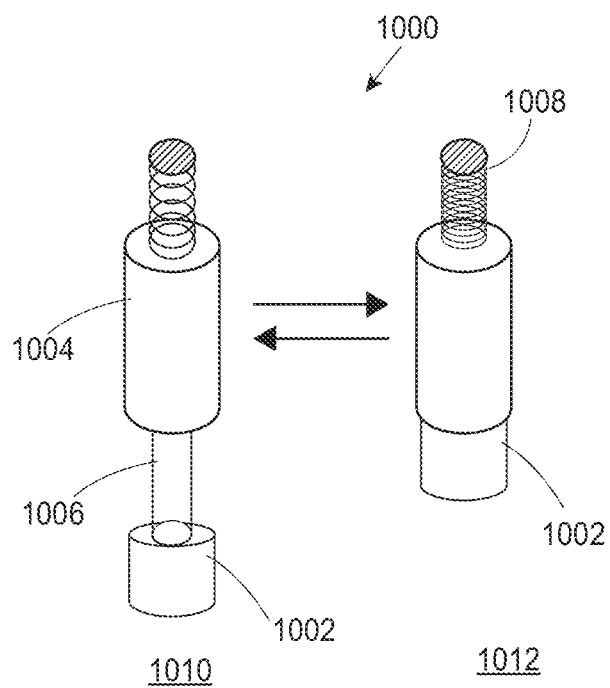
FIG. 10 illustrates another microstimulator that can operate in the system of FIG. 1, according to one example implementation.

FIG. 10 illustrates another example embodiment of a microstimulator that can operate in the system 100 of FIG. 1 as a microstimulator 104. The microstimulator 1000 includes a magnet 1002 attached to a rod shaft 1006 of a push/pull electric motor 1004 which can oscillate the magnet 1002 longitudinally rather. The microstimulator 1000 optionally can include a biasing spring 1008 to drive the magnet 1002 in the direction opposite to that communicated by the motor 1004. The magnet 1002 can be a permanent magnet similar to the magnet 902 discussed above. The push/pull electric motor 1004 can oscillate the magnet 1002 at 19,000 RPM, for example, to generate a rapidly changing magnetic field. For clarity, the microstimulator 1000 is illustrated in two operational states between the microstimulator 1000 transitions, state 1010 (in which the magnet 1002 is in the extended position relative to the motor 1004), and state 1012 (in which the magnet 1002 is in the compressed position relative to the motor 1004).

The two embodiments 900 and 1000 of FIGS. 9 and 10 are non-encompassing and are provided clarity. Accordingly, it will be understood that any other motor and magnet configuration also may be used to alter electron flow through an oscillating magnetic field.

The microstimulators 900, 1000 may be attached to the support platform 106 that can be a wearable apparatus such as a cap, helmet, belt, brace, etc. The support platform 106 also can be implemented as a portable grid, and the microstimulators 900, 1000 can be attached to the grid according to various configurations. The microstimulators 900, 1000 may be attached to such platform by means of hook and loop mechanisms, latching mechanisms, buttons or snaps, adhesive tapes, soluble adhesives, elastic pockets or cushions, or any other suitable attachment mechanism. The support platform 106 can be made of cloth or soft plastic, hard plastic, metal, or any other material for positioning the microstimulators 900, 1000 at desired locations in relation to a target site or volume. The microstimulators 900, 1000 also may also be integrated into the end of an intraoperative probe, as discussed above.

Descriptions and Examples of OMF Apparatus

Figure 11:
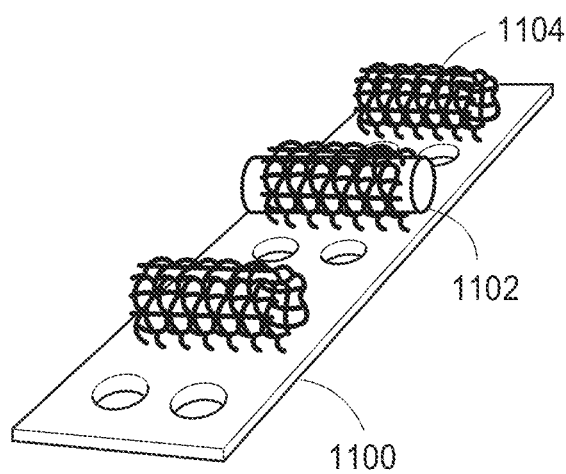
FIG. 11 illustrates an example flexible strap on which one or several microstimulators of FIG. 9 or 10 can be mounted.
Figure 12:
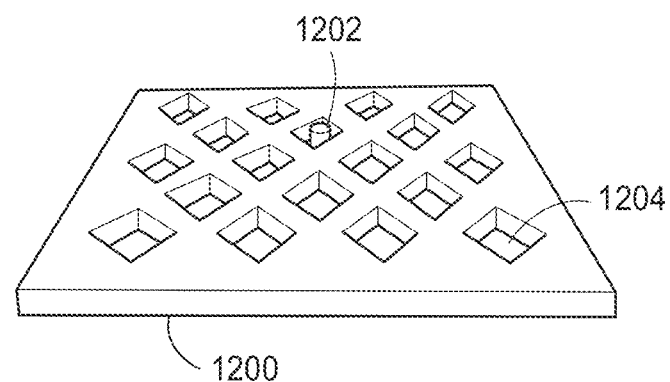
FIG. 12 illustrates an example insert on which one or several microstimulators of FIG. 9 or 10 can be mounted.
Figure 13:
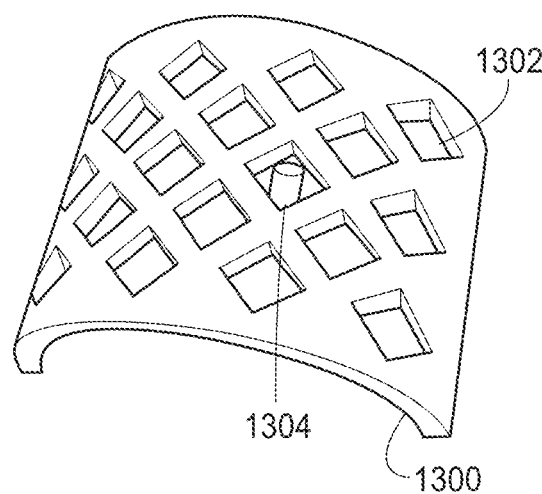
FIG. 13 illustrates an example frame on which one or several microstimulators of FIG. 9 or 10 can be mounted.

FIGS. 11-13 illustrate three example implementations of the support platform 106 that may house or position microstimulators. In particular, FIG. 11 illustrates a flexible strap 1100 with a microstimulator 1102 inserted into a pocket 1104. The flexible strap 1100 may be integrated into a helmet, brace, belt, or other wearable apparatus or any apparatus to position the microstimulator 1102 at a desired position relative to a patient. FIG. 12 illustrates a flat plastic insert 1200 with an attached microstimulator 1202 placed inside cushions 1204. FIG. 13 illustrates a curved, light, non-magnetic metal or plastic frame 1300 with an attached microstimulator 1304 integrated into bridge frames or brackets 1302. The microstimulators 1102, 1202, and 1304 can be implemented as the microstimulator 900, 1000, or another suitable type of a microstimulator.

In general, the support platforms 1100, 1200, and 13003 can support any number of microstimulators may be attached to any apparatus able to position the microstimulators at desired positions relative to a patient, that enable the delivery of a magnetic field to a target site or volume.

Referring to FIGS. 11-13, one or multiple microstimulators can be fixed in place near and/or surrounding the target tissue to be treated. In the implementations with multiple microstimulators, any two fixed microstimulators can be separated from each other by at least 2 cm at their magnet ends. Also, in their fixed positions, the long axes of the microstimulators can be oriented at least at a 60 degree angle with respect to each other. Implementations with multiple microstimulators may enable treatment of larger target volumes and/or simultaneous treatment to multiple target sites or volume.

In another implementation, a single microstimulator, a pair of microstimulators, or an array of microstimulators can be mounted on a grid that can slide, swing or rotate into different positions on near and/or surrounding the target tissue to be treated, in accordance with a programmed scanning protocol. Such an embodiment would allow for multiple target volumes to be treated in one session without having to detach and reattach microstimulators, and/or remove the wearable apparatus.

Examples of Performing OMF Treatment on GBM Cells

The following discussion pertains to one example application of the disclosed apparatus and methods, but is not intended to limit the scope of any of the claims thereto.

In an example application, patient-derived GBM (BT-175) cells were grown in high glucose (25 mM) Dulbecco's modified Eagle's medium (DMEM) supplemented with 20% fetal bovine serum (FBS), 2.0 mM glutamine and 1.0 mM pyruvate at 37° C. under humidified air with 5% $CO_2$. Cells were divided into 2 groups, a test group and a sham group each with n=4. The cells were grown until confluency was reached, ~$2.0 \times 10^6$ cells/mL. The cells were starved for glutamine for 24 hour, and the cells were treated with 4.0 mM of [U-$^{13}$C]glutamine (Isotec, Miamisburg, Ohio) in DMEM (supplemented with 20% FBS, and 1.0 mM pyruvate) for the last three hours of the 24 hours. During the final three hours of the 24 hours, oncoscillators 104, (see FIG. 1), according to embodiments described herein, provided the test group (the tissue 140) with OMF, and the sham group was treated similar to the test group but with rotations of non-magnetic rods of the same dimensions as the magnets in the oncoscillators of the test group. After the oncoscillators 104 applied treatment for three hours, the medium (the tissue 140) was removed by aspiration, the cells were washed with PBS buffer, and the cells were harvested in 50% methanol (1.5 mL/dish). The cells and 50% methanol were transferred to centrifuge tubes, and the contents were snap-frozen in liquid nitrogen. The cells were thawed and frozen twice, then the cells were frozen again and stored at −80° C. after which GC-MS analysis were performed.

The OMF oncoscillators 104 were an assembly of N52 grade neodymium permanent magnets encased in 3D-printed Nylon. Twelve plastic tubes were affixed to a wooden frame by 3D-printed holders. The oncoscillators 104 were positioned in opposite directions and placed 3.7 cm art. The control application 120 executed on a programmable microprocessor-based console 102 on an Android operating system. The console 102 was an electronic tablet computer that controlled the oncoscillators 104 via a Bluetooth connection ®. An external battery (9.6V, 2000 mAh) or a 9V power adaptor powered the control console 102. The oncoscillators 104 repeatedly applied the OMF at 200-300 Hz frequencies with on-to-off epochs of 250 or 500 ms duration. The total OMF treatment duration was three hours. The culture plates, with n=4, containing the GBM cells were placed on a plastic plate which was placed on an anti-slip rotating turn table which was mounted on anti-vibration rubber pads. The distance from the base of the plates containing the GBM cells to the center of the oncoscillator magnet was 3.5 cm. The peak to peak amplitude of OMF, at the base of the culture plate, was 3 mT.

Snap-frozen cells were thawed and centrifuged to remove the precipitated proteins and $^{13}$C isotopomer analysis of intracellular metabolites by GC-MS was performed. 50 nmols of standard, sodium 2-oxobutyrate, was added to the cells and the samples were evaporated and derivatized by trimethylsilylation (Tri-Sil HTP, Thermo Scientific). 3 µl of the derivatized solution was injected onto an Agilent 6970 gas chromatograph equipped with a fused silica capillary GC column (30-m length/0.25-mm diameter) and coupled with an Agilent 5973 mass selective detector. Retention times of the metabolites were validated using standards and the measured distributions of carbon isotopomers were corrected for natural abundance of $^{13}$C isotopomer (1.1%).

To observe OMF induced changes in the reductive carboxylation flux of glutamine in the GBM cells, 4 mM of [U-$^{13}$C]glutamine was introduced to the cells during the 3 hours of OMF stimulation. At the end of the 3 hour OMF stimulation, the cells were snap-frozen as described in the methods for GC-MS isotopomer analysis described above. Similarly, a control experiment conducted with sham treatment, instead of OMF, was performed using rotating non-magnetic rods on the sham group.

It was observed that M+5 glutamine metabolized to M+5 α-KG, which was followed by reductive carboxylation generating M+5 citrate through adding a unlabeled carbon by isocitrate dehydrogeneas (IDH2) in the TCA cycle, as shown by the model in FIG. 1, illustrating reductive carboxylation of glutamine metabolism. ATP-citrate lyase (ACL) cleaved citrate in the cytosol to produce M+3 OAA/Mal/Asp. Oxidative glutamine metabolism generated M+4 OAA/mal/asp which produced M+4 citrate through the condensation with unlabeled acetyl-CoA. Cleavage of the M+4 citrate in the cytosol by ACL led to the generation of M+2 OAA/mal/asp. Relatively lower levels of M+4 citrate in both cases indicated that the GBM cells rely on the reductive carboxylation of glutamine more than other healthy cells of the same type of tissue.

Figure 14A:
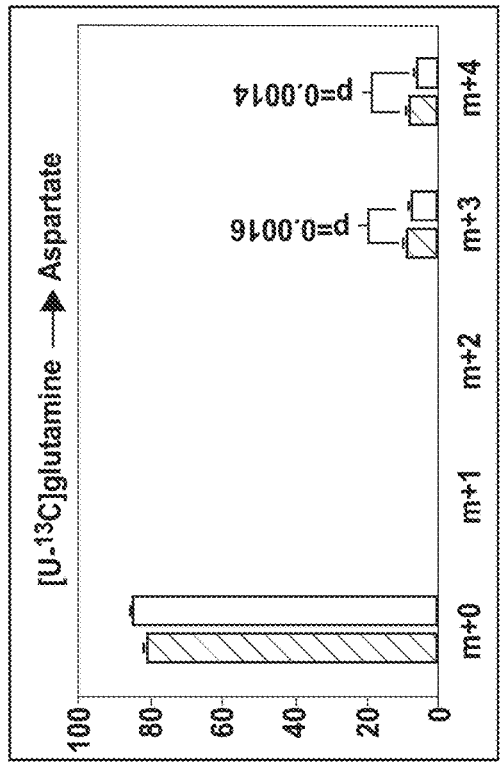
FIGS. 14A through 14D are a set of plots showing mass isotopomer values of various metabolites from GBM cells cultured with [U-$^{13}$C]glutamine with, and without OMF exposure.
Figure 14B:
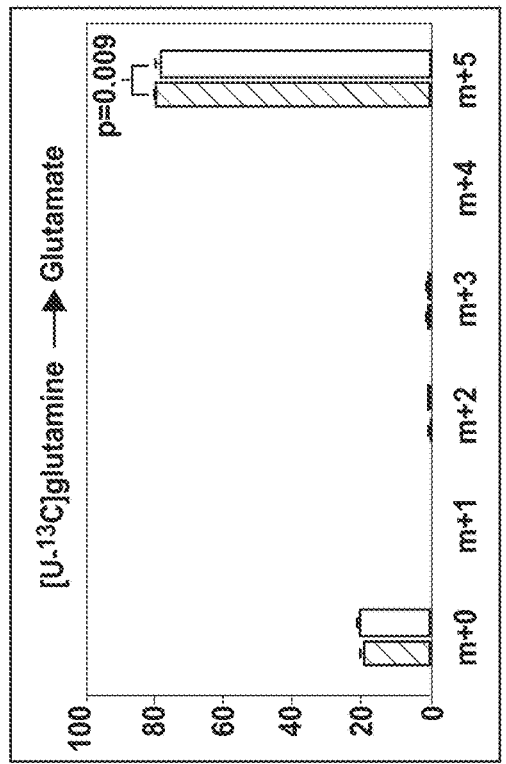
Figure 14C:
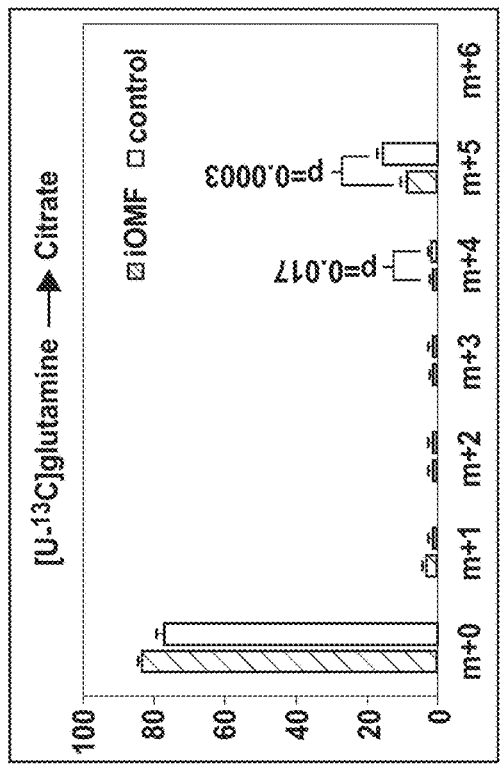
Figure 14D:
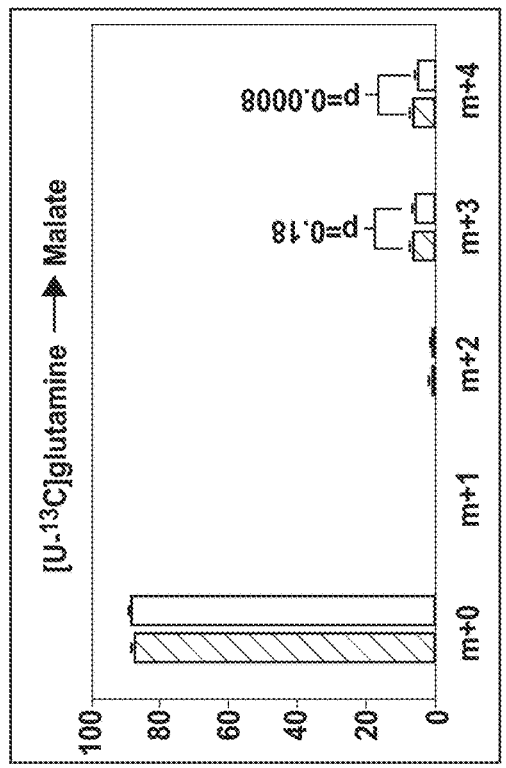

FIG. 14A-14D is a set of plots showing mass isotopomer values of various metabolites from GBM cells cultured with [U-13C]glutamine with, and without OMF exposure. Citrate is shown in FIG. 14A, aspartate is shown in FIG. 14B, malate is shown in FIG. 14C, and glutamate is shown in FIG. 14D. M+5 citrate levels were higher in the GBM cells and the application of OMF reduced the flux through reductive carboxylation pathway, leading 42% less of M+5 citrate isotopomers, compared to control sham-treated GBM cells. The ratio between M5 citrate to M3 malate was 2.42 in the control sham-treated GBM cells, compared to 1.34 in the OM-treated GBM cells, which may be due to the reduced flux through citrate export into cytosol, and cleavage by ACL enzymes due to the application of OMF.

FIG. 14A shows that the OMF exposed GBM cells exhibited a decreased flux through reductive carboxylation of glutamine metabolism. The key enzyme involved in the reductive carboxylation pathway is $NADP^+/NADPH$-dependent IDH1 or IDH2. The mitochondrial $NADPH/NADP^+$ is required to activate reductive carboxylation pathway and silencing either IDH1 (cytosol) or IDH2 (mitochondria) leads to a decrease in the flux through reductive carboxylation pathway.

Figure 15:
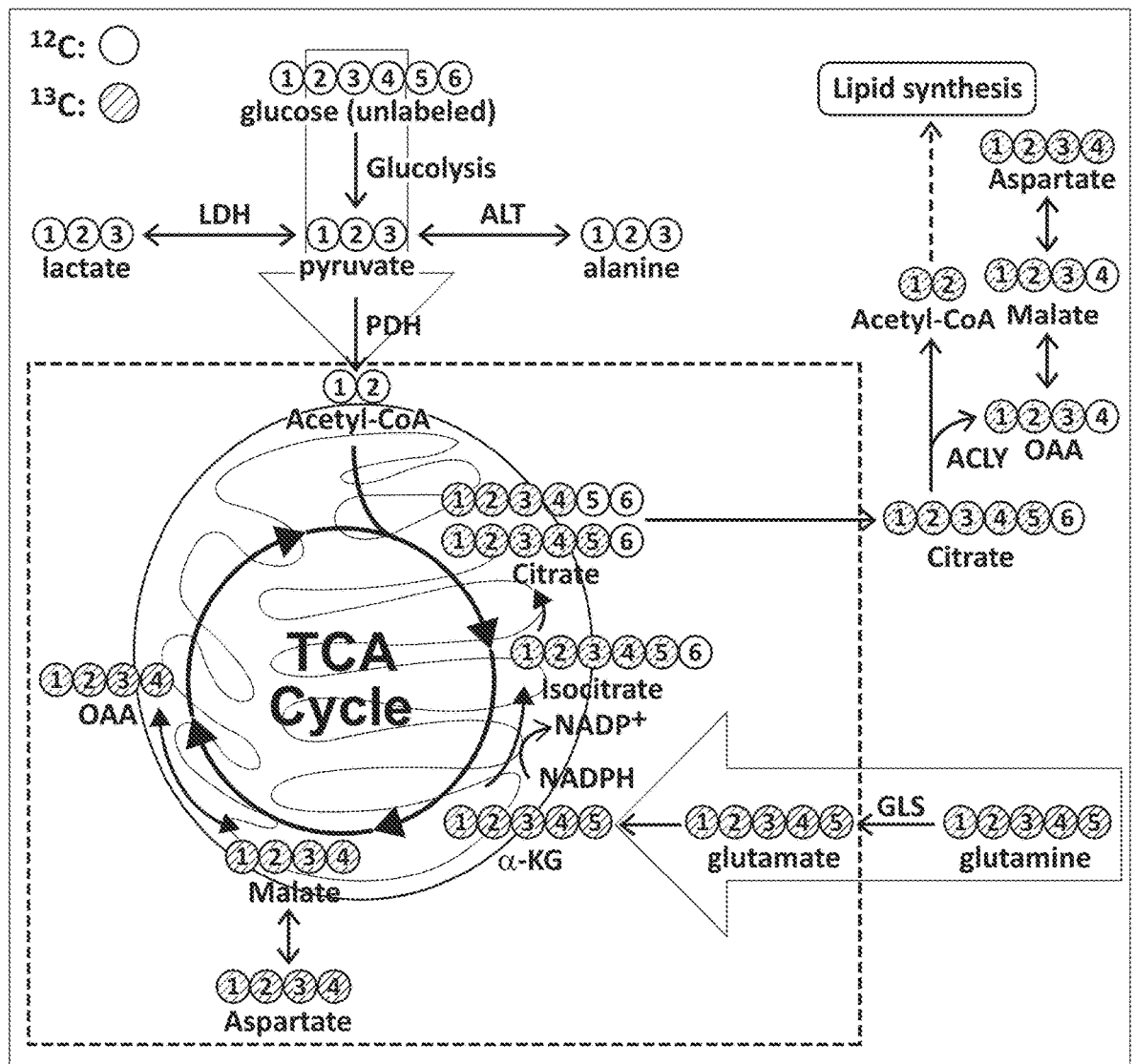
FIG. 15 is a schematic diagram illustrating [U-$^{13}$C] glutamine incubation.

To further explain some of the intracellular effects of applying OMF to a GBM cell, FIG. 15 illustrates details pertaining to the TCA cycle and lipid synthesis in GBM cells. FIG. 15 is a schematic diagram illustrating [U-$^{13}$C] glutamine incubation, an essential process for rapidly dividing cells. 13C labeled glutamine-derived metabolite via reductive carboxylation are used as precursors for lipid synthesis (top right quadrant of FIG. 15). TCA cycle glutamine metabolites are derived from canonical glutamine metabolism, and glucose metabolites are generated through glycolysis from unlabeled glucose metabolism. A decrease in the NADPH-dependent reductive carboxylation flux during the conversion of α-KG to citrate in the TCA cycle (center cycle of FIG. 15) indicate a rapidly fluctuating magnetic field, further resulting in the generation of ROS and causing apoptosis, or another mechanism of cell death, in rapidly dividing cells.

The methods and systems for oncomagnetic therapy described herein for treating GBM cells may disrupt the electron flow in the ETC leading to a shift in the redox potential of $NADPH/NADP^+$. The redox potential shift could decrease the activity of the NADPH-dependent IDH enzyme, causing an attenuation of the glutamine flux through the reductive carboxylation pathway leading to OMF-induced apoptosis, or another mechanism of cell death, of GBM cells.

The methods and systems for oncomagnetic therapy described herein for treating GBM cells may disrupt the electron flow in the ETC leading to a shift in the redox potential of $NADPH/NADP^+$. The redox potential shift could decrease the activity of the NADPH-dependent IDH enzyme, causing an attenuation of the glutamine flux through the reductive carboxylation pathway leading to OMF-induced apoptosis, or another mechanism of cell death, of GBM cells.

Figure 16A:
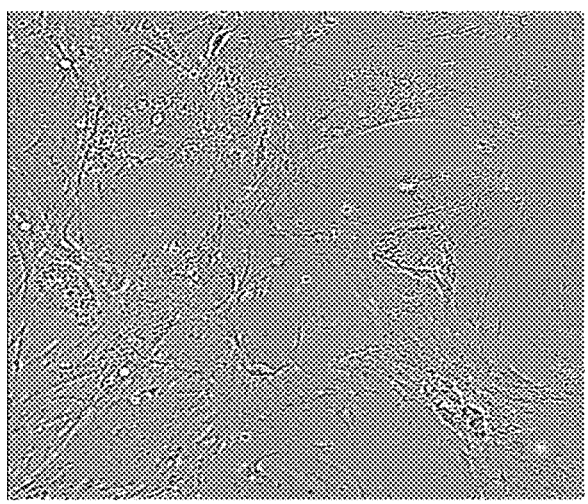
FIGS. 16A and 16B are microscopy images (photomicrographs) of sham-treated (FIG. 16A) and OMF-treated cells (FIG. 16B).
Figure 16B:
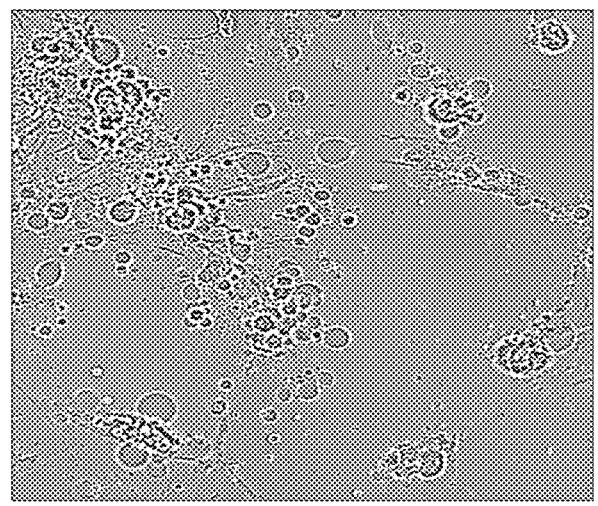

FIGS. 16A and 16B are microscopy images of sham-treated and OMF-treated cells. Blebbing due to cell apoptosis is clearly visible in the OMF-treated cells. Unstained GBM cells were treated with sham or OMF in a temperature-controlled incubator (37° C.) for 2 h. There were noticeable OMF-induced morphological changes showing blebbing due to apoptosis of GBM cells at 2 h during each of three types of stimulation treatment. Nearly all cells in the active treatment condition (PF ~350 ms, TD 250 ms, TI 250 ms and ET 2 h) show blebbing and deformation, suggestive of apoptosis, but no such change in structure is seen in the two control conditions. The transition from normal GBM cell to apoptotic morphology occurred precipitously over a short period of 10-15 min within ~2 h after initiation of stimulation.

The upregulation of antioxidant mechanisms, such as an increase in glutathione, have also been observed in both cancer, and non-cancer cells undergoing during the application of oncomagnetic therapy as described herein. In the cancerous cells the antioxidants are not enough to prevent the effects of the ROS levels caused by the applied OMF. Non-cancerous cells, such as astrocytes, are protected from oxidative damage due to normal ability and functionality of the cell. Therefore, the upregulation of antioxidant mechanisms due to the application of OMFs further protects non-cancerous cells from any ROS-mediated apoptosis, or another mechanism of cell death. Further, if normal, non-cancerous cells are exposed to fluorescent light, the cells usually die after about an hour. Due to the upregulation of antioxidant species, normal cells exposed to OMF fields, as described herein, stay alive longer under the exposure to fluorescent light due to the protection from apoptosis, or another mechanism of cell death, caused by singlet oxygen species. Therefore, oncomagnetic therapy may also provide a means for protecting normal cells under certain conditions (e.g., exposure to certain types of radiation such as fluorescent light) in addition to causing apoptosis, or another mechanism of cell death, in cancer cells.

It has also been shown that the methods described herein may cause other types of cells to undergo apoptosis, or another mechanism of cell death. For example, the methods and systems described herein may be used to kill bacterial cells that do not have mitochondria. In fact, it is envisioned that the methods and systems of applying OMFs described herein may be useful for inducing apoptosis, or another mechanism of cell death, in any cell that utilizes quinones in an energy transport chain or respiratory process.

It should also be understood that while specific frequencies and ranges of frequencies of the OMFs are described herein, other frequencies may be used to target different regions of tissues dependent on the types of tissues and depth of the tissues. Additionally, it should be understood that the harmonic, superharmonic, and subharmonic frequencies of the described frequencies and frequency ranges are envisioned as potential frequencies of the applied OMFs as described herein.

Upon reading this disclosure, those of ordinary skill in the art will appreciate still additional alternative structural and functional designs for disrupting mitochondrial function in cells with mitochondrial impairment through the disclosed principles herein. Thus, while particular embodiments and applications have been illustrated and described, it is to be understood that the disclosed embodiments are not limited to the precise construction and components disclosed herein. Various modifications, changes and variations, which will be apparent to those of ordinary skill in the art, may be made in the arrangement, operation and details of the method and apparatus disclosed herein without departing from the spirit and scope defined in the appended claims.

Descriptions and Examples of a Portable OMF Device

Figure 17:
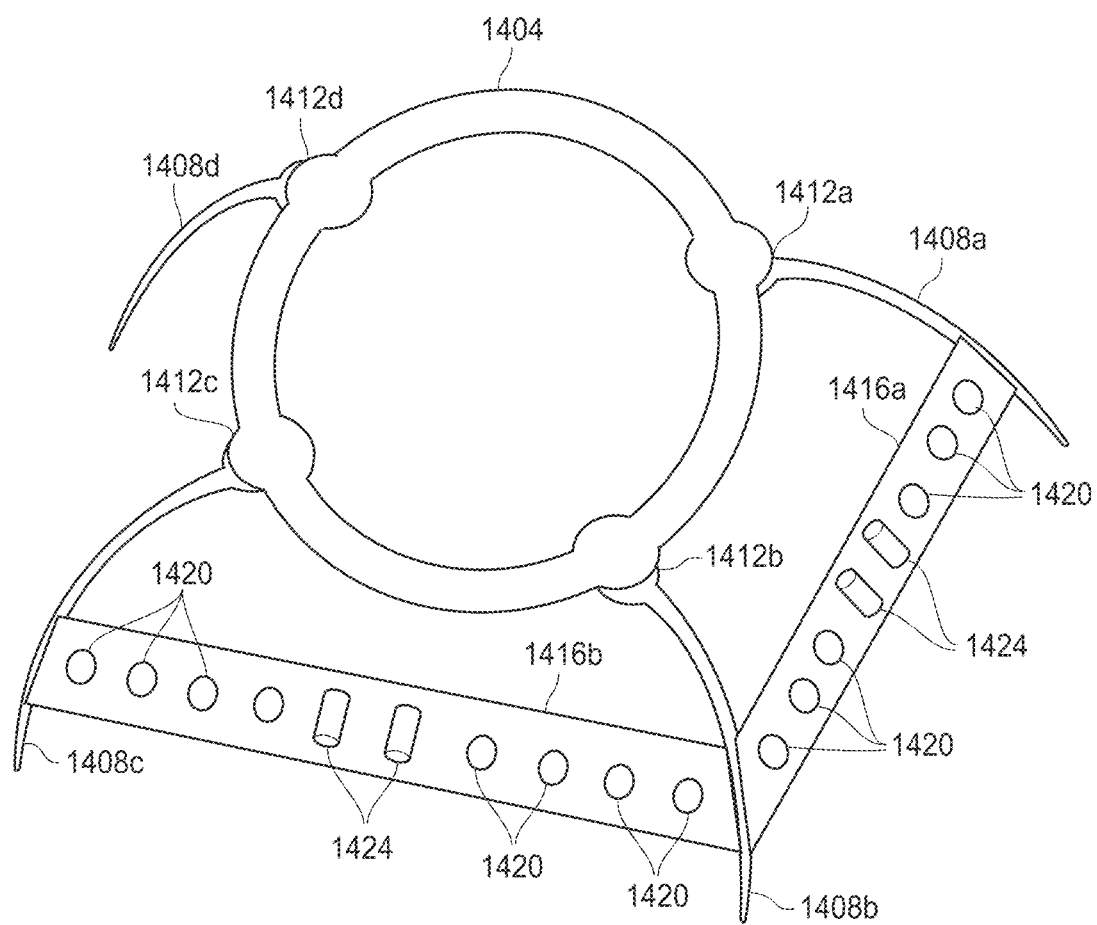
FIG. 17 illustrates an example portable device via which the system can deliver OMF therapy.

Portable OMF devices may allow for the application of OMF therapy in a hospital or clinic in pre- and/or postsurgical treatments, as well as in outpatient care or for ambulatory patient treatment at home. FIG. 17 illustrates an embodiment of a portable OMF device 1400 having an adjustable frame with a central ring 1404 and multiple semi-polygonal antero-posterior adjustable ribs 1408a-1408d that are rotatable and may be fixed in place at desired positions and angles. The portable OMF device 1400 of FIG. 17 may be useful in providing OMF treatment to a patient's head, and the adjustable ribs 1408a-1408d may be positioned to fit on and around a patient's head depending on the size of the patient's head. In embodiments, the adjustable ribs 1408a-1408d may be physically coupled to the central ring 1404 by ball joints 1412a-1412d, as illustrated in FIG. 17. In other embodiments the adjustable ribs 1408a-1408d may be physically coupled to the central ring 1404 by another type of joint, socket, or method allowing for the adjustability of the position and angle of the adjustable ribs 1408a-1408d. It may be desirable to fix the position of the adjustable ribs 1408a-1408d, after adjusting the adjustable ribs 1408a-1408d, for applying OMF treatment to a patient. Therefore, the portable OMF device 1400 may include set screws, bolts, or another physical locking mechanism that may be engaged to lock the adjustable ribs 1408a-1408d in a fixed position, and disengaged to allow for adjusting of the adjustable ribs 1408a-1408d.

The portable OMF device 1400 of FIG. 17 further includes removable plastic inserts 1416a and 1416b that may by clipped onto the adjustable ribs 1408a-1408d and may be configured to span a space between the adjustable ribs 1408a-1408d. The removable plastic inserts 1416a and 1416b contain perforations 1420 by which oncoscillators 1424 may be attached to the removable plastic inserts 1416a and 1416b. The perforations 1420 in the removable plastic inserts 1416a and 1416b enable the attachment the oncoscillators 1424 at any location and in any orientation close to a patient's scalp (i.e., ~0.5 cm over the scalp) using snap-on connectors protruding from the top of each oncoscillator 1424. While described as being attached using snap-on connectors, in embodiments, the oncoscillators 1424 may be attached to the plastic inserts 1416a and 1416b by a hook, Velcro, a temporary adhesive, adhesive tape, a clip, or another type of physical fastener. In embodiments, the plastic inserts 1416a and 1416b may have pockets that the oncoscillators 1424 may be placed in for administering OMF treatment to a region. In addition to spanning spaces between the adjustable ribs 1408a-1408d, removable plastic inserts may also be attached to the central ring 1404 and may span the area inside of the central ring 1404 to provide OMF to a desired region of a patient (e.g., the top of a scalp).

As compared to a head mount or hardness made of plastic or cloth, for example, the device 1400 provides higher durability and increased convenience of rigidly fixing ribs supporting oncoscillators relative to the patient's head.

The following description of is one example application of providing OMF treatment to a patient using the portable OMF device 1400 of FIG. 17, and is meant to be exemplary in nature and is not intended to be limiting of the embodiments disclosed herein, nor exhaustive of all of the embodiments conceivable from the disclosure. In an example application of OMF using the portable OMF device 1400 of FIG. 17, one oncoscillator 1424 may be attached to one of the plastic inserts 1416a and 1416b configured to provide OMFs to the center of a scalp projection of a tumor. Four other oncoscillators 1424 may be attached to plastic inserts (e.g., the plastic inserts 1416a and 1416b) 3 cm from the center of the scalp projection of the tumor, each of the four oncoscillators being away from the center of the scalp projection of the tumor in all four perpendicular directions. Up to 10 other oncoscillators are then positioned, evenly spaced, around the rest of the scalp at 3 cm distances from each other, fanning out from the center to provide OMF treatment coverage to the entire head of a patient.

In embodiments, the portable OMF device 1400 may be a freestanding device supported by a patient's body, or the portable OMF device may be interchangeably attachable to the headboard of a bed, a designated stand, a chair, or another physical support structure. In embodiments, the portable OMF device 1400 may be made of plastic, aluminum, or another non-magnetic material as not to interfere with the application of OMF treatment to a patient. In embodiments, the removable plastic inserts 1416a and 1416b may be physically connected to the adjustable ribs by fasteners, adhesive, clips, being wrapped around the ribs, elastic bands, or another physical connection. While described herein as removable plastic inserts, the removable inserts may be made of other materials such as aluminum, a cloth or fabric, a Velcro strip, an elastic material or fabric, or another non-magnetic material.

In embodiments, a device controller with multiple electrical channels allows simultaneous activation of a plurality of oncoscillators. In the example application of OMF described above, the device controller should have at least 15 electrical channels to control all 15 oncoscillators. The electrical channels may be hardware or software-based communication channels. The controller may include a memory with computer readable instructions stored thereon, designed to apply OMF treatment to a patient using the portable OMF device 1400 of FIG. 17. The controller may include a processor that executes the computer readable instructions to deploy a prescribed stimulus protocol for a specific patient. The controller may be implemented in hardware and/or in an application or software on a Bluetooth-connected device (e.g., a tablet, smart phone, laptop, etc.). In embodiments, the controller may have built-in safeguards, such as face recognition utilizing a camera (e.g., a cell phone camera, laptop camera, etc.) or automatic secure feedback of self-image, timed locking of the device and device function feedback, by secure text, to prevent use by non-intended users, and to prevent misuse (e.g., application of OMF treatment beyond what has been prescribed). Additionally, device function feedback may be further obtained and analyzed by the controller to ensure treatment compliance and proper functioning of the device.

Generating Rotating Magnetic Fields

Generally speaking, a magnetic field at low intensities has pronounced effects on unpaired electrons in molecules participating in chemical reactions and electron transfer processes. Pairing of electrons in bimolecular reactions and electron transfer processes with free radical intermediates, termed as the radical pair mechanism (RPM; not to be confused with rotations per minute), is perturbed by magnetic fields in the millitesla (mT) and microtesla (μT) ranges. This perturbation is due to a quantum mechanical phenomenon in which the intrinsic angular momentum of an electron, i.e. its spin, tends to align itself to be in line with the axis of a magnet and to cause its polarity to be dictated by the orientation of the poles of the magnet. Therefore, if two unpaired electrons that are about to pair up in a chemical reaction are exposed to a magnet, they have a greater tendency to line up in the same orientation as the magnet. The reaction then cannot proceed smoothly because almost all reactions involving radicals require the electron pair that is shared between them to obey a quantum mechanical rule called Pauli's Exclusion Principle. According to this principle, no two electrons in an atomic orbital can be in the same quantum state i.e. have the same spin. Thus, in a chemical reaction involving pairing of electrons, the two electrons in a shared orbital must have spins of opposite orientation. Spins of the same polarity forbid such reactions from taking place. Consequently, in a magnetic field both the product yield and the rate of these reactions can be substantially altered. An electron transfer process can also be similarly affected.

More specifically, during normal interactions between free radicals, the dynamics of RPM consist of electron pairs interconverting between opposite spin (↑,↓) state, termed as the "singlet" configuration and like spin (↑,↑) or (↓,↓) state termed as the "triplet" configuration. Because the local magnetic field of the electron pair in the singlet state cancels out, it is not affected by exposure to an external magnetic field. This cancellation does not happen in the triplet state, and therefore, an external magnetic field whose polarity is not perpendicular to that of the electron pair, influences its alignment. The singlet-triplet interconversion rate of an electron is heavily influenced by the magnetic fields of its neighboring atomic nuclei. These influences are called hyperfine interactions. They in turn affect the dependence of the single-triplet interconversion rate on an externally imposed magnetic field, making it nonlinear, with 3 distinct domains. In the sub-mT magnetic field domain the interconversion rate is higher compared to that in zero magnetic field. An increase in the field strength toward the mT range causes a precipitous decrease in the rate until it saturates at strengths ranging from 1 mT to beyond 1T because of energetic separation of the magnetically influenced triplet states from each other and from the singlet state by a phenomenon called the Zeeman effect. In various aspects, the field strength is 1, 10, 100, 200, 300, 400, 500, 600, 700, 800, 900, 1000 mT (1T). In this domain all electron pairs that are parallel to the external magnetic field remain arrested in the triplet state, reducing the reaction rate and yield or halting electron transfer. If the magnetic field is increased further beyond this domain, the singlet-triplet interconversion rate shows a steep rise.

Observing the effects of a static magnetic field or an oscillating magnetic field induced in electromagnetic coils with a single fixed orientation works well for measuring the entire range of effects on reaction rates and yields involving moving molecules in solution that can freely orient themselves in all directions. This approach is also fully instructive when the observed effect involving molecules in fixed orientations either relies critically on the direction of the magnetic field or requires the perception of its direction. However, it may not be adequate for producing and studying maximal effects of the field on biochemical reactions or electron transfer processes involving molecules in fixed positions and orientations, such as the redox centers in the mitochondrial respiratory chain complexes.

Accordingly, a system that implements the techniques of this disclosure was used to test the hypothesis that, in order to maximally perturb mitochondrial electron transport with a magnetic field, the system would need to generate an OMF by rotating the axis of a magnet.

The main prediction of the above hypothesis was tested by measuring the effects on mitochondrial electron transport with rapidly rotated OMF. The system achieves this by using an oncoscillator of this disclosure. More specifically, a noninvasive system includes a high field strength permanent magnet attached to the shaft of a battery-operated electric motor. The system sweeps through different rotation frequencies by cyclically turning the motor on and off. This technique also allows for an investigation of the possible effects of resonance of the OMF with the periodicities of the electron transfer process and hyperfine interactions.

Figure 18A:
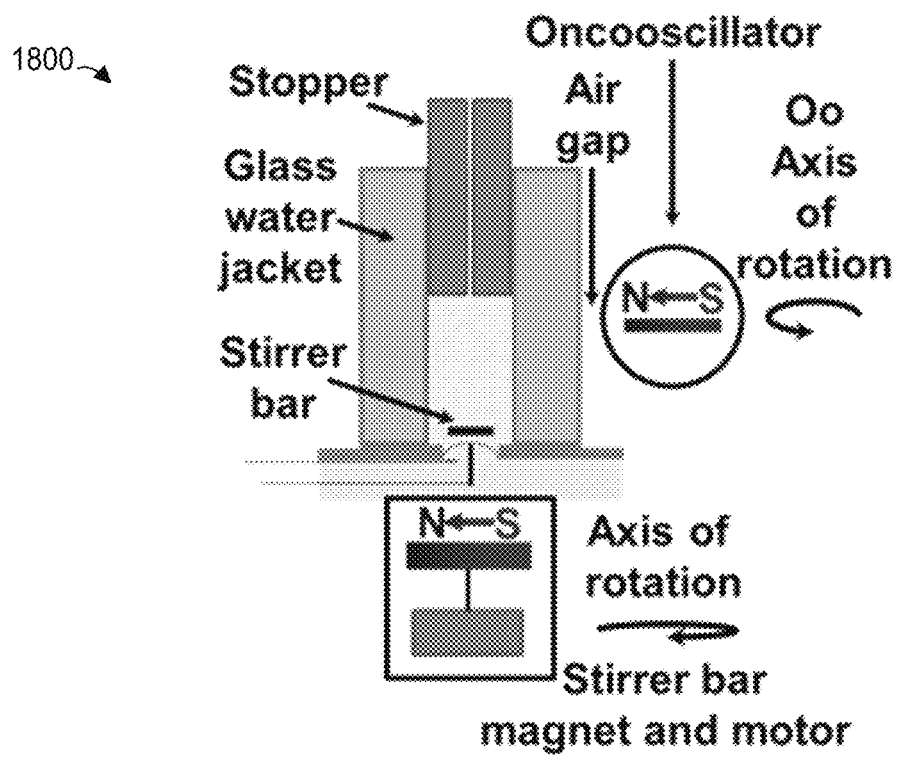
FIG. 18A illustrates an example system that includes an $O_2$-electrode and an oncoscillator that generates OMF by rotating a rare earth magnet.

FIG. 18A illustrates an apparatus 1800 used to perform the procedures outlined above. The apparatus 1800 includes oncoscillator component and generates OMF by rotating an N52 permanent Neodymium rare earth magnet. The oncoscillator assembly is held by a microphone stand, placed next to the water jacketed O2 electrode with a 5 mm air gap, halting vibration transfer. The oncoscillator is positioned so that the center of 1 ml media chamber is exposed to a magnetic field of mT. The rotation of the oncoscillator magnet has a small artifactual effect on the $O_2$ electrode stirrer bar giving rise to an apparent drop or rise in $O_2$ levels.

Figure 18B:
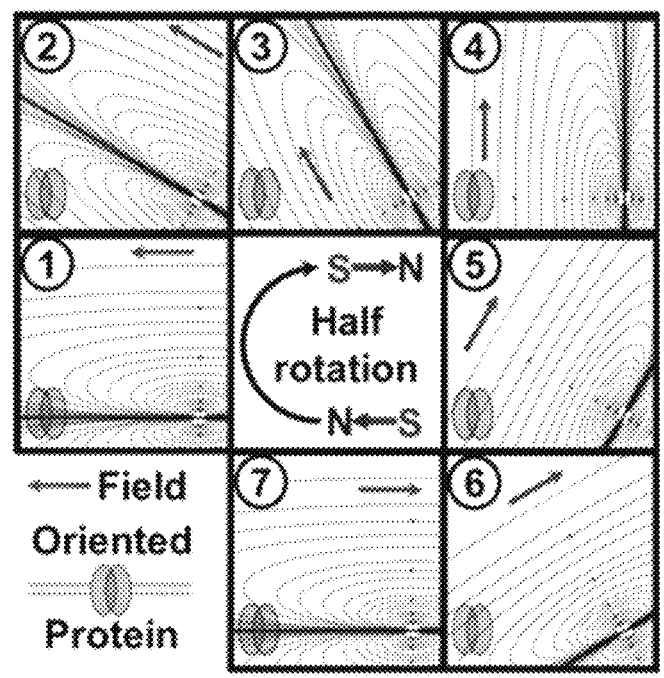
FIG. 18B schematically illustrates changes in the direction of magnetic lines of force with respect to a hypothetical membrane protein with a fixed orientation within the $O_2$ electrode, which the apparatus of FIG. 18A can generate.

FIG. 18B illustrates an idealized visual representation of the changes in the direction in the magnetic lines of force that emanate from the magnet of the oncoscillator of FIG. 18A, with respect to a hypothetical membrane protein with a fixed orientation within the $O_2$ electrode. During a half rotation of the magnet the magnetic field flips from its starting position and the changes in the field orientation are represented in seven steps of 30° increments, (1) to (7). Initially, north is to the left and south to the right (1), but after a quarter turn magnetic north points upward and south points downward (4), and finally after a half-rotation, the field has flipped from the starting position, with south now on the left and north to the right (7). Thus, during a magnet rotation the field will interact with all magnetically susceptible centers in a biological sample flipping polarity from left to right and up to down.

Potentially, the oncoscillator of FIG. 18A can operate in a wide range of rotation frequencies and acceleration/deceleration pulse sequences. Examination of OMF-induced death of primary glioma cells in culture, and the generation of mitochondrial superoxide in these cells with the Mito-SOX' probe, have shown that certain frequency ranges are particularly effective.

The oncoscillator of FIG. 18A can operate efficiently in the range of frequencies between 50 and 350 Hz, with the maximum nominal OMF frequency of ≈280 Hz providing to be most effective. The oncoscillator operates in the ON state for 250 ms and then is in the OFF for the next 250 ms, allowing the oscillations to slow down. During this ON/OFF power cycle, the oncoscillator performs a rapid sweep through increasing frequencies during acceleration and a slower sweep through decreasing frequencies during deceleration. The frequency sweeps may span the cycling rates of electron fluxes associated with different mitochondrial states. Short 5 to 15-min runs of ON/OFF cycles are separated by pauses of similar durations. A range of timings using a variety of cells were used to arrive at these parameters.

Further, to rule out the effects of sound and air pressure waves generated by the oncoscillators, the effects of rotating sham non-magnetic rods also were tested using the same parameters as active magnets. This sham control had no effects in any of the experiments described below. Non-rotated static magnetic field also had no effects.

Rat Liver Mitochondria with Succinate

Figures 18C, 18D:
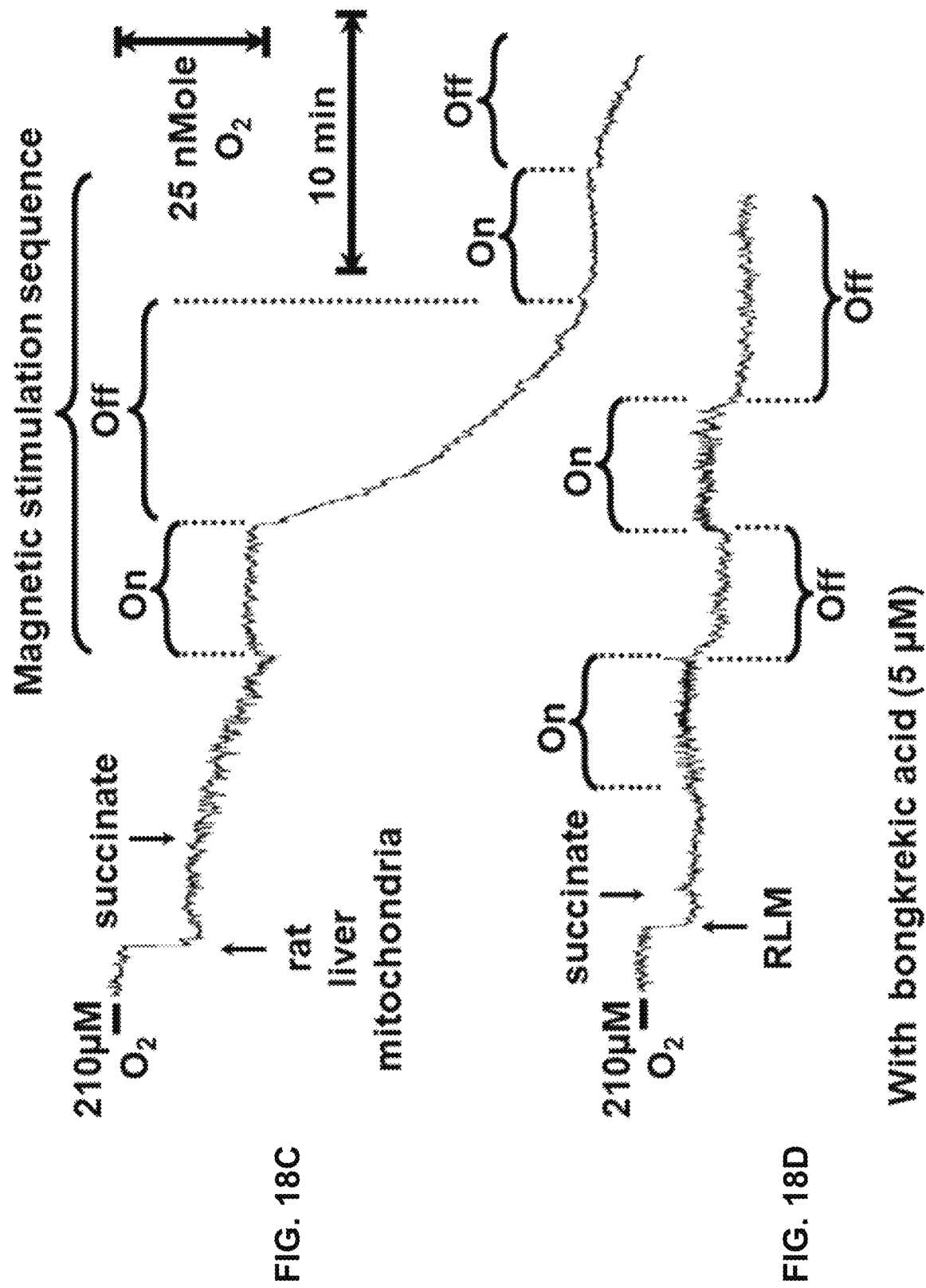
FIG. 18C illustrates a typical $O_2$ electrode trace showing the effects of five minutes of OMF stimulation on rat liver mitochondria metabolizing 5 mM succinate.
FIG. 18D illustrates how bongkrekic acid inhibits mitochondrial 'State 4' flux and completely abolishes the oncoscillator-induced permeability transition.

The effect of OMF on energized rat liver mitochondria (RLM) was examined. FIG. 18C shows a typical $O_2$ electrode trace showing the effects of 5 min of OMF stimulation on RLM metabolizing 5 mM succinate. After the addition of succinate the slow 'State 4' consumption of $O_2$ (≈10 e⁻ s⁻¹) that is typical of RLM oxidizing succinate in the absence of ADP ('State 3') or uncouplers is observed. In state 4 the electron flux from succinate dehydrogenase, the bc1 complex and cytochrome c oxidase is controlled by the presence of a large membrane potential ($\Delta\Psi$) and $\Delta pH$, estimated to be 183 mM and 11 mV, respectively, under similar conditions.

When OMF stimulation is initiated, respiration is completely halted for the whole 5-min OMF stimulation period Immediately following stimulation arrest, a very rapid increase in $O_2$ consumption (initially 86 e- s-1) with the rate falling with time is observed, with an almost first order line shape. After 10 minutes the OMF stimulation was restarted for five minutes, and again resulted in complete inhibition of respiration. After this second stimulation regime ended, respiration restarted at the rate recorded prior to the stimulation cycle. The line shape of the $O_2$ electrode trace after the first stimulation is indicative of mitochondrial membrane permeability transition (MPT). To test if this was the case, the experiment was repeated in the presence of 5 µM bongkrekic acid, which is a specific inhibitor of the adenine nucleotide translocase (ANT), a key component of the mitochondrial permeability transition pore (MPTP), and it halts the MPT at these concentrations. As can be seen in FIG. 18D, bongkrekic acid inhibits mitochondrial 'State 4' flux and completely abolishes the oncoscillator-induced permeability transition.

Additional experiments indicate that OMF stimulation causes both mild inhibition and mild uncoupling of mitochondria in the presence of glutamate/malate or succinate/rotenone. In neither case is permeability transition observed. Ascorbate/N,N,N',N'-tetramethyl-p-phenylenediamine (TMPD) mitochondrial flux appears to be unmodified by OMF stimulation.

Plant Mitochondria and Photosynthesis

Figure 19A:
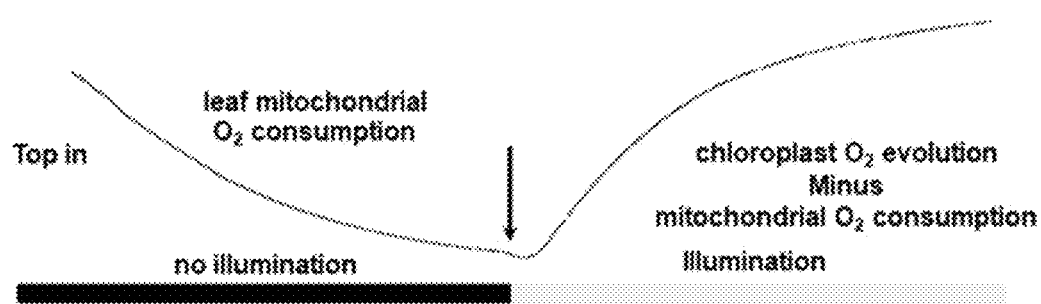
FIG. 19A illustrates a control trace of lemon tree leaf first consuming $O_2$, in the absence of illumination, and then generating $O_2$ via photosynthesis, after illumination.
Figure 19B:
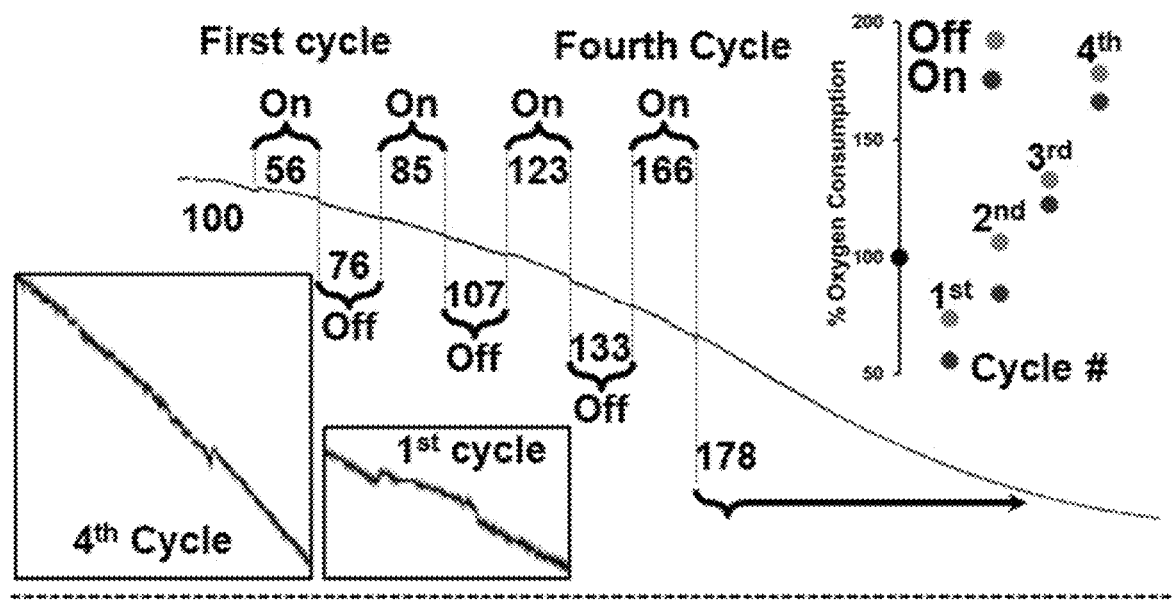
FIG. 19B illustrates the effects of four cycles of OMF stimulation on leaf $O_2$ consumption (particularly that OMF stimulation causes a partial inhibition of plant mitochondrial flux, and also causes mild uncoupling), with the effects of the first and fourth cycles highlighted.
Figure 19C:
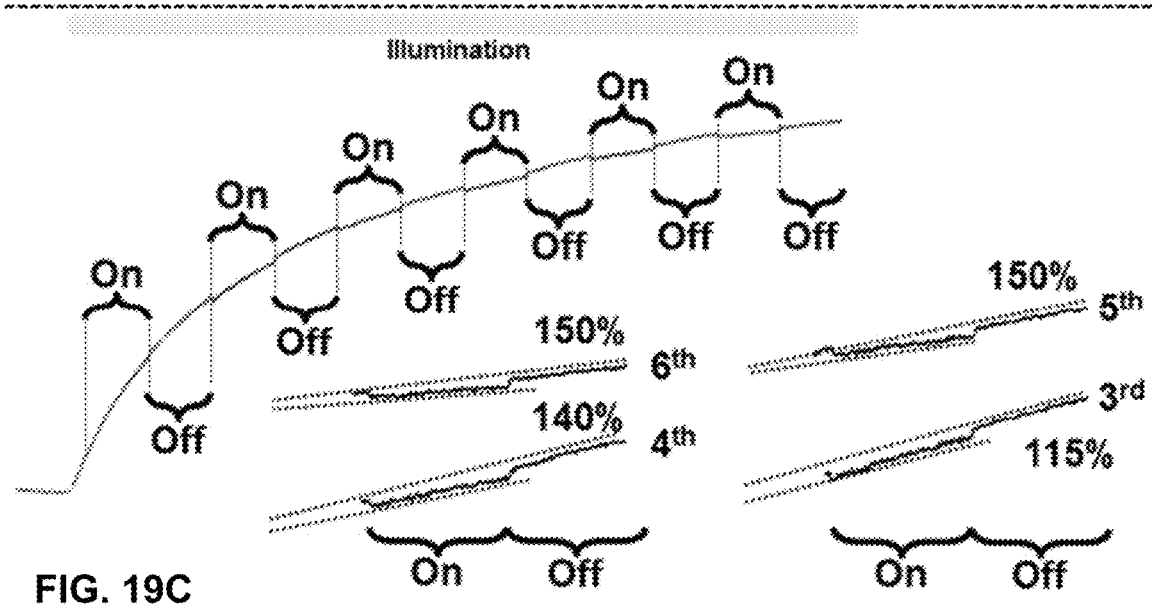
FIG. 19C illustrates the effect of subjecting the leaf to six OMF stimulation five-minute stimulation/pause cycle (particularly that OMF stimulation causes a partial inhibition of the photosynthesis), after three minutes of illumination.

The effect of the oncoscillator of FIG. 18 on a lemon tree leaf, in the absence and presence of illumination, was studied next. FIG. 19A illustrates a control trace of lemon tree leaf first consuming O2, in the absence of illumination, and then generating O2 via photosynthesis, after illumination. In FIG. 19B the effects of 4 cycles of OMF stimulation on leaf O2 consumption can be seen, with the effects of the first and fourth cycles highlighted. The numbers above and below the trace indicate the $O_2$ consumption rate before, during and after an OMF stimulation cycle. During the first 5-min OMF stimulation cycle a drop in the respiration rate and, after cessation of stimulation, an increase that comes to a steady state at 85% of the initial rate can be observed. Subsequent cycles have a similar pattern of inhibition/activation, with the final rate, after four cycles being almost double the initial rate. The best explanation for these observations is that OMF stimulation inhibits electron flux and causes mild uncoupling of the plant mitochondria.

After allowing the $O_2$ concentration to drop to its lowest steady state (<5 µM) a bright light source was used to activate leaf photosynthesis. After three min of illumination the leaf was subjected to six OMF stimulation five min stimulation/pause cycles. Blowups of the traces of the last four cycles are shown with added lines representing $O_2$-generation rates. If the rate of $O_2$ increase during a stimulation cycle is compared with the rate seen immediately afterward, it is clear that $O_2$ evolution is inhibited. In the case of the fifth and sixth cycles the rate after stimulation is 150% of the rate observed during stimulation.

The Mitochondrial Permeability Transition in Cancer Cells and Astrocytes

In FIGS. 20, 21, and 22 representative $O_2$ electrode traces of the effects of OMF stimulation on primary cultures of three fatal brain cancer cell types are presented, namely diffuse intrinsic pontine glioma (DIPG, with the histone H3K27M mutation), meningioma, glioblastoma (GBM), and normal human astrocytes (NHA) as control.

Figure 20A:
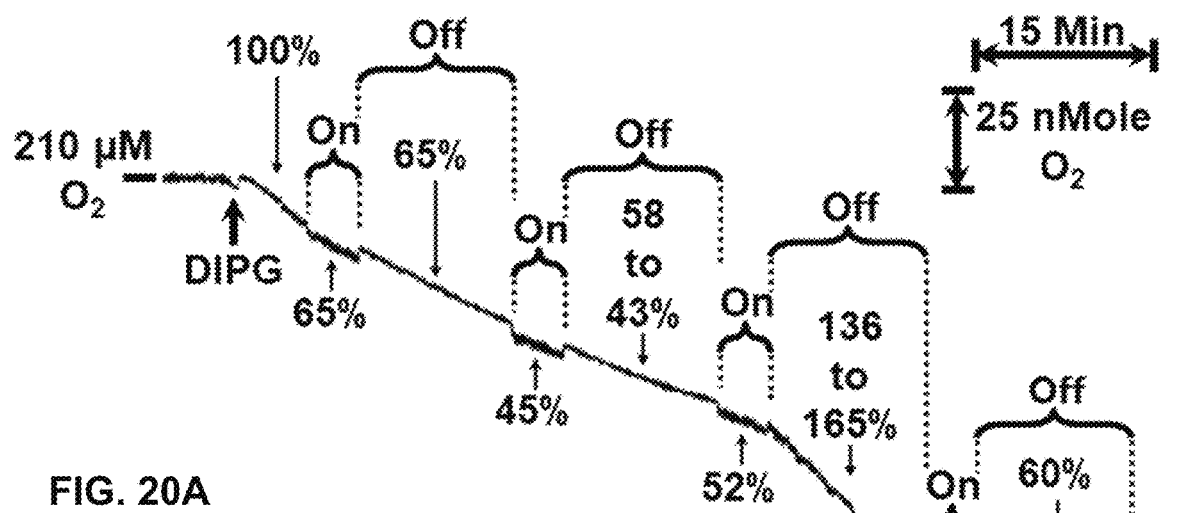
FIG. 20A illustrates the effect of OMF stimulation on $2 \times 10^6$/ml DIPG cells in glucose supplemented PBS, in particular the primary DIPG cells undergoing the permeability transition after repeated cycles of magnetic stimulation, resulting from inhibition of flux and mild uncoupling.

The trace of FIG. 20A shows the effect of OMF stimulation on $2\times10^6$/ml DIPG cells in glucose supplemented phosphate buffered saline (PBS). DIPG cells exhibit a high respiratory flux, typical of the H3K27M phenotype. Before OMF stimulation the $O_2$ consumption rate is $\approx$40 pMol $O_2$ sec$^{-1}$ million cells$^{-1}$, similar to that seen in Chinese hamster ovary cells (100%). During the first five minutes of OMF stimulation cycle, respiration rate falls by a third, and during the first fifteen-minute pause this respiration rate remains at 65% of the initial rate. During the second stimulation cycle, respiration falls to only 45% of the control rate. When the cycle ends the rate rises to 58%, but over the 15-minute pause the flux slows down. During the third stimulation cycle, $O_2$ consumption is held at half the initial rate, but when stimulation ceases a rapid increase in respiration is observed, which increases over the first 10 min and then begins to slow. Finally, the fourth stimulation cycle completely abolishes respiration, and when the stimulation ceases, the rate is at first 60% of the initial rate, and falls off subsequently.

It appears that OMF stimulation slows electron transfer and drives the DIPG cells into a state where they can undergo MPT. Subjecting these cells to OMF stimulation appears to have opposing effects on mitochondrial respiration. On the one hand, stimulation appears to damage the respiratory complexes/Krebs cycle enzymes, slowing electron flux through the respiratory electron transport chain, and on the other hand, it also appears to be causing a mild uncoupling, which allows more rapid electron flux through the respiratory chain, thanks to the removal of product inhibition ($\Delta\Psi\downarrow$).

Figure 20B:
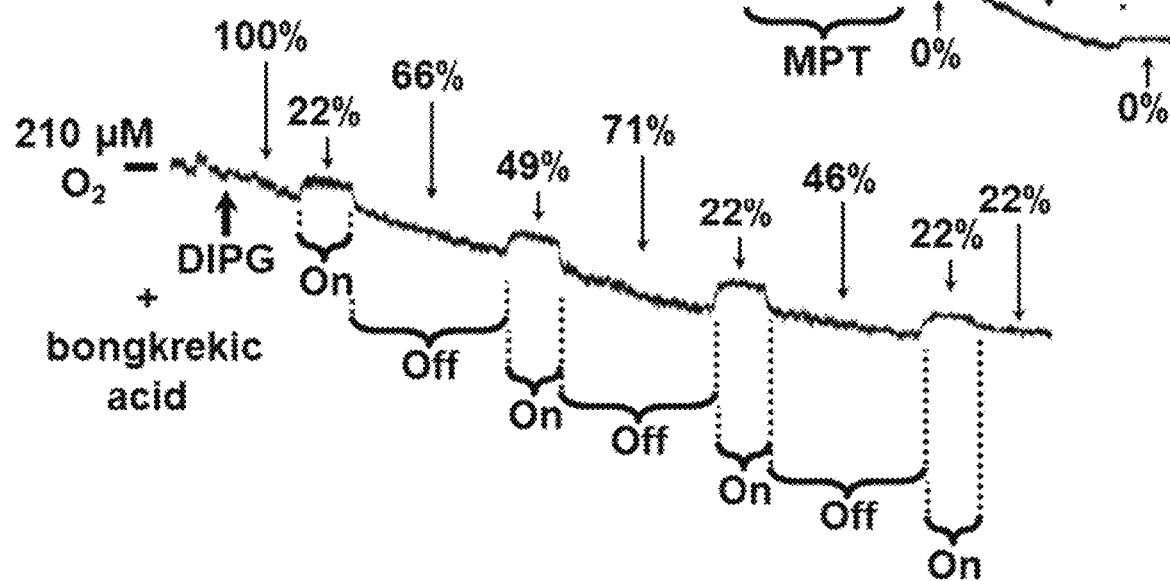
FIG. 20B illustrates the result of re-running the stimulation of FIG. 20A, but with 5 μM of bongkrekic acid blocking the permeability.

The large increase in mitochondrial electron flux that is observed at the end of the third cycle is consistent with a relatively homogenous population of cells, all undergoing MPT simultaneously. To test if this is the correct interpretation of the data, the experiment was rerun, but this time in the presence of 5 µM bongkrekic acid (FIG. 20B). Blocking the ANT with bongkrekic acid slows the steady state mitochondrial electron flux to 55% of that seen in its absence (both rates are normalized to 100% in each panel for ease of interpretation). It can be observed that respiration is slowed during OMF stimulation but there is no increase in rate indicative of the permeability transition.

Figures 21A, 21B:
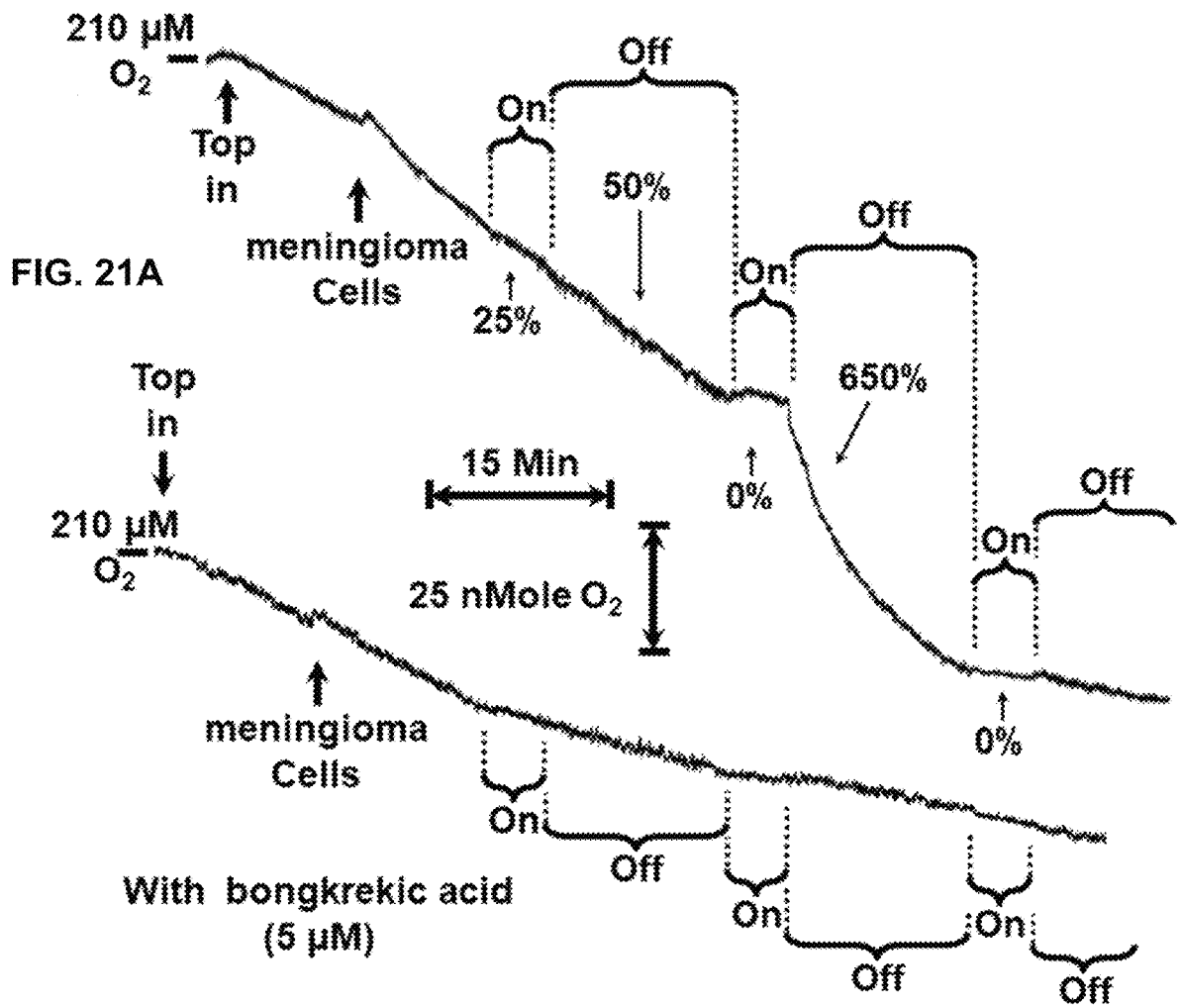
FIG. 21A illustrates the effect of OMF stimulation on high-grade meningioma cells, in particular the mitochondria of primary meningioma cells undergoing the permeability transition after repeated cycles of magnetic stimulation, resulting from inhibition of flux and mild uncoupling.
FIG. 21B illustrates the result of re-running the stimulation of FIG. 20B after pre-treating the cells bongkrekic acid that blocks the permeability.

FIG. 21 follows the format of FIG. 20, but this time primary high-grade meningioma cells were used, showing that OMF stimulation cycles cause MPT. In these cells stimulation causes a 75% drop in the electron flux, and after the end of the first cycle, the cells maintain only half their initial rate (FIG. 21A). During the second cycle of stimulation mitochondrial respiration is completely halted, and as soon as the stimulation stops there is a burst of $O_2$ uptake $\geq 6$ times the initial steady state level. This rate drops in a first order manner. The increase in 02 uptake rate is abolished by pretreating cells with bongkrekic acid, demonstrating that it is due to MPT (FIG. 21B).

Figure 22A:
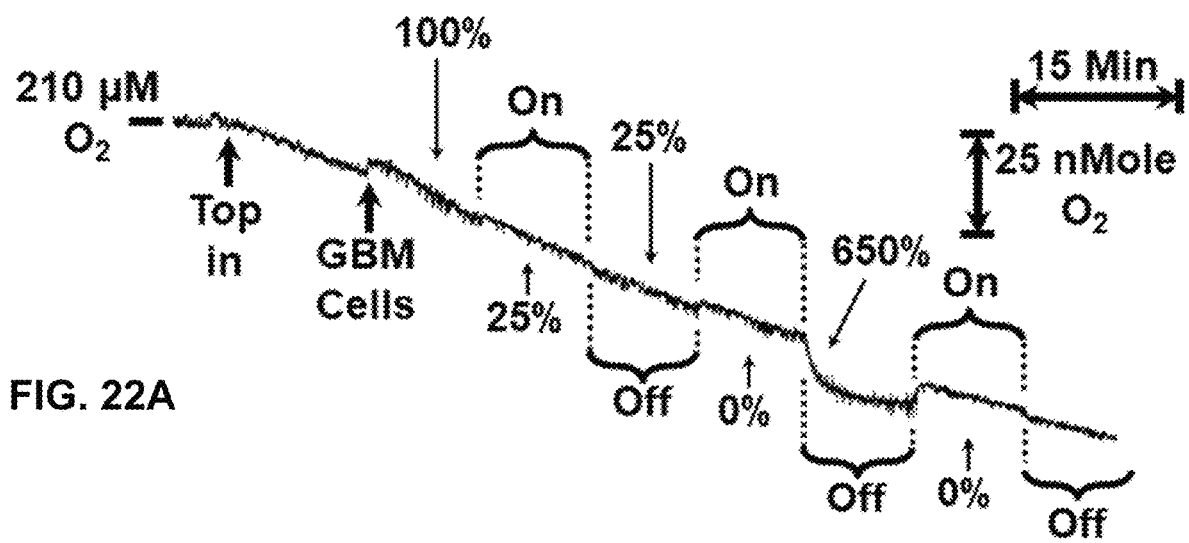
FIG. 22A illustrates the effect of OMF stimulation cycles on the $O_2$ consumption rate of seven different primary GBM cell lines, and in particular the mitochondria of some primary GBM cultured cells undergoing the permeability transition after repeated cycles of magnetic stimulation.

The effect of OMF stimulation cycles on the $O_2$ consumption rate of seven different primary GBM cell lines was observed, and only in one can changes that can be attributed to MPT be observed (FIG. 22A). In cultured GBM156 cells 10-minute stimulation/pause cycles were used to provoke a MPT response. The first stimulation drops the mitochondrial electron flux by 75% and there is no recovery following cessation of stimulation. The second stimulation slows the rate to zero, but immediately after the stimulation stops, a burst of respiration, followed by a slowing, again with a first order line shape, is observed.

In this culture, and the other six primary GBM cultures examined, an inhibition of mitochondrial $O_2$ flux during stimulation always can be seen, and the more cycles that are employed, the more the rate falls. After stimulation, the rates measured are variable, sometimes higher or lower than the initial rate. Addition of carbonyl cyanide-p-trifluoromethoxyphenylhydrazone (FCCP) to GBM cells after 2-3 stimulation cycles did not lead to an increase in $O_2$ consumption, indicating that the rates of $O_2$ consumption reflected that the OMF stimulation had caused both damage and uncoupling of the GBM mitochondria.

Figure 22B:
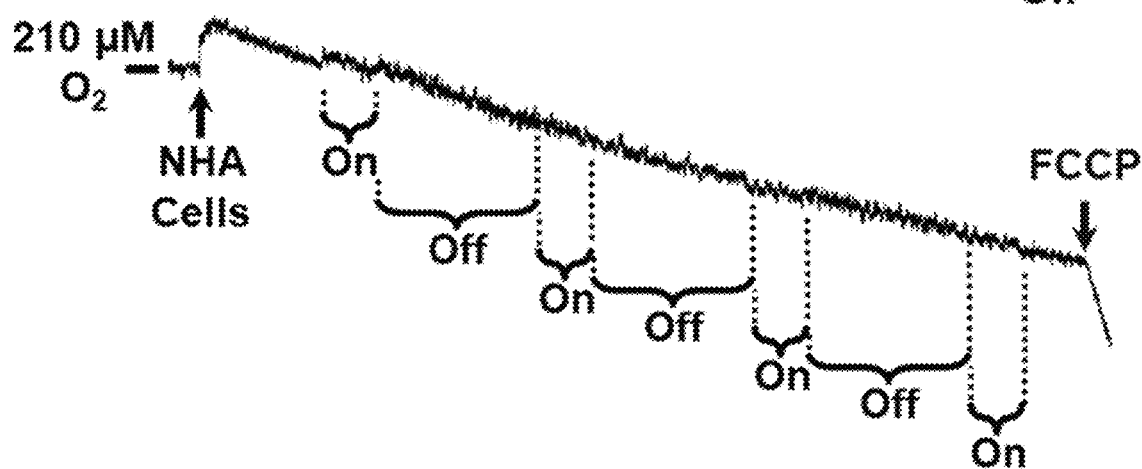
FIG. 22B illustrates a trace in which five-minute stimulation is followed by a fifteen-minute recovery period, and in which four cycles occur before the addition of carbonyl cyanide-p-trifluoromethoxyphenylhydrazone (FCCP) (showing that the mitochondria of normal human astrocytes do not undergo the permeability transition with magnetic stimulation; and the addition of FCCP at the end of the trace showing their mitochondria are undamaged and coupled after oncostimulation).

A variety of combinations and permutations of stimulation/pause cycle durations in NHA were performed, and a typical trace is shown in FIG. 22B. Here, a five-minute stimulation is followed by a 15-min recovery period, and the experiment was run for 4 cycles before adding FCCP. Over the 4 cycles respiration drops by approximately 50%, but the cells maintain their controlled respiration, as is seen by the accelerated rate of $O_2$ consumption after the addition of FCCP.

Theoretical Magnetic Field Effects on the Reaction Rates of Biradical Pairs

Magnetic fields as weak as that of the Earth ($\approx 50$ μT) can alter the kinetics of reactions and such systems are used biologically for navigation in birds. These effects of weak μT and mT-range magnetic fields on chemical reactions are not powerful enough to exert thermodynamic control on biochemical processes but are instead determined by the spin selection rules.

The normal movement of electrons in cytochrome bc1 is briefly considered next. The movements of protons, electrons and quinone radicals and the redox-dependent diodic movement of the Rieske center during the proton translocating Q-cycle of the cytochome bc1 complex is complicated, and the description in this disclosure provides a simplified rather than an in-depth description of the complexity of this reaction.

FIGS. 23A-D schematically illustrate the operation of the second-half of the protonmotive Q-cycle in the bc1 complex, with an emphasis on the generation and reaction of three biradical pairs drawn from six redox centers. At the starting point of the half-cycle (FIG. 23A), a quinone proton/electron receiver is bound to the QN site and the proton/electron donating quinol is bound to the QP site. Along the high potential arm both the Rieske iron-sulfur center and low-spin cytochrome $c_1$ are oxidized. As the two lone electrons of the ferric ions of the Rieske center are spin-coupled, this center is not a radical, but low spin heme ferric iron of cytochrome $c_1$ is a radical. Although the two b-hemes, $b_L$ and bH, are in rapid redox equilibrium, they are presented with the $b_L$ heme as the oxidized, low-spin, radical, and the $b_H$ center in the non-radical ferrous form. The impending electron movements that generate three pairs of biradical pairs are shown with the "e" designation.

Figure 23A:
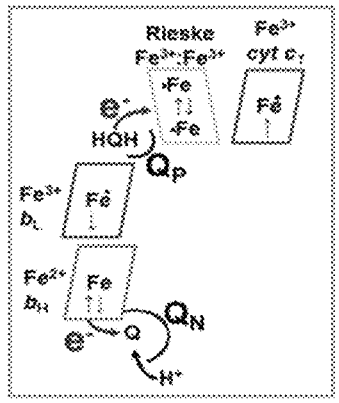
FIGS. 23A-D schematically illustrate the normal movement of electrons in cytochrome bc1, in particular.
Figure 23B:
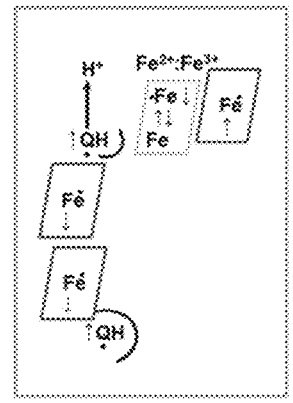

FIG. 23B illustrates the effects of two redox events along the high and low potential arms. The oxidation and deprotonation of the quinol by the Rieske center initially causes the formation of the Rieske:semiquinone biradical, but after movement toward the heme $c_1$, a Rieske:cytochrome $c_1$ biradical pair is generated. After the movement of the Rieske center the semiquinone radical may form a biradical with the ferric heme of $b_L$, prior to the rapid reduction of the latter by the former. A similar biradical ferric-heme:semiquinone pair can arise after the one electron reduction of quinone at the QN site by heme $b_H^{32}$.

Figure 23C:
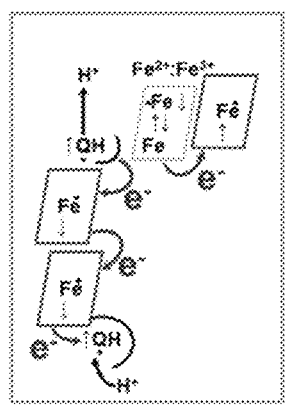
Figure 23D:
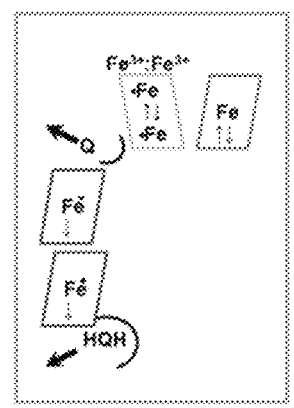

There then follows a series of electron movements collapsing the radical pairs, with the Rieske center reducing cytochrome $c_1$, with and the semiquinone radical at $Q_P$ site reducing the ferric heme of $b_L$, which then passes this electron onto to $b_H$ and then on to the semiquinone at the $Q_N$ site (FIG. 23C). This transfer of charge through the proteolipid and the release/uptake of protons on opposing side of the membrane contribute to the chemiosmotic potential and allows the neutral Q/QH2 molecules to diffuse out of the quinone binding sites (FIG. 23D).

Figure 23E:
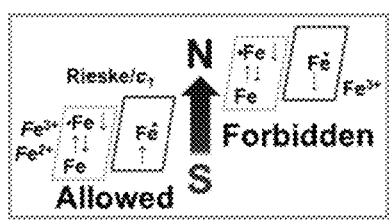
FIG. 23E-G schematically illustrate the effects of rotating magnetic field effects on movement of electrons in cytochrome bc1, in particular.
Figure 23F:
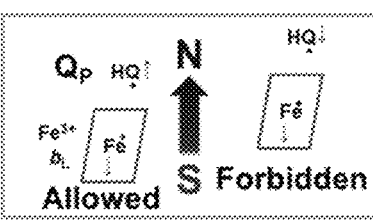
Figure 23G:
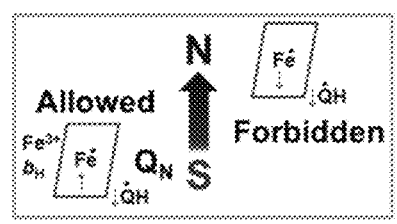

Rotating magnetic field effects on movement of electrons in cytochrome $bc_1$ are briefly considered next. Generally speaking, magnetic fields affect the kinetics of electron transfer between the two centers of biradical pairs. In the case of the redox centers of mitochondrial respiratory complexes, within the time domain for magnetic field inversion used herein, (lowest time $\approx 3$ ms), these centers are fixed and not tumbling or rotating in three dimensions. If the two centers of a biradical pair are fixed the spin states of the centers explore a range of spin orientations, which can be simplified as singlet/spin-allowed, thus reactive ($\downarrow,\uparrow$) and ($\uparrow,\downarrow$), and triplet/spin-forbidden and thus unreactive ($\uparrow,\uparrow$) and ($\downarrow,\downarrow$). At the magnetic field strengths used in this investigation ($\approx 7$ mT) the field would cause unpaired spins to align with the field, converting biradicals in spin-allowed configurations to become spin-forbidden, and hence unreactive. Exposure of respiring mitochondria to the rotating field would cause the spin configurations of the electron pairs in the Rieske:cytochrome $c_1$ biradical (FIG. 23E), the semiquinone:$b_L$ biradical (FIG. 23F) and the semiquinone:$b_H$ biradical (FIG. 23G) to behave like the hands of a pair of synchronized stopwatches, precessing in unison, and forced into unreactive spin states. While in the $\approx 280$ Hz OMF time domain the respiratory complexes are fixed in three-dimensional space, this is not true of dissolved molecular $O_2$ or $O_2$ within the membrane dielectric. $O_2$ is a paramagnetic species with a pair of electrons in the triplet state, $\downarrow O\!=\!O\downarrow$, and liquid $O_2$ streams are attracted to magnets. $O_2$ within an $O_2$ electrode will 'see' the same OMF that acts on the biradical pairs, but $O_2$ is light and completely thermalized by the solution, rotating rapidly on all axes due to constant collisions. This thermalization of the $O_2$ allows bimolecular collisions of semiquinone:heme biradical centers, in spin-forbidden spin states to react with the semiquinone, generating superoxide. It can be observed that OMF generated by oncoscillators produces a rapid rise in superoxide in GBM and other cancer cells. Superoxide is well known to cause the opening of MPTP, accounting for the finding of OMF-induced MPT in this study.

A wide variety of metal/organo-radical pairs are generated in metabolic processes, for instance in photosynthesis (FIG. 19B), which is sensitive to OMF. Therefore, other biochemical reactions involving free radical intermediates and membrane-tethered molecules in fixed orientations could also be sensitive to OMF. In addition to the protonmotive Q-cycle operating at complex III, there is also a Q-cycle utilized in complex I, and this too may be a target of OMF.

Using Mobile Lipids as Metabolic Markers for the Assessment of Treatment-Induced Necrosis in a Recurrent GBM Patient Treated with an OMF-Inducing Device In another aspect, loss of choline and elevation of lipid levels can be used as a metabolite 'fingerprint' to noninvasively assess the response to oncomagnetic treatment described above. In vitro experiments suggest that OMF damage to mitochondria and elevated levels of reactive oxygen species lead to cancer cell death via apoptosis and necrosis, or another mechanism of cell death.

After preclinical studies demonstrated the efficacy of an OMF system discussed above in patient-derived GBM cell cultures and patient-derived xenograft mouse models, a patient with recurrent GBM was treated using the system of this disclosure. Treatment-related changes in the brain and GBM tumor metabolism are discussed next.

Figure 24A:
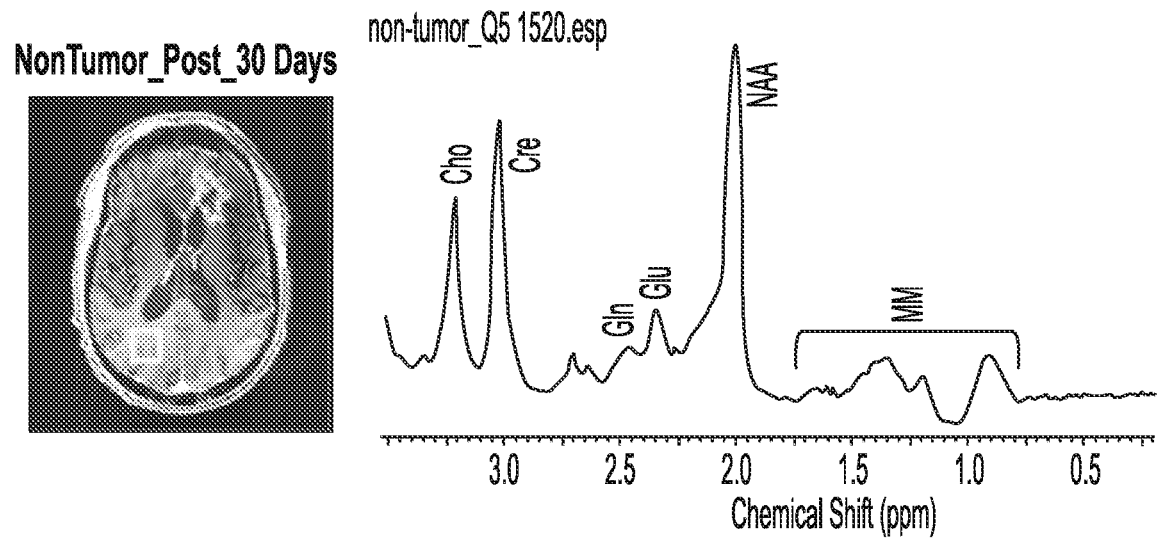
FIG. 24A illustrates an in vivo $^1$H MR spectrum of a non-tumor region of a GBM patient 30 days after initiation of OMF treatment, showing the presence of the neurochemicals NAA, Glu, Gln, Cre, Cho, as well as macromolecules (MM)

The patient is a 53-year old man whose tumor has recurred after having received all standard of care treatment. He was monitored to observe changes in the tumor metabolic profile by in vivo $^1$H magnetic resonance spectroscopy (MRS) using FDA-approved 7T Siemens Terra MRI scanner. $^1$H MRS has been widely used in the diagnostics of glioma patients. Increased choline (Cho) and decreased N-acetylaspartate (NAA) in the tumors positively identify the tumor region from the surrounding brain tissues. $^1$H MRS data of the tumor and non-tumor regions were obtained at two time points (day 30 and 44) during the OMF treatment using semi-adiabatic localization by adiabatic selective refocusing (sLASER) pulse sequence. Both non-tumor and tumor regions showed brain metabolites such as NAA, creatine (Cre), Cho, glutamine (Gln)/glutamate (Glu), and myo-inositol. The levels of these metabolites were low in the tumor region compared to the non-tumor region (FIG. 24A).

Figure 24B:
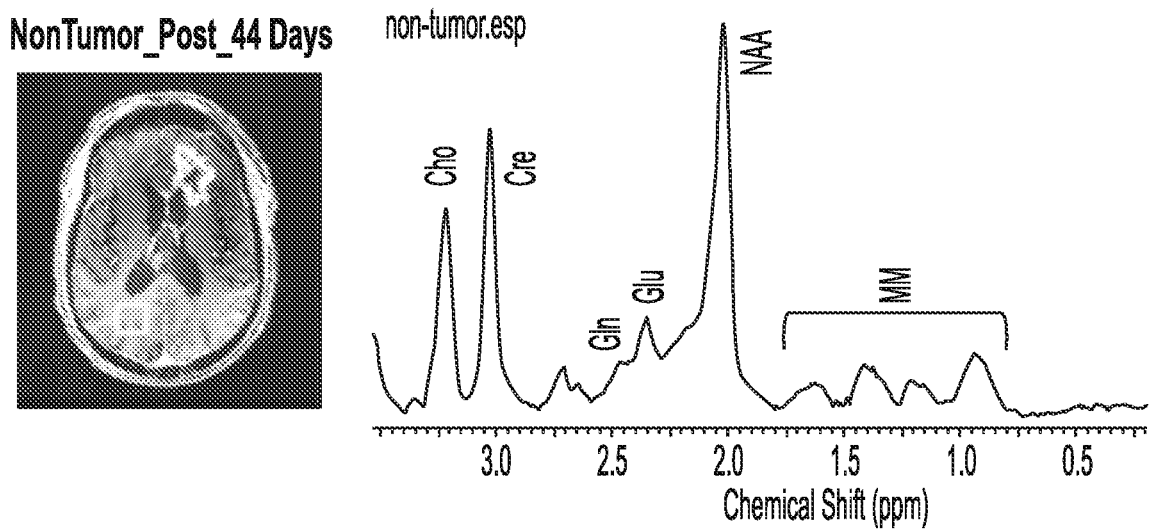
FIG. 24B illustrates an in vivo $^1$H MR spectrum of a non-tumor region of a GBM patient 44 days after initiation of OMF treatment, showing the presence of the neurochemicals NAA, Glu, Gln, Cre, Cho, as well as macromolecules (MM)
Figure 24C:
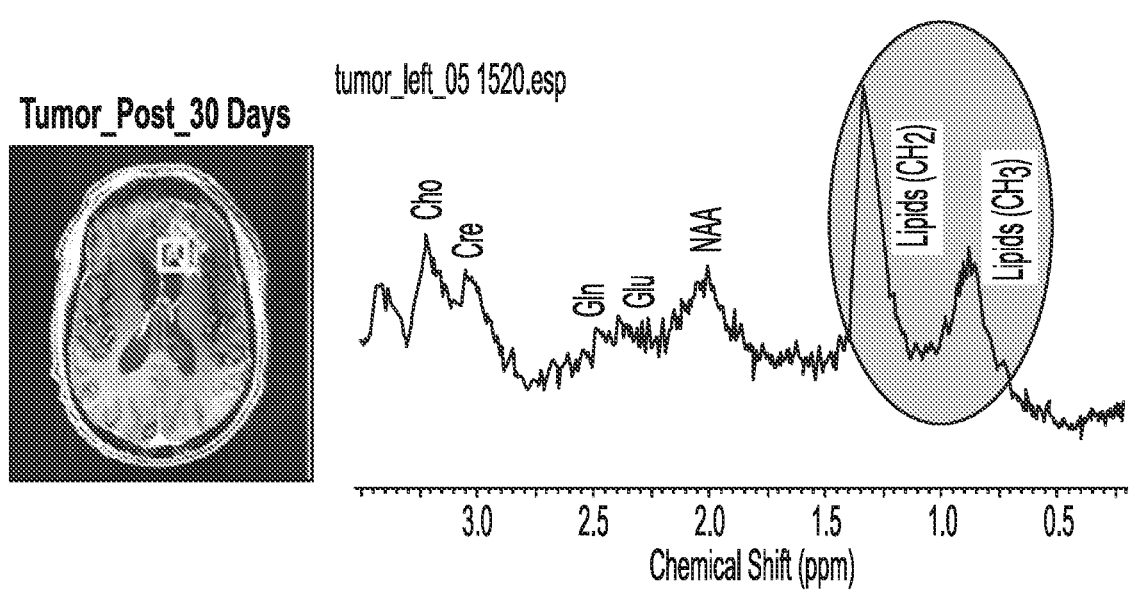
FIG. 24C illustrates an in vivo $^1$H MR spectrum of a tumor region of a GBM patient 30 days after initiation of OMF treatment, showing low levels of neurochemicals and significantly elevated levels of mobile lipids (CH2 and CH3 protons of lipids) arising due to necrosis/apoptosis brought about by OMF therapy.
Figure 24D:
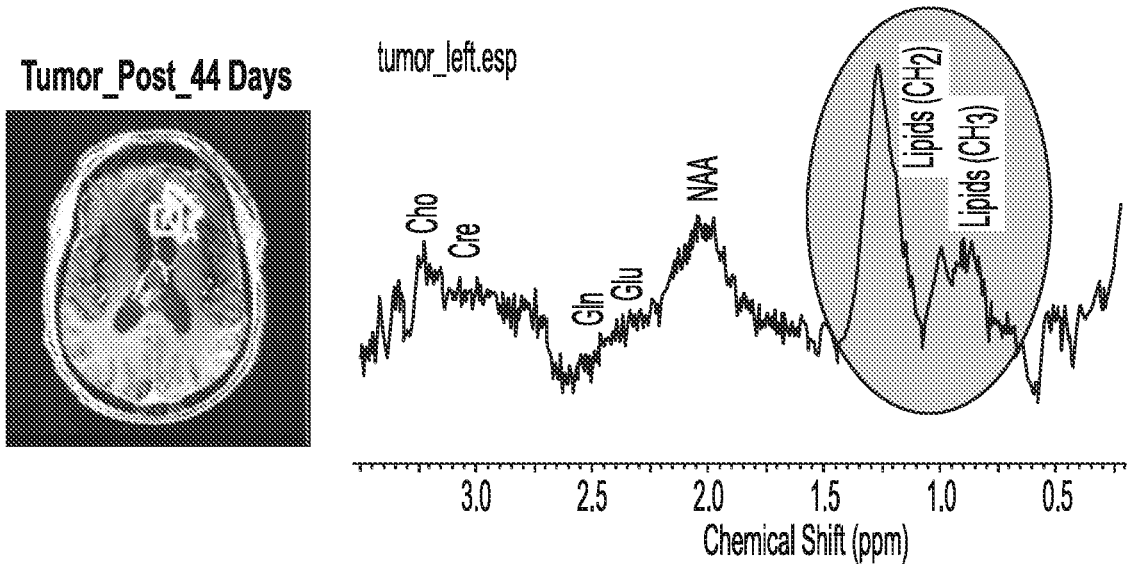
FIG. 24D illustrates an in vivo $^1$H MR spectrum of a tumor region of a GBM patient 44 days after initiation of OMF treatment, showing low levels of neurochemicals and significantly elevated levels of mobile lipids (CH2 and CH3 protons of lipids) arising due to necrosis/apoptosis brought about by OMF therapy.

It was observed that after 30 days of OMF treatment, the tumor region showed new peaks at 1.30 ppm and 0.88 ppm in the 1H MR spectra. These peaks arise from mobile lipids which were shown earlier to be generated in the tumor region due to necrosis/apoptosis, or another mechanism of cell death. As shown in FIG. 24B, non-tumor region did not show any significant changes in the levels of NAA, Cre, Cho and lipids during the OMF treatment. Based on preclinical laboratory studies in patient derived GBM cells in culture, it was hypothesized that OMF applied to these cancer cells disrupt redox pathways within cells and increase the intracellular levels of reactive oxygen species (ROS), leading to cancer cell necrosis/apoptosis, or another mechanism of cell death, which is an effect that is potentially of therapeutic value.

The Configuration Used in the Treatment Above

Figure 25:
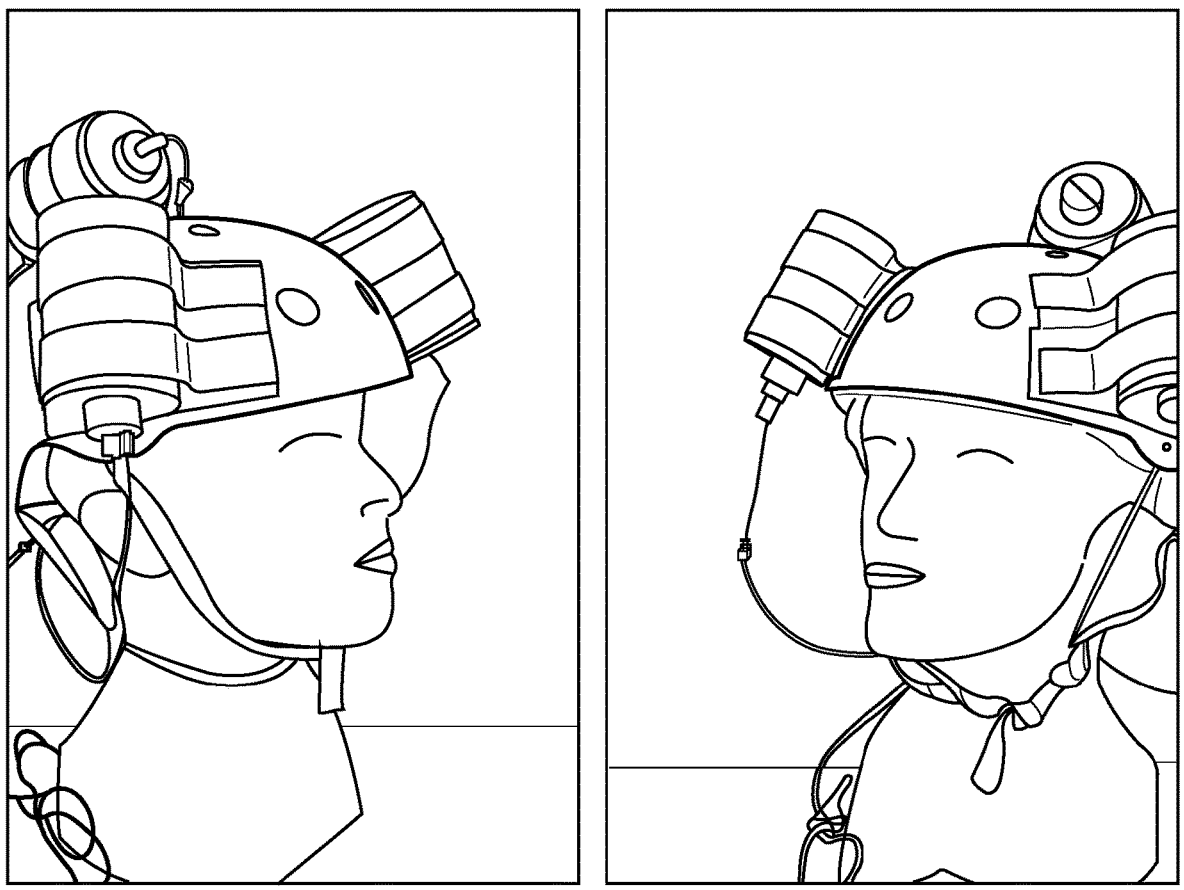
FIG. 25 illustrates a device helmet with three oncoscillators securely attached thereto and connected to a controller box powered by a rechargeable battery, used to generate the results of FIGS. 24A-D.

The particular device used with the 53-year-old patient reference above has exactly three oncoscillators securely attached to a helmet and connected to a microprocessor-based electronic controller operated by a rechargeable battery, as illustrated in FIG. 25.

Imaging studies of the patient documented a large tumor in the left frontal lobe extending across the midline into the right frontal lobe, with diffuse and extensive infiltration through the corpus callosum. There was mass effect and severe edema. The patient underwent left frontal craniotomy and radical excision of the tumor. The tumor was histopathologically confirmed as GBM. At the time of the surgery, the excision extended across the midline into the right frontal lobe. The patient was enrolled in a herpes simplex virus-thymidine kinase gene therapy program and received viral injection during surgery per protocol. In addition, per protocol, and as standard of care, he received concomitant radiation therapy and chemotherapy with temozolomide.

The patient presented with an area of contrast enhancement on MRI scan along the left ventricle. At first this was thought to be a treatment effect. This area progressively enlarged. Evaluations done before OMF treatment initiation demonstrated a clear recurrence. The tumor abutted the ventricle and there was evidence of leptomeningeal spread. The patient had already had radiation therapy and chemotherapy and the tumor was now progressing. The presence of leptomeningeal disease portends poor outcome, with median survival of 3.5 to 3.9 months 12.

The patient was enrolled in an FDA-approved Expanded Access Program (EAP) for compassionate use treatment with the Oncomagnetic device. He signed an informed consent, and, and the EAP study was carried out under a protocol approved by the Houston Methodist Research Institute Institutional Review Board.

The treatment consisted of intermittent application of an OMF that needs to be generated by rotating permanent magnets in a specific frequency profile and timing pattern to be effective. The patient received this treatment initially for the first 3 days. The dose was escalated over this period as follows. On the first day, the treatment was for 2 hours with a 5-min break between the first and the second hour. On the second and third days, it was increased to 2 and 3 2-hour sessions, respectively, with 1-hour breaks between the sessions.

The microprocessor in the device of FIG. 25 runs a software program that activates the oncoscillators sequentially for specified durations (250 milliseconds (ms)) and with precise timings (at 750 ms intervals with respect to each other), to achieve an effective maximal frequency in the range of 200 to 300 Hz. The helmet is worn by the patient over a tight-fitting neoprene cap. The first oncoscillator is attached to the helmet at a left frontal location corresponding to the location of the tumor, the second at a symmetrical location on the contralateral side, and the third in the midsagittal plane at the parieto-occipital junction. Based on a finite element model-based calculation of the spread of the field and the size and magnetization of the rotated magnets, it was estimated that the combined effective field (at least 1 mT in strength) of the 3 oncoscillators covered the entire brain, including most of the brain stem.

The patient was evaluated clinically by the treating physician on each of the 3 days he was receiving treatment in the clinic and 7, 16, 30 and 44 days after initiation of treatment. Magnetic resonance imaging (MRI) scans were done on Days 1, 3, 7, 16, 30 and 44. The Day 1 scan was done before initiation of treatment. All other scans were done after treatment initiation. The treatment was paused on Day 37. MRI scans were done on a Siemens Magnetom Terra 7T scanner. MRI scans included T1 MPRAGE scans with and without gadolinium contrast, and T2-FLAIR, T2-TSE, DWI, SWI and DTI scans.

Post-contrast T1 anatomical MRI scans at each of the 6 time points were used to determine changes in contrast-enhanced tumor (CET) volume before and after initiation of treatment. The DICOM images were converted to the NifTi 3D volume format using MRIcron (Chris Rorden) software. Post-contrast scans at each post-treatment initiation time point were co-registered with the pre-treatment Day 1 scan using Statistical Parametric Mapping version 12 software (Institute of Neurology, University College London). The co-registered scans were then imported into MATLAB (Mathworks, Natick, Mass.) and CET volume estimated using a MATLAB script and a uniform normalized intensity threshold. The mean volume and intensity were then plotted as a function of time.

Values obtained from pre-treatment clinical scans taken at 2 time points over 3 months before enrollment of the patient were also plotted on the same graph. The pre- and post-treatment initiation T2-FLAIR scans were co-registered in the same manner as above with the pre-treatment T1 post-contrast scan. However, the co-registered scans were subjected to skull-stripping (brain extraction) in MRIcron. The volume of enhanced intensity in T2-FLAIR was then estimated by normalized intensity thresholding using the MATLAB script, and bar plots of the volume in each hemisphere with respect to time were plotted.

Figure 26:
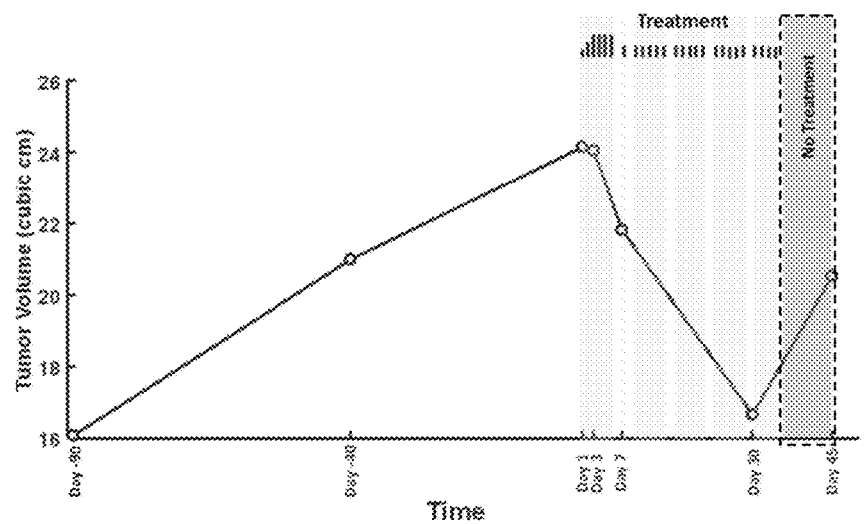
FIG. 26 is a graph showing the change in CET volume over time, with the treatment times and durations shown as bars and highlights, and the pause in treatment shown as a another highlight.

The T1 post-contrast scans showed marked changes in tumor volume with treatment. FIG. 26 illustrates a plot of the CET volume as a function of time before and after initiation of treatment. The plot reveals that there was substantial growth of the tumor volume over the 3 months before the treatment. Within the first 3 days of treatment the trend is reversed with the volume steeply decreasing by ~10% on Day 7 and then less steeply by >30% on Day 30. The treatment was paused on Day 37. After the pause on Day 44 another trend reversal and an increase in CET volume was observed.

Figure 27:
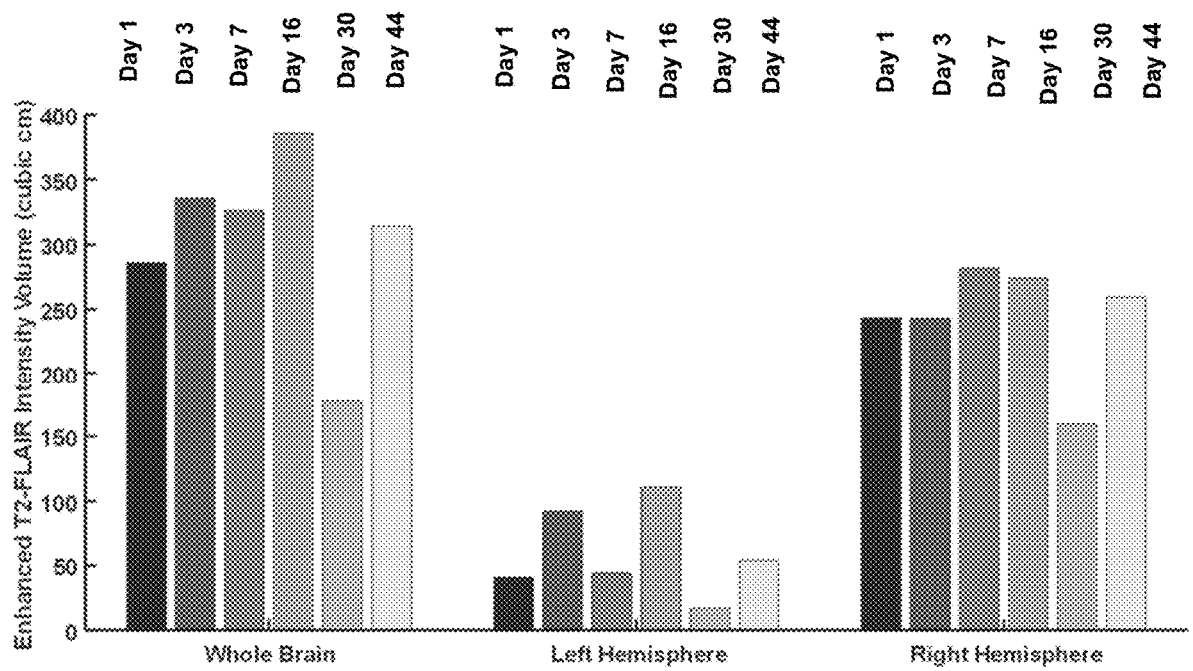
FIG. 27 illustrate bar plots of the volumes of T2-FLAIR intensity enhancement in the whole brain and the two hemispheres at different time points.

The T2-FLAIR data (FIG. 27) show a more complicated trend over time. However, the largest decrease in enhanced intensity volume is seen on Day 30, matching the change in CET volume in FIG. 26. This volume also increased after 8 days of no treatment on Day 44, in line with the increase in CET volume in FIG. 26. The hemispheric profile of changes reveals that the T2-FLAIR enhancement is greater on the side contralateral to the tumor.

The findings of this study indicate that oncomagnetic device-based OMF therapy is well tolerated by a patient who has end-stage recurrent GBM with leptomeningeal involvement and has no other available effective treatment options. They also demonstrate a clinically significant reduction in CET volume with a possible decrease in non-enhanced tumor volume due to infiltration on T2-FLAIR scans. The temporal profile of changes in CET volume also reveals a correlation with the treatment dose and the presence or absence of treatment. When the treatment dose was higher (6 hours/day for 4 days) a tumor volume reduction rate of 2.32 $cm^3$/day can be observed. When the dose was lower (2 hours/day for 9 days and 3 hours/day for 18 days), the reduction is 1.03 $cm^3$/day. Moreover, when the treatment was paused for 8 days the decreasing CET volume trend reversed and increased, instead. Assuming that the ~1.03 $cm^3$/day decreasing trend had continued until the treatment was paused, it can be estimated that the CET volume grew at the rate of 1.26 $cm^3$/day during the pause.

Another Example of Inducing Selective Rapid Apoptosis or Another Mechanism of Cell Death of Cancer Cells In another example configuration, three different lines of malignant cells from surgically excised human GBM tumors were exposed to OMF which an oncoscillator of this disclosure generates. In all of these experiments, the oncoscillators were positioned so that the cells were exposed to a peak to peak rotated magnetic field of 1-58 mT strength. The intermittently delivered OMF patterns were systematically varied in peak frequency (PF; 50-350 Hz), pulse train duration (TD; 50-1000 ms), inter-pulse train off intervals (TI; 92-2000 ms) and total exposure time (ET; 2-4 h). The results obtained under these intermittent exposure conditions also were compared with continuous OMF exposure at a peak frequency of 350 Hz for 2 h.

In a control set of experiments cells were exposed to sham treatment or no OMF treatment at all. The sham treatment involved an ineffective oncoscillator that rotated a nonmagnetic metallic or plastic rod in the same way as the OMF producing magnet. During and up to 4 h after the end of active, sham or no treatment, the OMF effects were videorecorded on unstained GBM cells under a microscope.

Nearly all cells in the active treatment condition (PF ~350 ms, TD 250 ms, TI 250 ms and ET 2 h) show blebbing and deformation, suggestive of apoptosis or another means of cell death at 3 h, but no such change in structure is observed in the two control conditions. The transition from normal GBM cell morphology to apoptotic one occurred precipitously over a short period of 10-15 min. This is evident from the plot of intensity versus time in FIG. 28. The intensity plot was made from an entire 4 h video of the active OMF treatment condition. The cytotoxic effect of OMF is seen in GBM cells in resting phase of the cell cycle. OMF stimulated cells grown in the absence of fetal calf serum and stained with a mitochondrial stain (MitoTracker™) exhibit the mitochondrial morphology of cells that are about undergo apoptosis, or another mechanism of cell death (see below). This result demonstrates that the oncolytic effect is not restricted to dividing cells.

Figure 28:
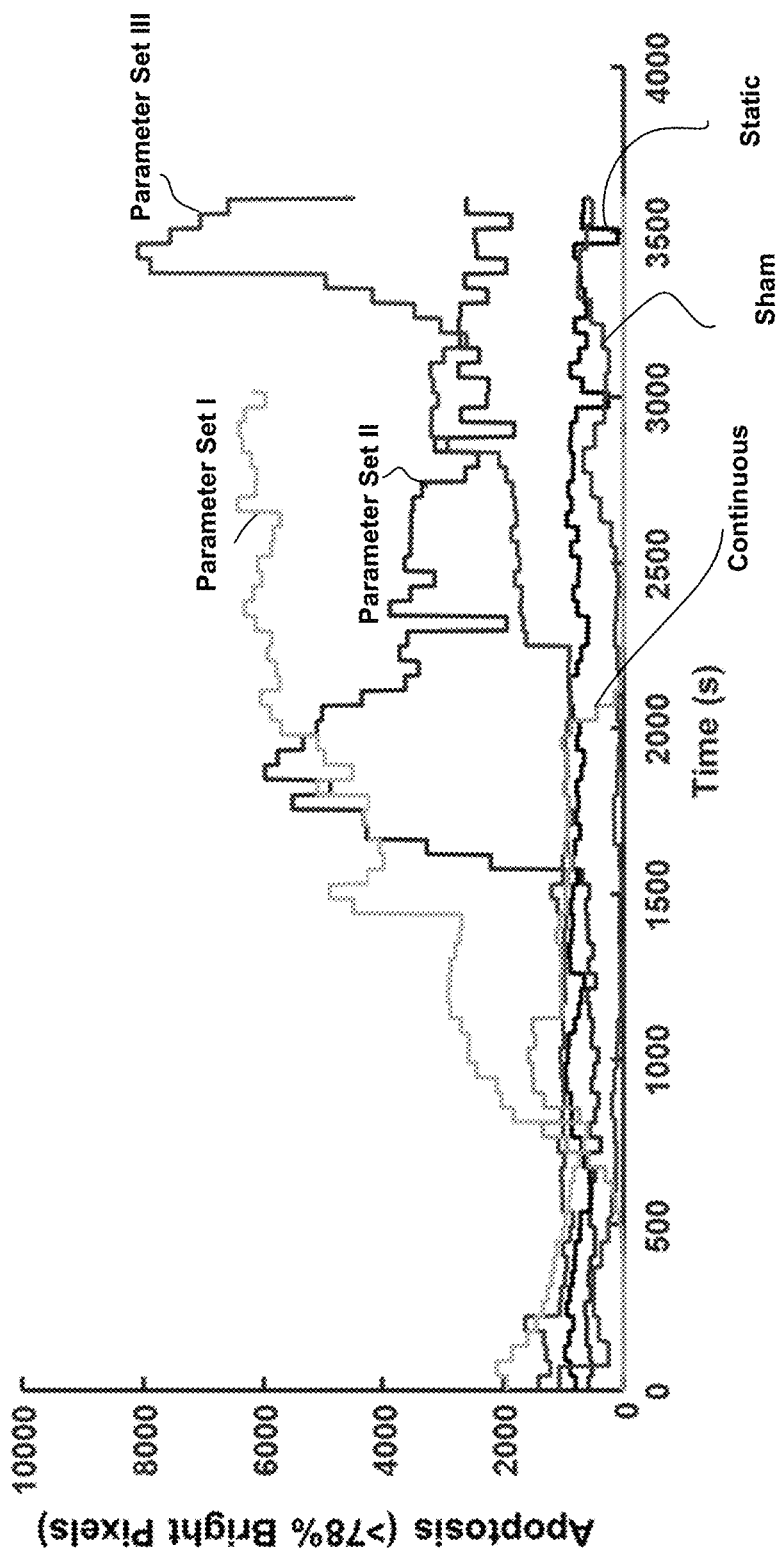
FIG. 28 illustrates several apoptosis-versus-time plots for the respective parameter configurations. Plots of a brightness index (pixels with >78% brightness) of apoptosis as a function of time in cells treated under different conditions—intermittent stimulation with each of 3 different sets of stimulus parameters (changes in TD and TI at a constant PF and ET); continuous stimulation at the same PF; unrotated static magnetic field; and sham stimulation. The intensity plot was made from the 1 h period during the rapid transition to apoptosis in the course of an entire 4 h time lapse video of the active OMF treatment under 3 different sets of stimulation parameters. The cytotoxic effect of OMF is seen in GBM cells even in the resting phase of the cell cycle.

Other OMF treatment parameters show qualitatively similar effects on cell morphology as above but vary quantitatively in time course, as seen in the intensity plot in FIG. 28. This effect, however, occurs only if the active treatment involves intermittent exposure to OMF and not if the cells are exposed to OMF continuously over the same ET of 2 h. It also does not occur in the sham-treated, static magnetic field (unrotated magnet) and untreated conditions. These experiments were repeated in cell cultures of 4 other types of malignant tumors (malignant meningioma, diffuse intrinsic pontine glioma (DIPG), triple negative breast carcinoma, and non-small cell lung carcinoma), and these experiments yielded similar results.

Figure 29:
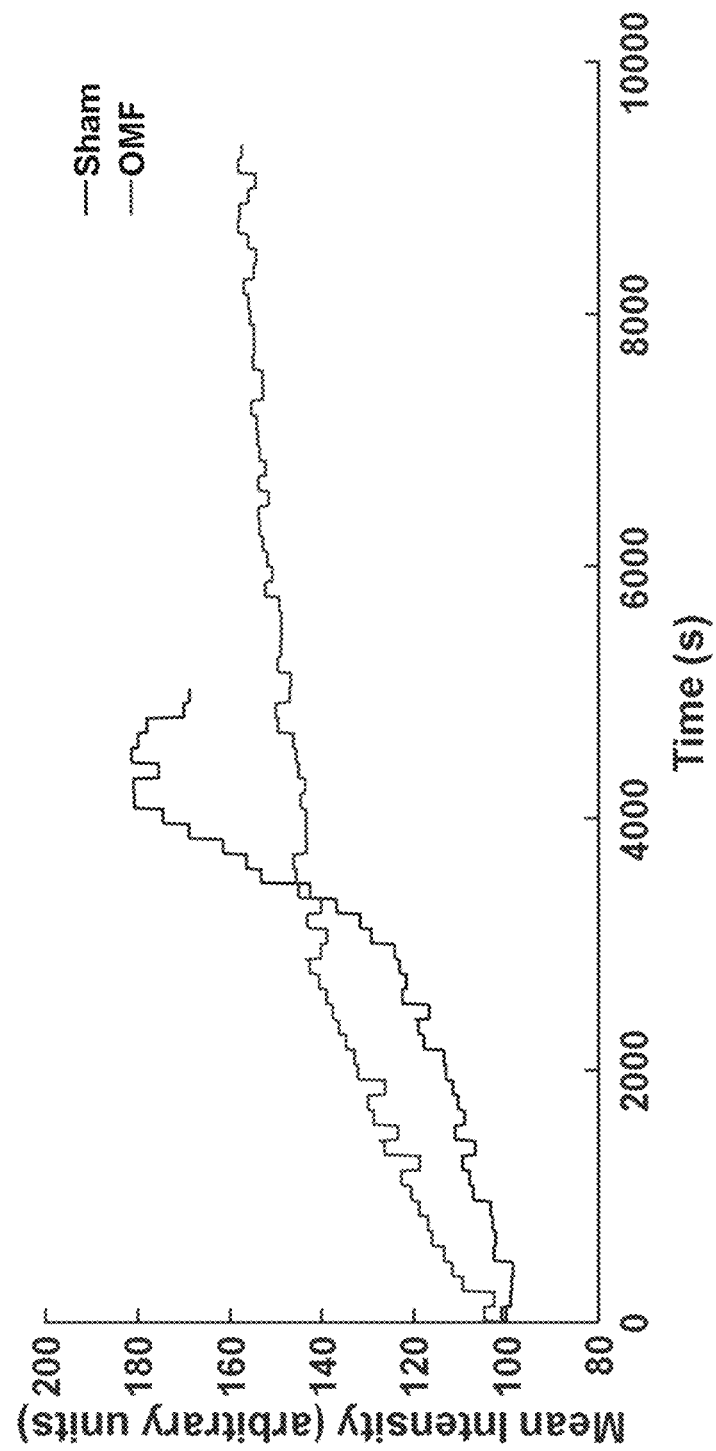
FIG. 29 shows a graph of the MitoTracker fluorescence intensity as a function of time in sham and OMF-treated cells, reflecting the time course of increase in damage to cells due to the oxidative stress. The graph displays of the mean intensity above a common threshold of unstimulated and OMF-treated normal human astrocytes as a function of time, showing steeper rise to a higher level in the sham condition compared to the OMF condition. This rise correlates with a morphological change indicating breakdown of the mitochondrial network due to singlet oxygen produced by MitoTracker fluorescence, which is attenuated by OMF, presumably due to feedback upregulation of the antioxidant mechanisms. The rise in intensity (cytotoxic damage) occurs more rapidly and to a higher level in sham-treated compared to OMF-treated cells. It takes ~89 min for all cells in a microscopic field to be killed in the sham condition compared to ~156 min in the OMF condition.

OMF treatment of normal human astrocytes (NHA), bronchial epithelial cells and B lymphocytes show no morphological changes consistent with apoptosis or cell death. Furthermore, the lack of cell death is reflected in cell counts. In fact, with NHA an OMF-induced protective effect against the time-dependent toxicity of singlet oxygen produced by MitoTracker fluorescence can be observed. MitoTracker is a mitochondrial membrane potential probe that reveals mitochondrial damage in dying cells. FIG. 29 shows plots of the MitoTracker fluorescence intensity as a function of time in sham and OMF-treated cells, reflecting the time course of increase in damage to cells due to the oxidative stress. It can be seen that the rise in intensity (cytotoxic damage) occurs more rapidly and to a higher level in sham-treated compared to OMF-treated cells. It takes 89 min for all cells in a microscopic field to be killed in the sham condition compared to 156 min in the OMF condition. Further, in images showing the morphology of NHA in the two conditions at the same time-point, there is intense staining due to mitochondrial disruption in sham-treated but not OMF-treated cells at this time-point.

Figure 30A:
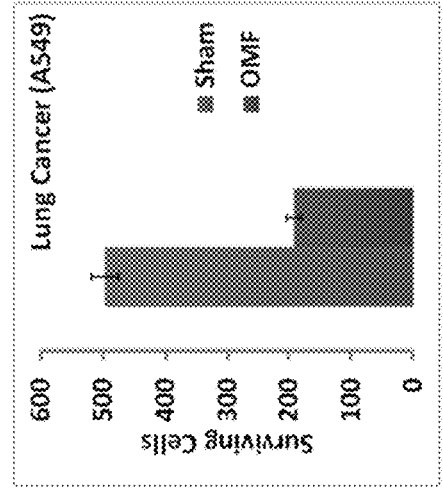
FIGS. 30A-E are histograms of surviving 4',6-diamidino2-phenylindole (DAPI)-stained GBM cell nuclei in cell culture for OMF and sham treatments, for several types of cells.
Figure 30B:
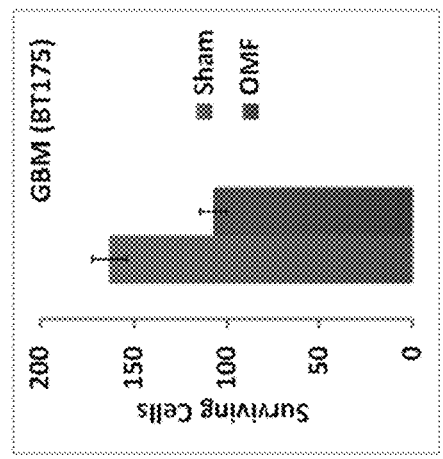
Figure 30C:
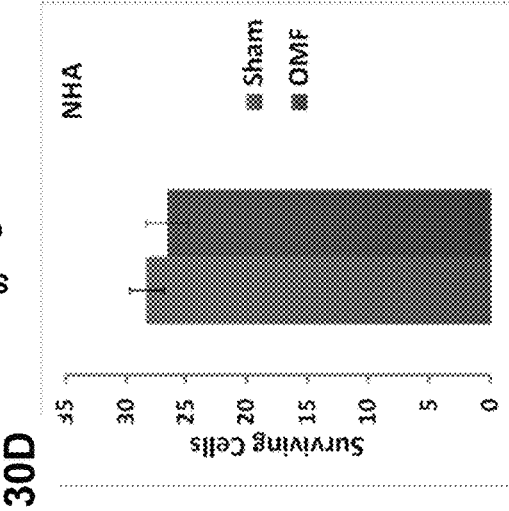
Figure 30D:
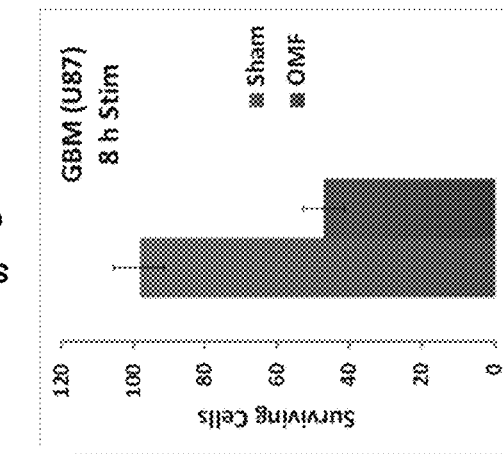
Figure 30E:
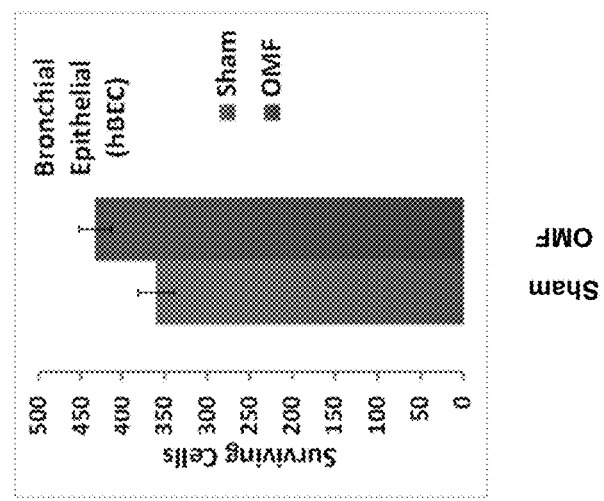

To quantify the oncolytic effect of OMF, surviving DAPI-stained GBM cell nuclei in cell culture 24 and 48 h after 4 h OMF stimulation were counted. FIG. 30A shows a ~33% reduction in cell count after 24 h. A similar decrease was seen in DIPG cells (data not shown). In A549 non-small cell lung carcinoma cells the decrease in cell number after 48 h is ~60% (FIG. 30B). A tested also was conducted to determine whether the effect of multiple OMF exposures on successive days was cumulative. This is important to know because during the long pause between the end of stimulation and counting of cells the surviving cells would proliferate and artifactually reduce the observed killing effect of OMF. For this experiment a different GBM cell line (U87) was used because it proliferates faster. It was found that 24 h after one 4 h session of OMF exposure there is only ~20% decrease in cell count of these cells. However, FIG. 30C shows the count decreases by more than 50% after two 4 h OMF stimulation sessions on successive days. FIGS. 30D and 30E show that OMF does not cause a decrease in NHA or normal bronchial epithelial cell counts.

Cell Death is Due to Caspase-Dependent Apoptosis

Figure 31B:
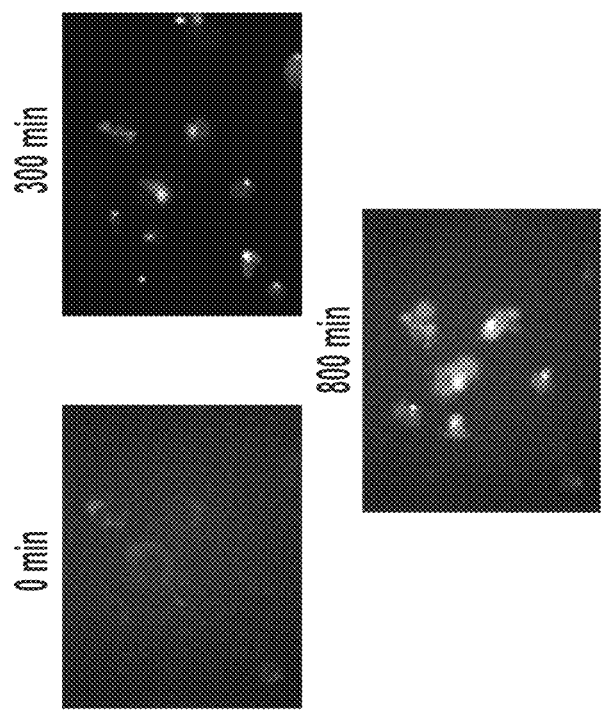
FIGS. 31A-B illustrate a graph of fluorescence intensity as a function of time for GBM cells double-stained with MitoTracker, and the relevant images and freeze frames.
Figure 31A:
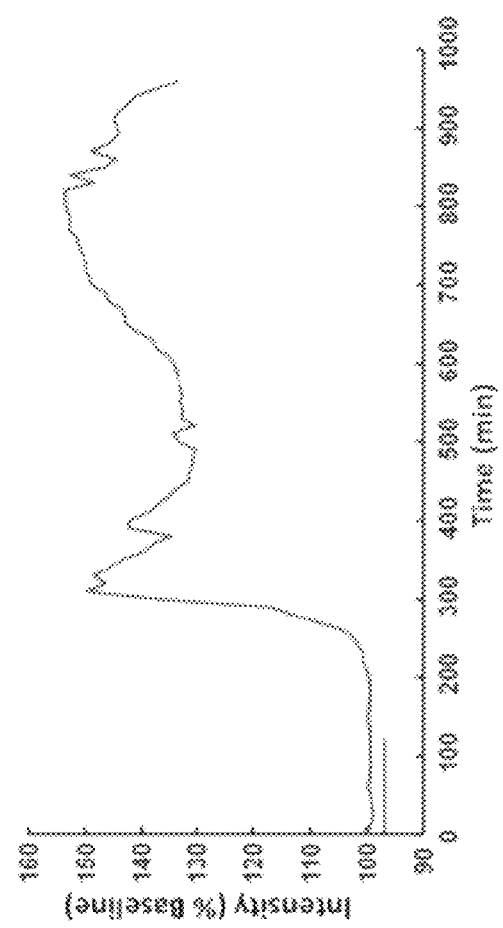

To test whether the rapid apoptosis induced by OMF was mediated by the intrinsic caspase-dependent pathway, live OMF-treated GBM cells were immunostained to detect activated caspase 3. Activation of caspase 3 is the penultimate step in this pathway. The graph of fluorescence intensity as a function of time in FIG. 31A shows the time course of activation of caspase 3 in cells stained only for the activated enzyme. Freeze frames from this video showing deformation of the cell morphology are depicted in FIG. 31B. The time-lapse video of cells showing gradual OMF-dependent activation of caspase 3, leading to apoptotic blebbing.

OMF Disrupts Mitochondrial Function and Network

As discussed above, using oxygen electrode measurements, short applications of OMF produced by oncoscillators causes a complete arrest of mitochondrial oxygen consumption followed by its rapid increase when OMF stimulation is paused. The rapid increase is likely due to opening of the mitochondrial membrane permeability transition pore (MPTP) because a potent blocker of the adenine nucleotide translocase component of the pore completely blocks this increase.

Oncolytic Effects of OMF are Due to Increase in ROS

OMF effects on mitochondrial oxygen consumption would cause an increase in the generation of superoxide, which would then dismutate to hydrogen peroxide ($H_2O_2$), both of which constitute the two main longer-lived components of ROS. Superoxide is a potent activator of MPTP and $H_2O_2$ diffuses out of the membranes into the cytoplasm and extracellularly to cause downstream cytotoxic effects. Therefore, the entire cascade of effects that can be observed could be due to the generation and release of ROS. This possibility was tested by investigating whether superoxide and $H_2O_2$ are generated by OMF exposure and by quantifying their levels, using selective fluorescent probes Mito-SOX™ and H2DCF.

Figure 32B:
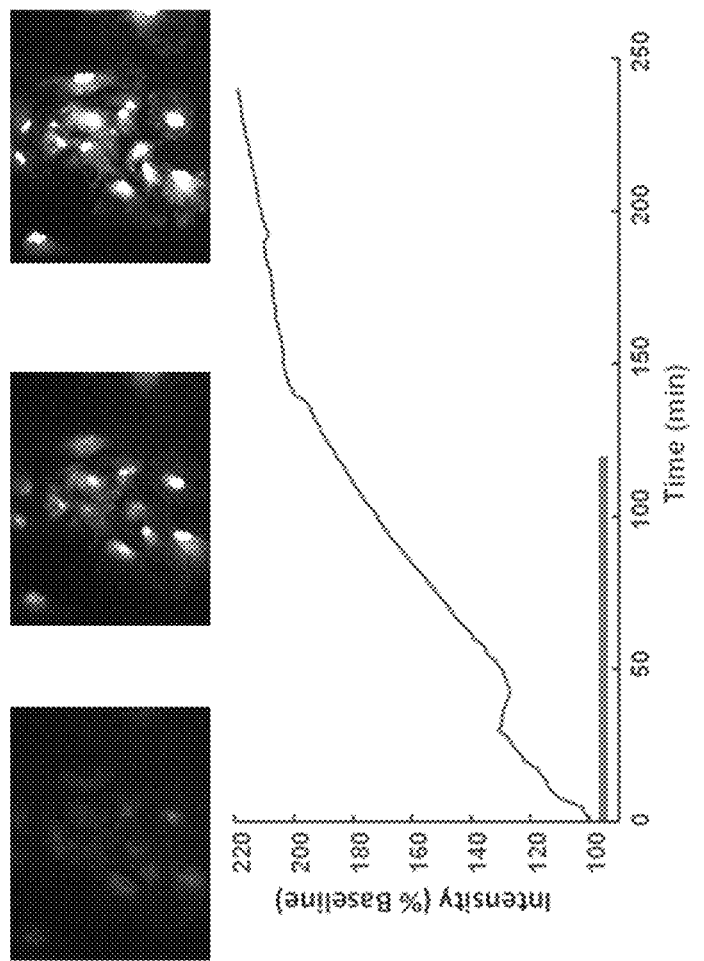
FIGS. 32A and B illustrate increases in the levels of superoxide and $H_2O_2$ in GBM cells, as detected by a rise in the fluorescence intensities of the two probes, and the relevant photomicrographs.
Figure 32A:
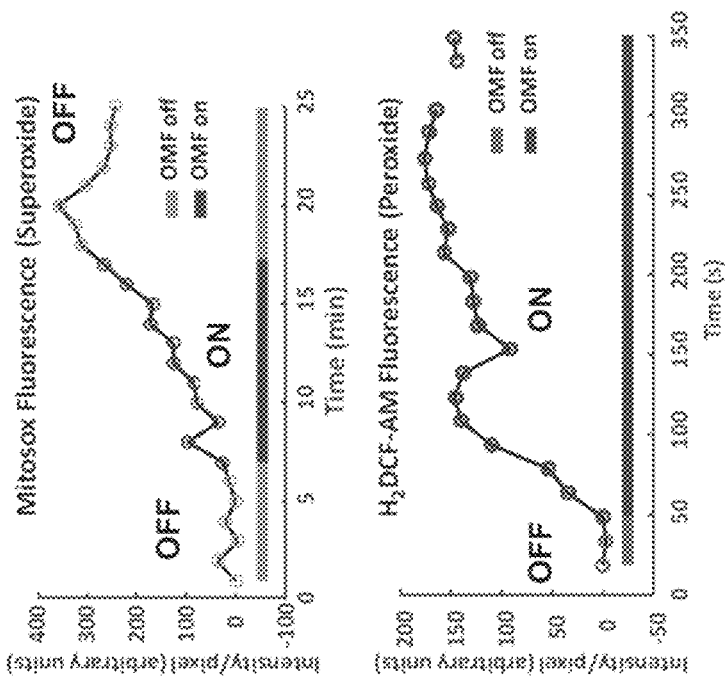

FIG. 32A-32B show rapid and pronounced elevation of ROS with OMF. FIG. 32A shows rapid increases in the levels of superoxide and $H_2O_2$ in GBM cells, as detected by a rise in the mean intensity of fluorescence of the two probes. The mean intensity (>50 RGB R level) of fluorescence normalized with respect to baseline (at the start of OMF exposure) is plotted against the time in minutes. Mean intensity represents the mean level of superoxide per GBM cell. A steady increase in intensity is seen from the start of OMF exposure. The black bar indicates the time of OMF treatment. FIG. 32B shows photomicrographs at 3 time points and corresponding intensity versus time plot of Mito-SOX'-stained GBM cells, in another experiment involving OMF stimulation for 4 h.

Figures 33A, 33B, 33C:
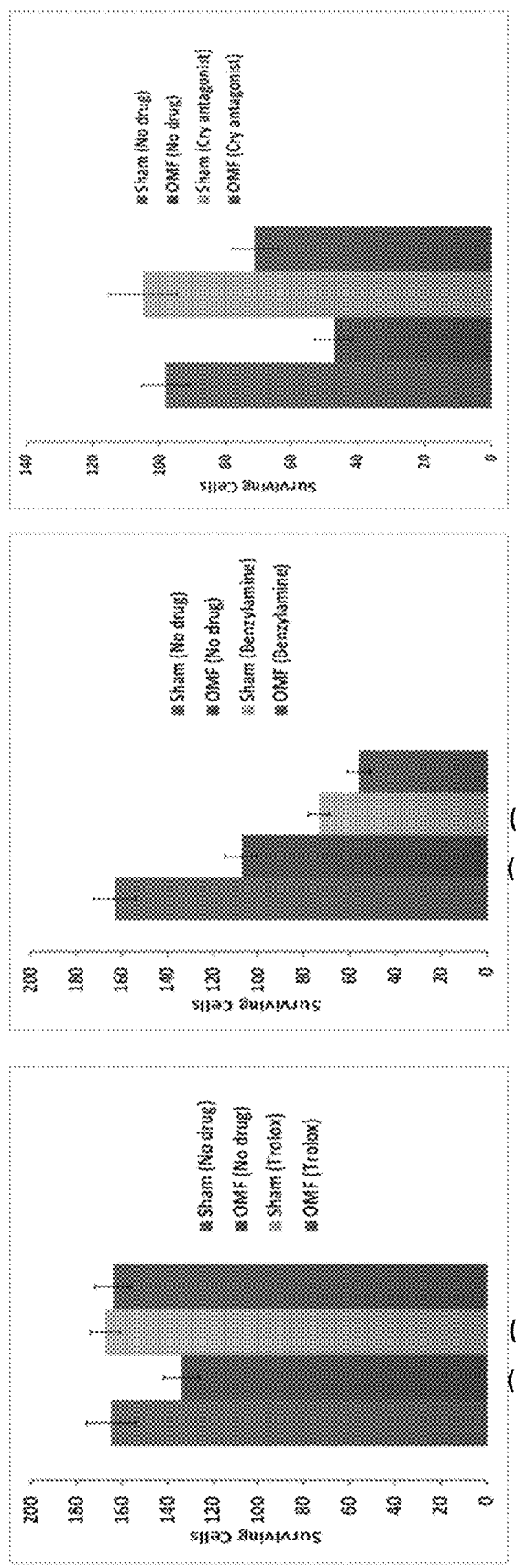
FIGS. 33A-C are histograms of surviving cells for several types of treatment.
Figure 44:
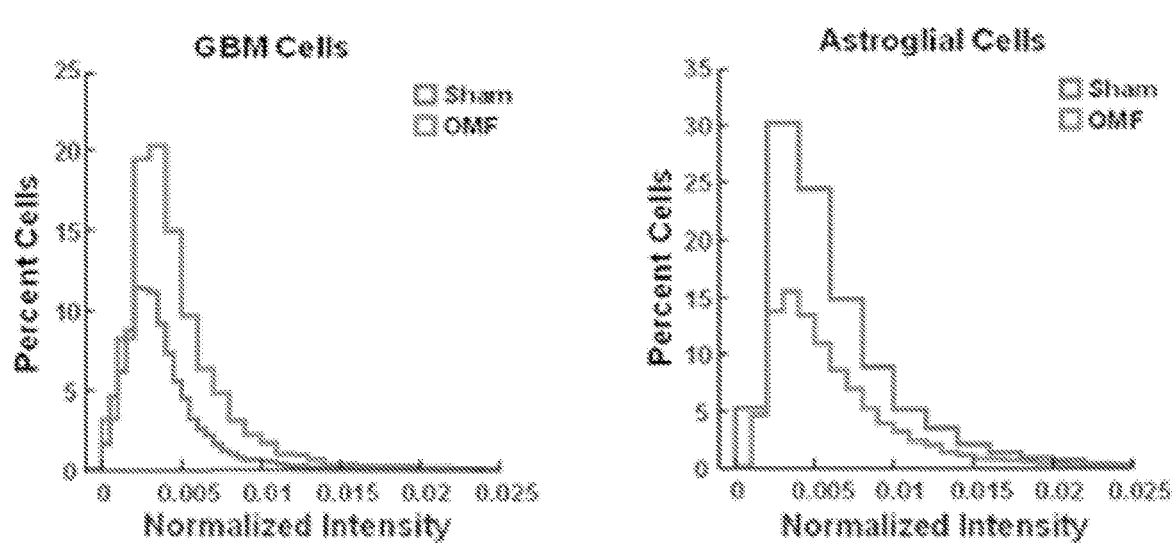
FIG. 44 include histograms showing the distribution of H2DCF-stained GBM (U87) (left panel) and normal astroglial (SVGp12) (right panel) cells plotted from flow cytometric data.

The experiments showed rapid increases in the levels of superoxide and $H_2O_2$ in GBM cells, as detected by a rise in the fluorescence intensities of the two probes. Sham stimulation does not show these increases. Histograms of the percentage of cells plotted against the normalized fluorescence intensity (ratio of intensity to the width of the forward scatter) measured by flow cytometry of H2DCF-stained GBM (U87) and normal astroglial (SVGp12) cells reveal nearly a two-fold increase in GBM cells due to OMF, but a ~50% decrease in astroglial cells (FIG. 44). To test whether cell death is caused by the OMF-induced increase in ROS, a potent antioxidant Trolox was used to counteract it, while measuring the decrease in GBM cell count due to 4 h exposure to OMF. Conversely, it also was asked whether OMF potentiates the cell killing effect of a known ROS inducer, benzylamine FIGS. 33A-33B and 44 show that both these predictions are confirmed, indicating that the cytotoxic effect of OMF on GBM cells is mediated by induction of ROS.

Test of an Alternative Hypothesis of ROS Generation

Magnetically influenced RPM plays a role in ubiquitously expressed flavoproteins called cryptochromes, which can also generate ROS when perturbed by magnetic fields. Cryptochrome agonists have been recently shown to inhibit cancer stem cell proliferation in GBM. This alternative possibility for generation of ROS by OMF was tested by counting surviving cells after two 4 h sessions of OMF stimulation over 24 h in the presence and absence of a cryptochrome antagonist, KS15. As can be seen in FIG. 33C, there is a significant partial attenuation of the decrease in cell count produced by OMF when cryptochromes are inhibited.

Additional Example

Figure 34:
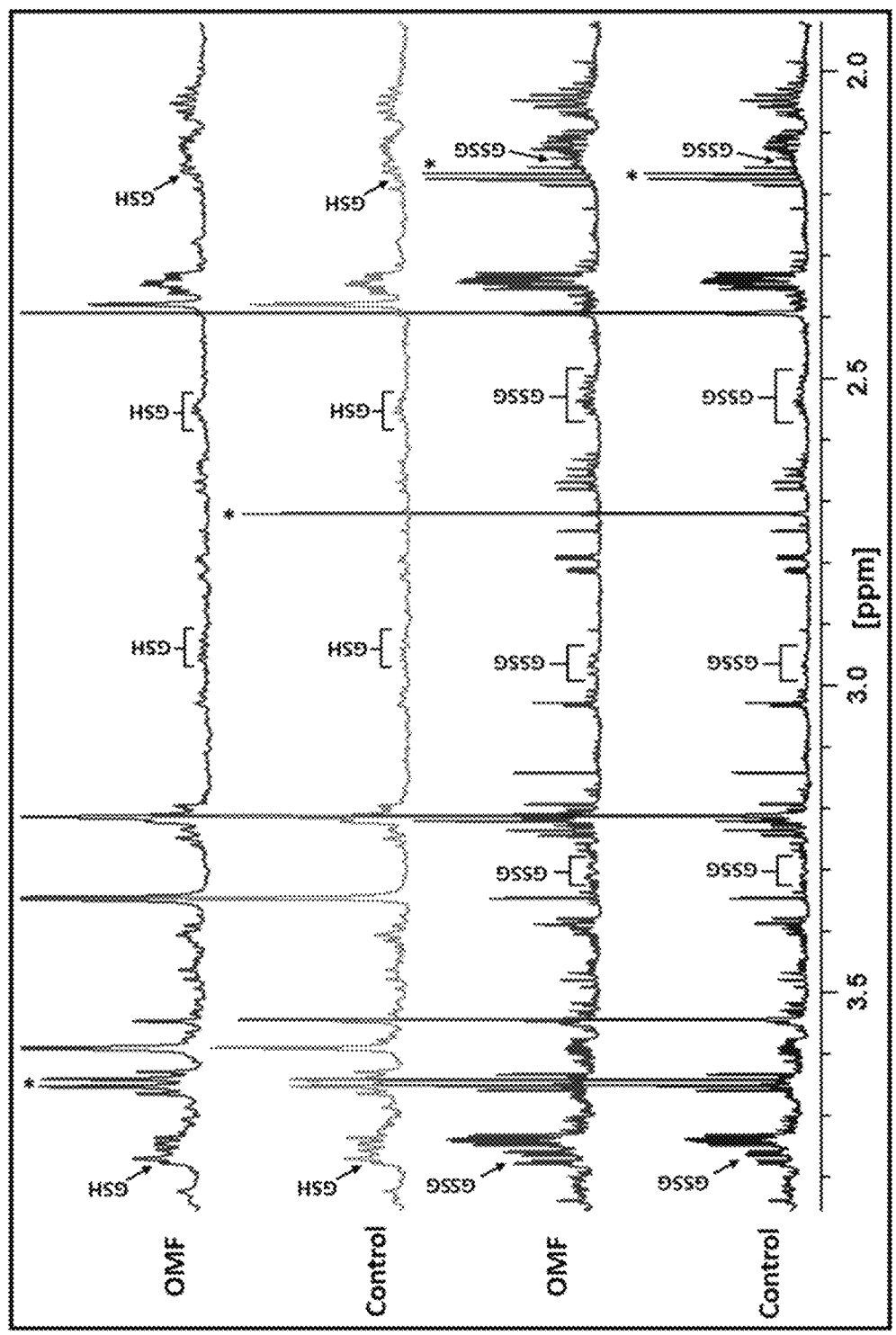
FIG. 34 illustrates $^1H$ NMR spectra showing the GSH and GSSG peaks in control and OMF treated GBM cell extracts.

FIG. 34 illustrates $^1H$ NMR spectra showing the GSH and GSSG peaks in control and OMF treated GBM cell extracts. GSH was detected in the cell extracts flushed with helium gas. The GSH levels were quantified using the 'CH2' proton signal resonating at 2.54 ppm, and the GSSG levels were measured using the multiplet proton signal (S—CH—) at 2.96 ppm. In this example, an oncoscillator array includes an assembly of a N52 grade neodymium permanent magnets attached to the shafts of electric motors. The oncoscillators are encased in 3D-printed Nylon 12 plastic holders mounted on a wooden frame. Culture plates containing the GBM cells are placed under the oncoscillators on a turn table.

Oncoscillator Array Setup for the Metabolism Studies

In an example configuration, an OMF-producing oncoscillator array includes an assembly of a N52 grade neodymium permanent magnets attached to the shafts of electric motors. Oncoscillators were encased in 3D-printed Nylon 12 plastic holders which were mounted on a wooden frame. Individual oncoscillators were controlled by a programmable microprocessor-based console running a software program operated by an Android application on a Bluetooth-connected electronic tablet. The controller console was powered by an external battery or a power adaptor. Repeated intermittent OMF was applied at a specific frequency, in the 200-300 Hz frequency range, with on-off epochs of 250 or 500 ms duration. The total OMF treatment time was 3 h. The culture plates (n=4) containing the GBM cells were placed on a plastic plate which in turn was placed on an anti-slip rotating turn table. The turn table was mounted on anti-vibration rubber pads.

Glutathione Analysis

GBM (BT-175) cells were grown in 100 mm×20 mm culture dishes (n=3 each for Test and Control groups) in high glucose DMEM. Cells were treated with and without OMF for 3 h, trypsinized, washed with PBS, the cell pellets obtained were snap-frozen in liquid nitrogen and stored at −80° C. until further analysis. Cell pellets were extracted with 0.5 mL of methanol:chloroform (2:1 ratio, v/v) solvent mixture which was flushed with helium gas. Further, the above cell extract was vortexed by adding 0.25 mL of chloroform and 0.25 mL of Millipore water (1:1 ratio, v/v). Finally, the aqueous-methanol and chloroform layers were separated by centrifugation. The methanol layer was used for the quantification of glutathione and other water-soluble metabolites. The solvent in the methanol layer was dried in a flow of helium gas and the residues were reconstituted in 180 μL $D_2O$ containing 1.0 mM DSS-$d_6$ (internal standard), and the pH of the solution was adjusted to 7.4±0.05. The sample solutions were flushed with helium gas before transferring them to the 3.0 mm NMR tubes, and the tubes were sealed with paraffin film to avoid any contact with air.

$^1$H NMR Experiments

One-dimensional (1D)$^1$H NMR spectra of cell extracts were collected on a Bruker 800 MHz spectrometer ($^1$H frequency) equipped with a cryoprobe for $^1$H/$^{13}$C detection. $^1$H NMR data were collected using the pulse sequence 'noesypr1d' which makes use of nuclear Overhauser effect spectroscopy (noesy) and pre-saturation of water signal during relaxation and mixing times. The NMR spectroscopic data were collected using the following acquisition parameters: number of scans=128, 90° pulse=8.1 µs, time domain points=64 k, inter-pulse delay=5.0 s, spectral width=9,615 Hz, acquisition time=3.40 s, mixing time=100 ms. The time domain data were multiplied by an exponential window function with a line broadening of 0.3 Hz, before Fourier transformation. Peak areas of $^1$H NMR spectra were measured by using Bruker TopSpin software version 4.0. Glutathione levels were quantified using the 'CH$_2$' proton signal resonating at 2.54 ppm, while GSSG levels were measured using the multiplet proton signal at 2.96 ppm from the sample prepared without degassing with helium gas using DSS-d$_6$ as an internal NMR standard.

Gene Expression Analysis

Gene expression of glutamate-cysteine ligase catalytic subunit (GCLC) and glutathione synthetase (GSS) was determined by estimating their mRNA level using real-time quantitative polymerase chain reaction (qPCR). Test and control cells were collected, and total RNA was isolated using RNeasy RNA isolation kit (QIAGEN Cat #74104). cDNA synthesis was done with equal amount of RNA from all samples using high capacity cDNA reverse transcription kit (Applied Bio Cat #4368814). Real-time qPCR was performed using TB Green Premix Ex Taq II (Tli RNase H Plus) with the following cycles: 95° C. 30 s, 40 cycles of 95° C. for 5 s and 60° C. for 30 s. Standard $2^{-\Delta\Delta Ct}$ method was used for calculating fold changes in gene expression. Primers used for qPCR were as follows: GCLC sense 5'-CCAAGTCCCTCTTCTTTCCTG-3' antisense 5'-CGGAGACGGTGT ATTCTTGTC-3', GSS sense 5'-AGC-CAATGCTCTGGTGCTAC-3' antisense 5' ACCTTCGACGGATTACATGG-3', RPL8 (internal control) sense 5'-CCATGAATCCTGTGGAGC-3' antisense 5'-GTAGAGGGTTTGCCGATG-3'.

GSH, GSSG, GSS, and GCLC Measurements

Figure 35A:
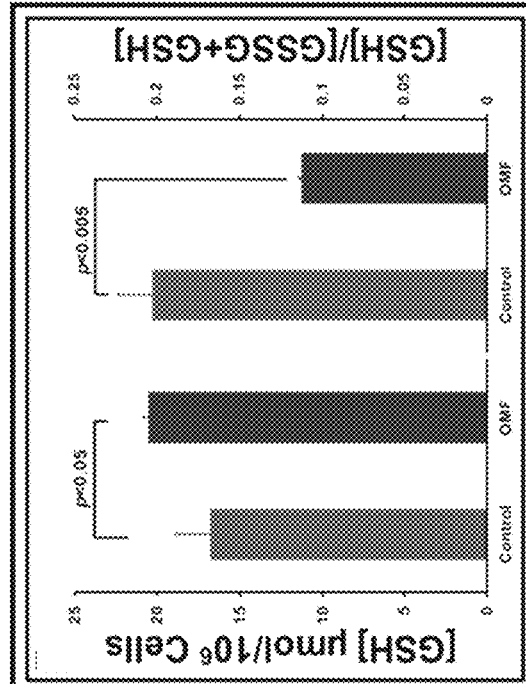
FIGS. 35A-D illustrate certain ratios between measured GSH, GSSG, GSS, and GCLC levels.
Figure 35B:
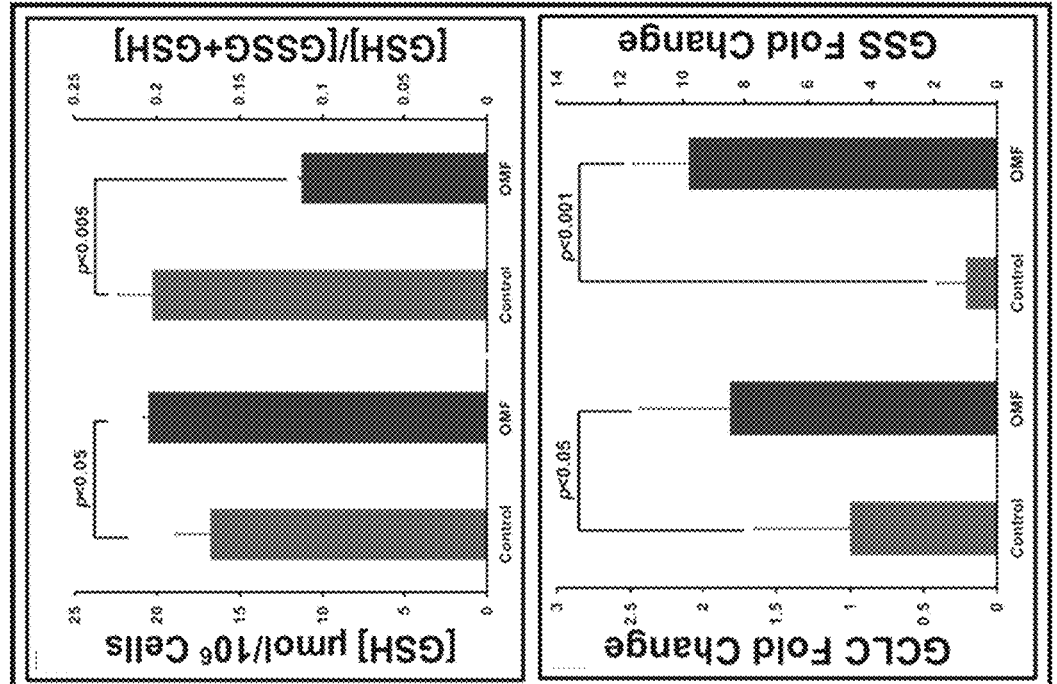
Figure 35C:
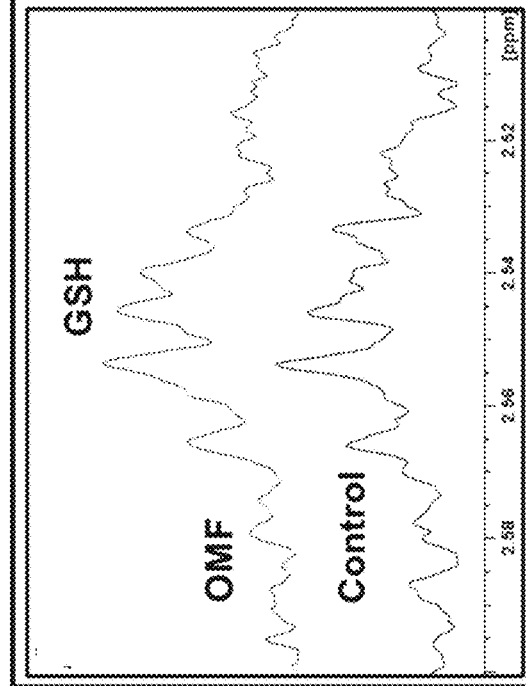
Figure 35D:
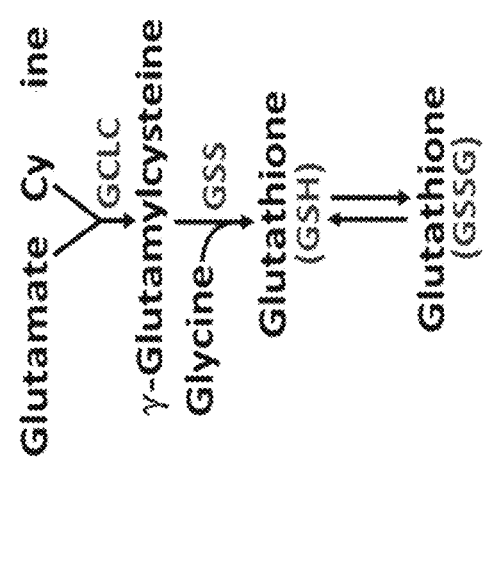
Figure 36:
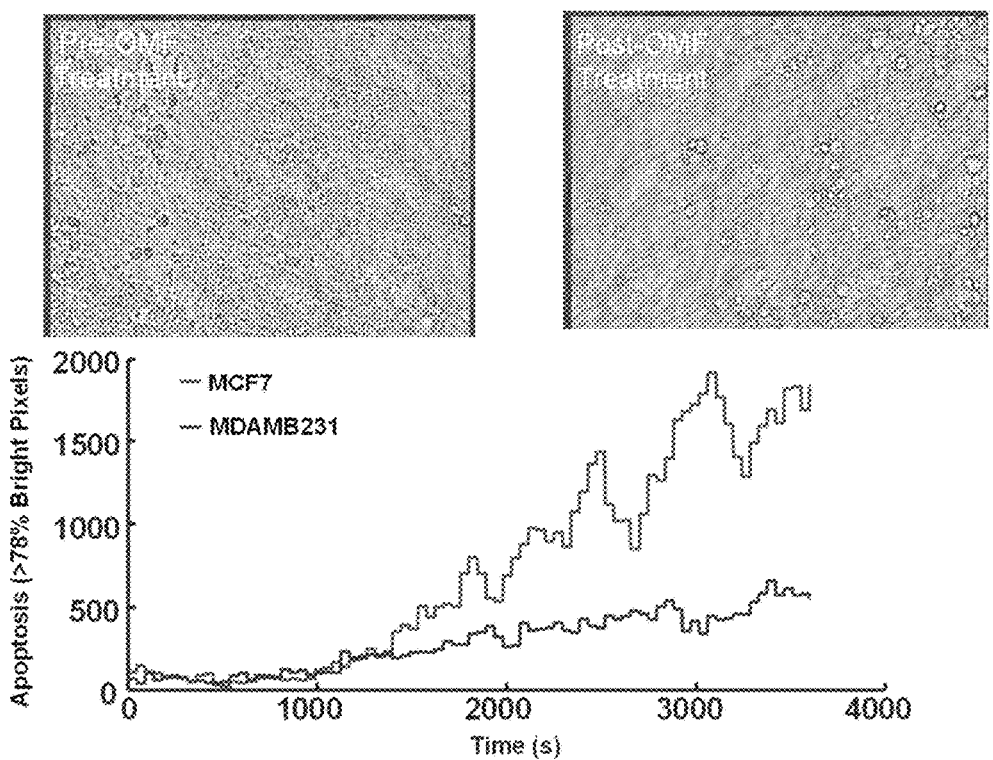
FIG. 36 shows cell death in two different breast cancer cell lines with OMF. Top. Photomicrographs of MCF7 (ER+) and MDA-MB-231 (triple-negative) breast cancer cells pre (left) and post (right) 2 h stimulation treatment with OMF. Bottom. Graph showing an increase in bright pixels (>78% brightness) indicating apoptosis or cell death.

As discussed above, OMF treatment generates ROS in the form of both superoxide and hydrogen peroxide in GBM cells. Cells can counteract the toxicity of ROS by upregulating their antioxidant defenses, the majority of which are dependent on GSH. An examination of GSH levels showed that there was a 20% elevation in treated cells, as illustrated in FIGS. 35A and 35B. However, when the reduced/oxidized glutathione (GSH/GSSG) ratio was examined in these same cells, it was found that the OMF treated cells were much more oxidized, with GSH/GSSG ratio almost exactly half that seen in control cells, p<0.005. FIG. 35C shows that GCLC and GSS are the key enzymes in the GSH biosynthesis. Therefore, the mRNA levels of transcripts of these enzymes using qPCR, in treated and untreated cells, were examined. There was a two-fold increase in GCLC mRNA levels after OMF treatment, and the levels of GSS, generally believed to be rate-limiting for GSH synthesis, were elevated eight-fold, as illustrated in FIG. 35D.

The OMF stimulation can substantially alter GBM cancer cell mitochondrial metabolism, in a manner similar to that seen in cells with deficits engineered in either Krebs cycle enzymes or respiratory complexes. The perturbation of mitochondrial function generally results in an increase in mitochondrial ROS production. This could explain the observed collapse of the GSH/GSSG ratio in OMF treated cells. ROS generated by OMF could oxidize GSH and generate higher steady state levels of GSSG. The resultant change in the GSH/GSSG ratio would activate 'redox switches' that initiate the GSH synthesis pathway.

Animal Studies

Four animal studies were conducted for evaluating efficacy using Oncomagnetic therapy, all utilizing FOXN1-Nude immunodeficient mice implanted with patient derived GBM tumor cell xenografts. A randomized equal number of animals to treated and untreated cohorts were used.

Figure 37:
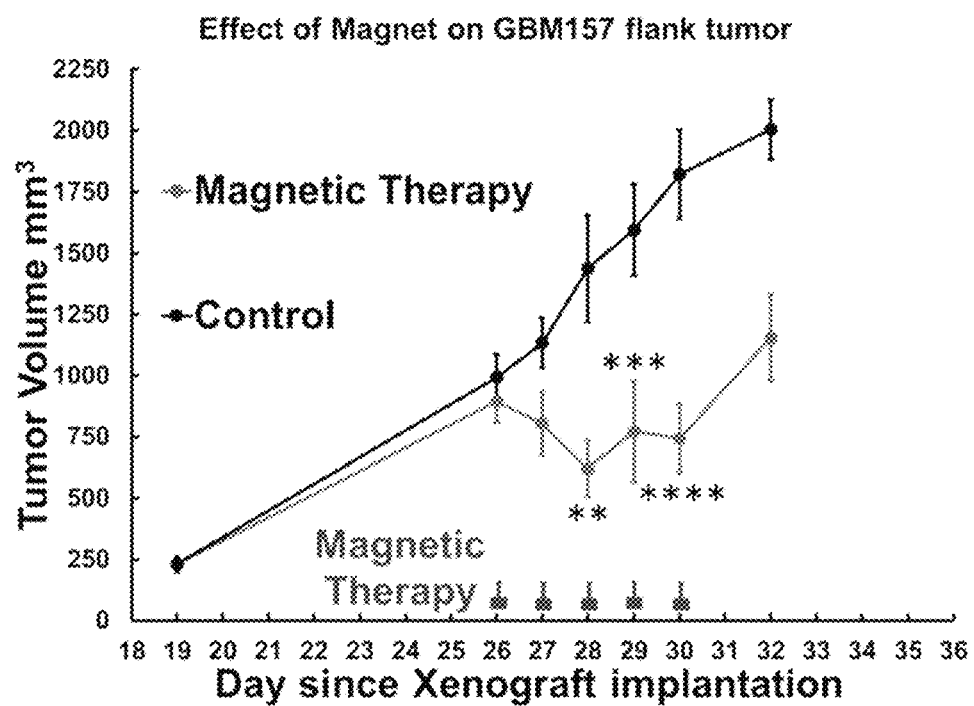
FIG. 37 shows Treatment of Flank Implanted GBM in Immunodeficient Mice. Time course of change in flank implanted GBM tumor volume in response to sOMF therapy (Magnetic Therapy). 4 h stimulations were done each day for 5 days. There was significant reduction in manually measured tumor volume in treated mice compared to unstimulated mice (Control).

In the first of these studies the effect of treatment on 10 mice with flank GBM primary tumors in a xenograft model was examined Mice received 4 hours of magnetic stimulation for 5 days. This treatment caused an initial shrinkage of tumor volume (FIG. 37), slowed further tumor growth, and extended median animal survival by a factor of two compared to equal number of untreated control animals.

Figure 38:
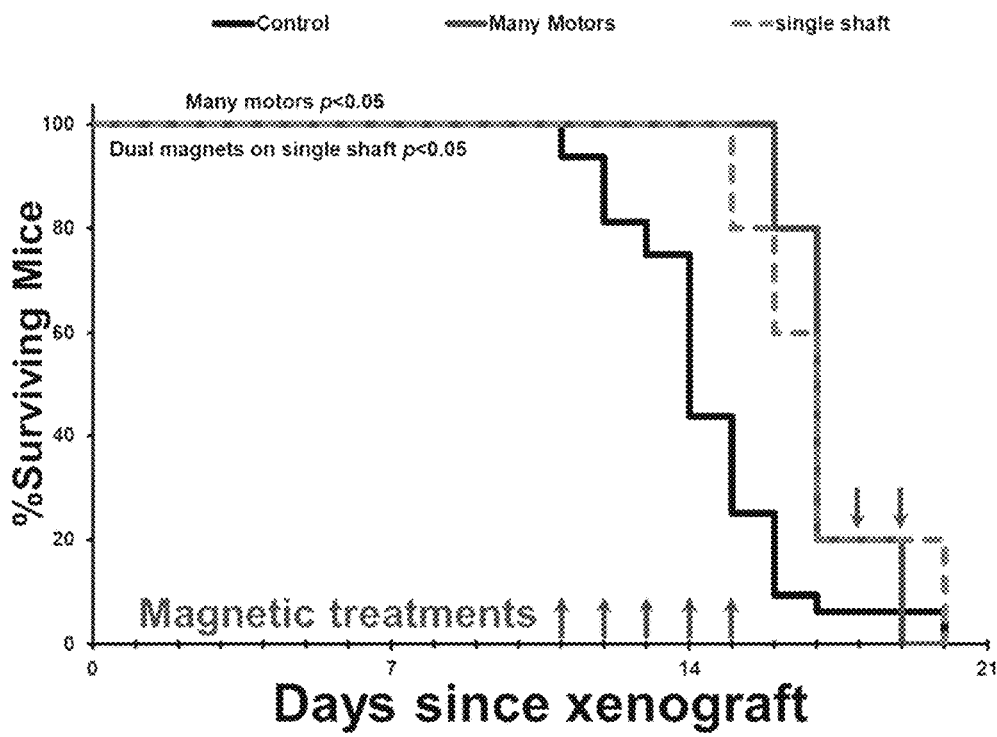
FIG. 38 shows the effect of Two Different Methods of Oncomagnetic Treatment on Late Stage GBM Xenografts in Immunodeficient Mice. Kaplan-Meier plot shows significant prolongation of survival in this late stage model. An increase in median survival of three days is seen with both types of treatment in treated mice compared untreated controls.

In the other three studies mice that received intracranial GBM xenografts were used. The intracranial tumor cell implantation was carried out as described previously. The second study involved daily 4 hour treatment of late stage tumor beginning on the 10$^{th}$ day after implantation for 5 days, using two different methods of stimulation. The two methods were: 1) use of a single large oncoscillator surrounded by a circular plexiglass maze containing 8 mice; and 2) use of 27 small oncoscillators attached to a straight single arm maze (9 equidistantly spaced oncoscillators on each of three sides) containing 8 mice. Both types of treatment showed significant increase in the duration of survival compared to untreated control mice with tumors (FIG. 38). The median survival in both cases was prolonged by 3 days.

Figure 39:
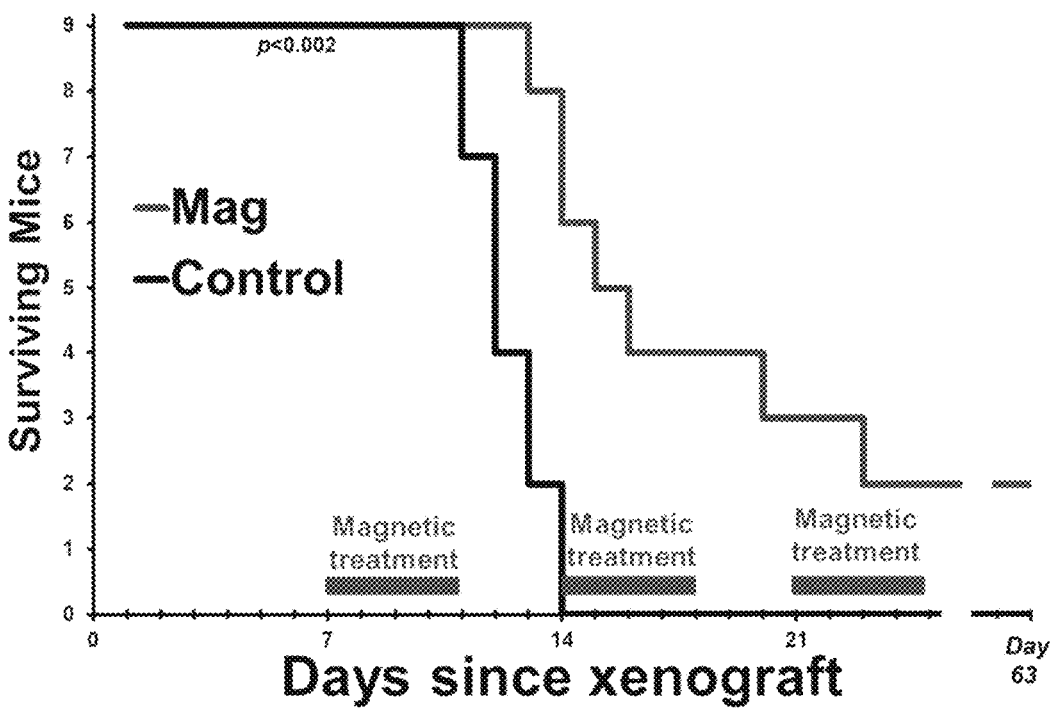
FIG. 39 shows treatment of GBM Xenografted Immunodeficient Mice with the Straight Maze Method with Large Oncoscillators. Kaplan-Meier plot shows significant prolongation of survival of treated mice compared to controls, with an increase in median survival of four days and continuing survival of 22% of treated mice post-treatment at day 63.

The third study used only the straight maze method of treatment with 4 equally spaced large oncoscillators like those used in the human use device attached to the roof of the maze. A total of 9 treated mice were compared with an equal number of untreated control animals. The treatment was started 7 days after tumor cell implantation. It consisted of 4 hour stimulation per day, 5 days a week, for three weeks. A statistically significant 4-day shift in median survival during treatment was observed compared to control tumor-laden mice that were not treated (FIG. 39). All control animals reached the terminal end point by 14 days after implantation. Two animals in the treatment group (22%) are still alive on day 63, even after termination of treatment on day 25.

Figure 40:
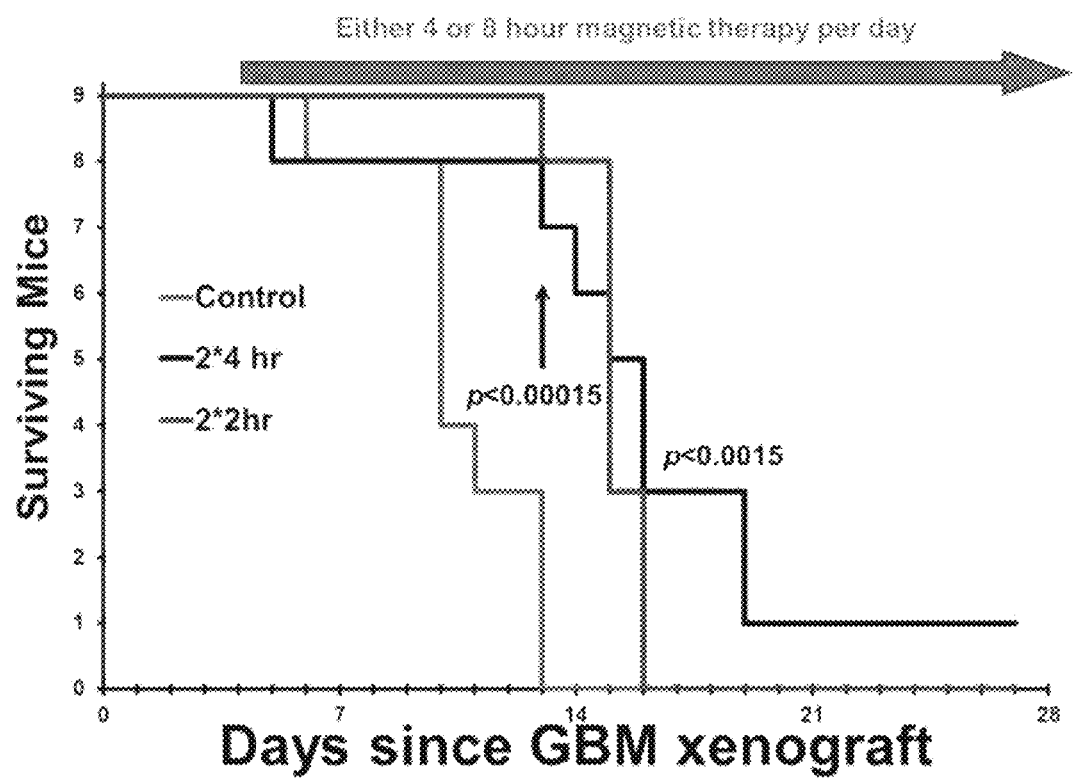
FIG. 40 shows treatment of GBM Xenografted Immunodeficient Mice in Home Cages with Two Regimens using Large Oncoscillators. Kaplan-Meier plot shows significant prolongation of survival. Increases in median survival compared to untreated controls are of four and five days with 2-hour twice daily and 4-hour twice daily treatments, respectively. One mouse in the 4-hour group is still alive on day 27.

In the fourth study xenografted mice were treated in their housing cages by stimulating each cage from the bottom with two large human use-type oncoscillators. Two treatment regimens were used and treated the mice daily for 24 days starting on day 4. The regimens were 2-hour or 4-hour stimulation every 12 hours each day. A total of 9 mice were randomized to each treatment arm and one control arm. FIG. 40 shows that both treatment groups survived significantly longer than the control group. The 2-hour group showed 5-day increase in median survival, while the 4-hour group showed a 6-day prolongation. All control mice reached their terminal end point on day 13. The 2-hour group reached it on day 16. One mouse from the 4-hour treatment group is still alive on day 27.

Methods and materials used in the experiments related to rotating magnetic fields discussed above:

Bongkrekic Acid) was dissolved in DMSO and used to a final 0.1% v/v ratio. Mice were obtained from Charles River Laboratories, Inc. Lemon tree leaves were harvested from first authors garden, and chopped into <0.5 mm squares, before being placed in PBS supplemented with 35 mM $NaHCO_3$. The leaf fragments were illuminated with a 'cool' white light source, a Series 180 Fiber-Light® high-intensity illuminator, via an infra-red absorbing optical fiber.

Human tissues: Glioma, diffuse intrinsic pontine glioma (DIPG) and meningioma tumors and resulting cultures used were from de-identified patient tissues and have no identifiable private information.

Oxygen electrode data collection: A thermostatically controlled (37° C.), water-jacketed, glass-walled, Clark-type O2 electrode was used throughout. Data were collected electronically with a PicoLog® High Resolution Data logger and exported into ImageJ to generate the traces shown in FIGS. 18C-18D; 19A-19C; 20A-20B; 21A-21B; and 22A-22B. The oncoscillator was attached to the end of a microphone stand and was held perpendicular to the outer glass wall of the electrode, so that there was an air gap of ≈5 mm between the two devices. There was a degree of crosstalk between to stirring bar of the O2-electrode chamber and the oncoscillator; this interaction manifests itself as jumps or drops in the apparent O2 concentrations at the beginning or the end of OMF stimulation. This interaction was found to be at its greatest when the stirrer bar was used at the high speeds typically used to ensure a rapid electrode response rate. The stirrer velocity was therefore optimized to negate the interaction with the oncoscillator.

Preparation of mitochondria: Rat liver mitochondria (RLM) were prepared according to standard methods (Chappell & Hansford) in a medium containing 150 mM sucrose, 10 mM KPi buffer, 25 mM K-HEPES buffer, pH 7.4, 37° C. The mitochondrial protein was assayed using the Pierce™ BCA Protein Assay Kit with bovine serum albumin as a standard and RLM were used at 0.2 mg. Sodium succinate (5 mM) was added as substrate. Mitochondria showed RCI's of ≥4.0 using glutamate/malate as substrates.

Tumor culture preparations: GBM and meningioma tumors were taken at the time of (first) excision and given the laboratory ID. They were washed in PBS, chopped with a scalpel and homogenized in a BeadBug™ homogenizer using 1.5 mm Zirconium beads, in an equal volume of PBS. A DIPG tumor sample, identified as being a K27MH3 mutant, was collected from an adolescent, post-autopsy, following storage in liquid nitrogen after flash freezing. The homogenates were grown in DMEM with 20% FBS, 1U GlutaMax™, sodium pyruvate (1 mM), penicillin (100 U/ml), and streptomycin (100 mg/ml). The DIPG and meningioma cells were used at this passage. GBM cells were grown from third passage cells and used after the first expansion.

Normal human astrocytes (NHA) were grown to confluency in astrocyte cell basal medium supplemented with 3% FBS and the contents of Lonza Clonetics™ AGM™ BulletKit.

Cells were grown to confluency, counted, harvested using trypsin, washed in ice-cold PBS and stored on ice at $8 \times 10^9$ cells/ml. O2 consumption of cells was measured in PBS, 10 mM glucose, 37° C. 2 µM carbonyl cyanide trifluoromethoxyphenylhydrazone.

According to a certain setup, cells grown in 96-well cell culture plates were OMF stimulated, sham stimulated or unstimulated for 4 h inside humidified $CO_2$ incubator. Paraformaldehyde (4% w/v in PBS) was used for fixation and DAPI was used for staining nuclei. Ethidium Homodimer-1 was used to stain dead cells. Live and dead cell images were captured at 10× magnification on a Nikon Eclipse TE2000-E microscope and analyzed with NIS-Element program or a Carl Zeiss Axio Observer microscope with an onstage incubation chamber having a humidified 5% $CO_2$ supply. Live or dead cell counts for each cell type in an experiment were averages obtained from one representative central field from each of 8-12 wells. Staining reagents or drugs were added in the media 1 h before OMF or no stimulation treatment. Statistical comparison of live and dead cell counts between no stimulation and OMF treatment conditions was done using Student's two-tailed pooled t test. The p value for significance was set at 0.05.

Cell Culture and Reagents

Human GBM cells (BT175, BT115 and BT157) were derived from tumors surgically excised from patients by one of the authors (DSB) in 2015 (see NOTE A below). Informed consent was obtained from all patients in accordance with an approved Houston Methodist Research Institute (HMRI) Institutional Review Board (IRB). These cells were grown in DMEM with 20% FBS, 1 U GlutaMax™, sodium pyruvate (1 mM), penicillin (100 U/ml), and streptomycin (100 mg/ml). U87 GBM cells, SVGp12 astroglial cells, human cortical neurons (HCN-2) and A549 lung cancer cells were grown in DMEM with 10% FBS. Normal human astrocytes (NHA) were grown in astrocyte basal media. All cell lines were incubated at 37° C. temperature inside humidified incubator with 5% $CO_2$.

OMF Stimulation

Malignant and normal cells were exposed to OMF generated by oncoscillators. In the experiments described herein the oncoscillators were positioned such that the cells were exposed to a peak-to-peak rotated magnetic field of 1-58 mT strength. In the initial experiment (FIG. 41) in BT175 GBM cells the applicant systematically varied intermittently delivered OMF patterns in peak frequency (PF; 50-350 Hz), pulse train duration (TD; 50-1000 ms), inter-pulse train off intervals (TI; 92-2000 ms) and total exposure time (ET; 2-4 h). The results obtained under these intermittent exposure conditions were compared with continuous OMF exposure at a peak frequency of ~350 Hz for 2 h. In a control set of experiments the applicant exposed cells to sham treatment or no OMF treatment at all. The sham treatment involved ineffective oncoscillators that rotated non-magnetic metallic or plastic rods in the same way as the OMF producing magnets. During and up to 4 h after the end of active, sham or no treatment, the applicant video-recorded (time-lapse serial images) OMF effects on unstained GBM cells under a microscope. For stimulating cells under the microscope, the oncoscillator was held by a microphone stand.

OMF stimulations in live and dead cell count experiments were carried out using a specially constructed apparatus consisting of an array of OMF oncoscillators that delivered the desired OMF exposure to a cell/tissue culture plate (NOTE A below). In all experiments the oncoscillators were connected to a device controller operated by a rechargeable battery and triggered by an application on a Bluetooth-connected electronic tablet. Exactly similar experimental setups were used to provide active and sham exposures.

Cell Viability and Death Assays

Cells grown in 96-well cell culture plates were OMF stimulated, sham stimulated or unstimulated for 4 h inside humidified $CO_2$ incubator. Paraformaldehyde (4% w/v in PBS) was used for fixation and DAPI was used for staining nuclei. Ethidium Homodimer-1 was used to stain dead cells. Live and dead cell images were captured at 10× magnification on a Nikon Eclipse TE2000-E microscope and analyzed with NIS-Element program or a Carl Zeiss Axio Observer microscope with an onstage incubation chamber having a humidified 5% $CO_2$ supply. Live or dead cell counts for each cell type in an experiment were averages obtained from one representative central field from each of 8-12 wells. Staining reagents or drugs were added in the media 1 h before OMF or no stimulation treatment. Statistical comparison of live and dead cell counts between no stimulation and OMF treatment conditions was done using Student's two-tailed pooled t test. The p value for significance was set at 0.05.

Mitochondrial ROS Detection and Caspase Activation Assay

Cells grown in Petri dishes were treated with 10 μM MitoSOX™ Red or with 5 μl/ml NucView Caspase-3/7 Green Detection Reagent in growth media. Following 1 h treatment the cells were washed with PBS and then treated with OMF, sham stimulation or no stimulation for 2 h on the microscope stage. Time-lapse fluorescence images captured during OMF treatment and for several hours after treatment were assembled into videos.

Flow Cytometry for Determination of OMF-Induced Changes in ROS Levels

Cells grown in Petri dishes were exposed to OMF for 1 h (250 ms TD and 750 ms TI). Immediately after stimulation the growth media were replaced with 50 μM 2',7'-Dichlorofluorescin diacetate (H2DCFDA) containing media and incubated at 37° C. in a humidified atmosphere containing 5% $CO_2$ for 1 h. Cells were harvested using trypsin and fixed with ice cold 4% paraformaldehyde for 10 min. Fluorescence signal from cells was acquired using BD LSR Fortessa flow cytometer.

Mitochondrial Morphology

Coverslips with cells were transferred into the same media that contained either 500 nM MitoTracker™ or 5 μM MitoSOX™ for 30 minutes prior to transfer. Then coverslips were placed into a temperature regulated perfusion chamber, with the growth medium maintained at 37° C. using a Warner Instrument Corp TC-344B temperature controller. Images were captured using a Nikon Eclipse TE2000-E at 60× or 90× magnification with a CoolSnap ES digital camera system containing a CCD-1300-Y/HS 1392-1040 imaging array.

Immunofluorescence Staining

HCN-2 and NHA cells grown on 16-well chamber slides were fixed with 4% paraformaldehyde and permeabilized with 0.1% Triton-X100 in PBS. Permeabilized cells were stained with anti-microtubule-associated protein 2 (MAP2) antibody (ab5392) and anti-chicken secondary antibody diluted in Dako antibody dilution buffer. DAPI was used for staining the nuclei. Images were captured as described earlier.

Estimation of Intensity in Videos (Time-Lapse Serial Images)

Intensity in time-lapse video micrographic image frames was obtained by importing the video files into MATLAB programming environment. The imported serial images were processed using a MATLAB script written in house, which measured the normalized intensity or brightness above a common threshold across all images and conditions. Mean intensity or percentage of pixels above the threshold was then plotted as a function of time and compared across conditions.

Mouse Xenograft Model Study

Intracerebral implantation of patient derived BT157 GBM cells was done in 27 FOXN1-Nude mice. Mice received OMF stimulations in their housing cages from the bottom with two oncoscillators for each cage. One of two treatment regimens was delivered to two groups of 9 mice each for 24 days starting on day 4. The two regimens were 2 h or 4 h stimulation every 12 h each day. The control group of 9 mice did not receive OMF stimulation. Overall survival of mice in each group was compared using the Kaplan-Meier survival statistic, in which the $\chi2$ distribution (1 degree of freedom) is calculated from the log rank test.

Exposure to OMF Causes Cancer Cell Death

Figure 41:
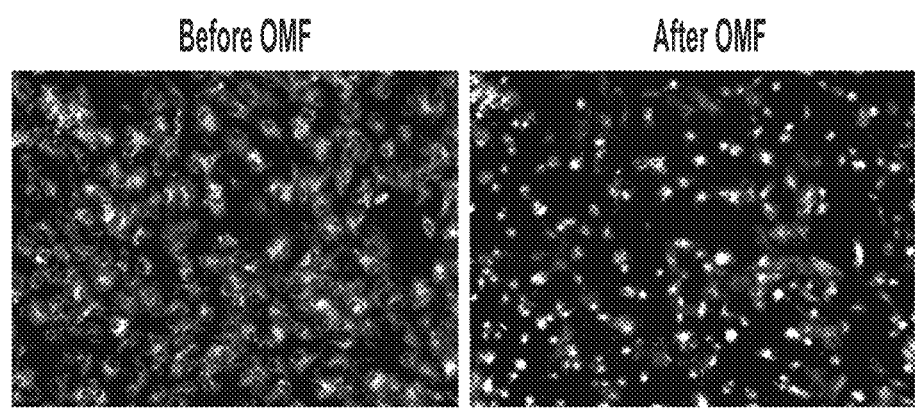
FIG. 41 show morphological changes and measurement of apoptosis of malignant and normal cells treated with OMF treatment. MitoTracker fluorescence images showing breakdown of mitochondrial network structure in GBM cells after 40-min OMF treatment compared to before such treatment. These GBM cells were in G0 phase (resting and non-dividing) of the cell cycle caused by 48 h incubation in FBS-free medium.

FIG. 41 shows that OMF stimulated cells grown in the absence of fetal bovine serum and stained with MitoTracker exhibit the mitochondrial morphology of cells that are about to undergo apoptosis. This result demonstrates that the oncolytic effect is not restricted to dividing cells, unlike TTF therapy.

Other OMF treatment parameters show qualitatively similar effects on cell morphology as above but vary quantitatively from ~70-120 min in time course, as seen in the intensity plot in FIG. 28. This effect, however, occurs only if the active treatment involves intermittent exposure to OMF and not if the cells are exposed to OMF continuously over the same ET of 2 h (FIG. 28). It also does not occur in the sham-treated, static magnetic field (unrotated magnet) and untreated conditions (FIG. 28).

No Cytotoxic Effect in Normal Cells

Figure 42:
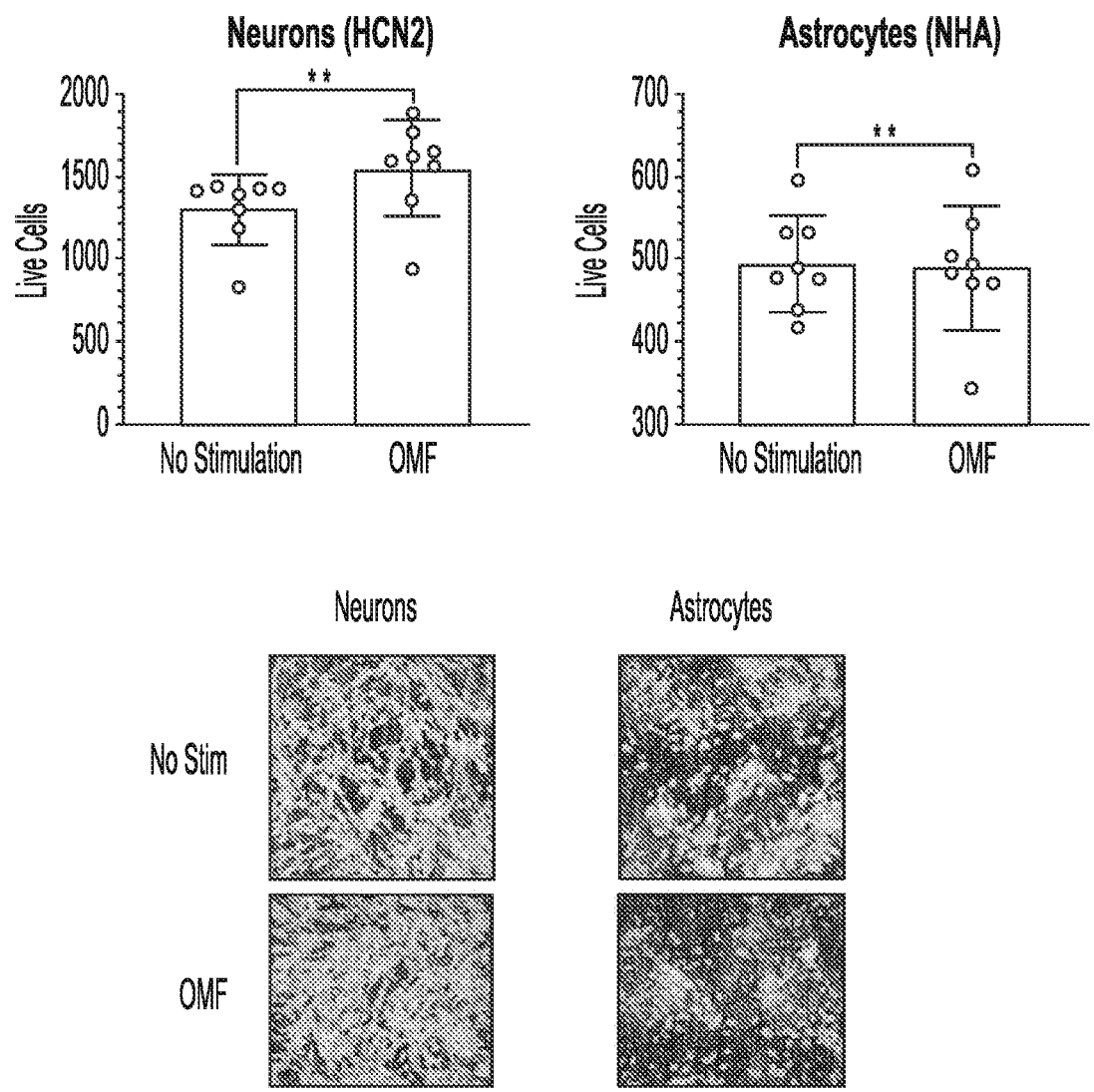
FIG. 42 shows the effects of OMF treatment on normal human cortical neurons and astrocytes (No cytotoxic effects of OMF on normal human cortical neurons and astrocytes). Top panel shows bar plots demonstrating no significant decrease in live cell counts in human cortical neurons (n=8) and astrocytes (n=8) 24 h after 4 h OMF stimulation. There is a small but significant (p=0.037) OMF-induced increase in neurons. Bottom panel shows representative photomicrographic fields containing DAPI and MAP2-stained neurons and astrocytes.

OMF treatment of cultured normal human astrocytes (NHA), cortical neurons, and bronchial epithelial cells (hBEC) show no morphological changes indicative of apoptosis. There is a corresponding lack of cell death, which is reflected in no reduction in cell counts with OMF treatment (FIGS. 42 and 43). There is no significant difference in the number of DAPI-stained live cells between unstimulated and OMF-stimulated cells, 24 h after 4 h OMF stimulation. The neuronal cells show a small but significant post-OMF stimulation increase in live cells (FIG. 42-A, top panel). There are also no detectable morphological changes in both types of cells immunostained for MAP2 (FIG. 42, bottom panel). In fact, with NHA one can observe an OMF-induced protective effect against the time-dependent toxicity of singlet oxygen produced by MitoTracker fluorescence, a mitochondrial membrane potential probe that reveals mitochondrial damage in dying cells. FIG. 42 (bottom panel) shows the morphology of NHA in the two conditions at the same time-point. There is intense staining due to mitochondrial disruption in sham-treated but not in OMF-treated cells at this time-point.

Quantification of OMF-Induced Cell Death

FIG. 543A illustrates a bar plot showing ~34% reduction in cell count (p=$8.6 \times 10^5$, n=12) in DAPI-stained BT175 GBM cells 24 h after a 4 h OMF stimulation session. Representative photomicrographs of DAPI-stained cells under the OMF stimulated and unstimulated conditions are shown on the right side of the plots in all panels in this figure. The horizontal calibration bar is 100 in length.

To quantify the oncolytic effect of OMF, the applicant counted surviving DAPI-stained GBM cell nuclei in cell culture (average of 8-12 fields at 10× magnification, representative photomicrographs shown in FIG. 43), 24 and 48 h after 4 h OMF stimulation.

FIG. 43 illustrates a bar plot showing ~60% decrease in cell count (p=$1.8 \times 10'$, n=6) in A549 non-small cell pulmonary carcinoma cells under the same conditions as above. FIG. 43C illustrates a bar plot (left panel) showing ~20% decrease in cell count in another more rapidly growing cell line of GBM, U87, under the same conditions as above (p=0.002, n=7). The reduction in cell count increases to ~52% (right panel) when the total OMF stimulation is for 8 h (two 4 h sessions 24 h apart, p=3.2×10-5, n=8). FIG. 43D illustrates a bar plot showing no decrease in cell counts in normal human bronchial epithelial cells (right, n=8). FIG.

43E illustrates bar plots that show increases in ethidium homodimer-labeled human (BT115, p=0.014) and mouse (GL261-Luc2, p=0.023) dead GBM cells after 4 h treatment with OMF.

Figure 43A:
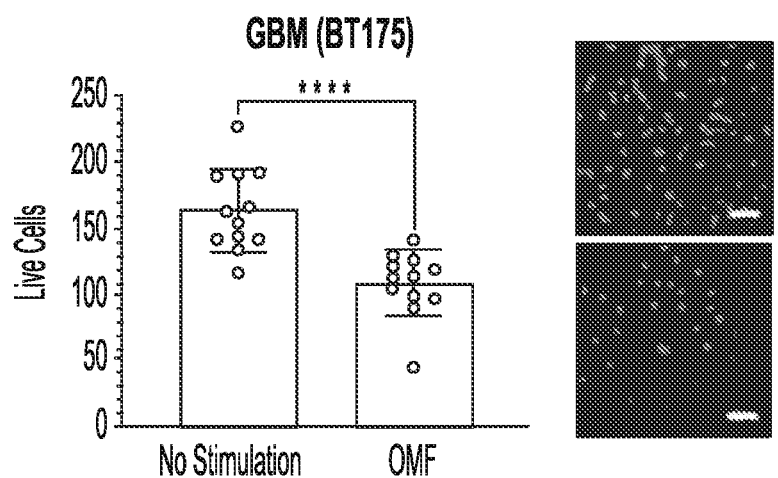
FIGS. 43A-43E show the decrease in cancer cell counts following OMF treatment.
Figure 43B:
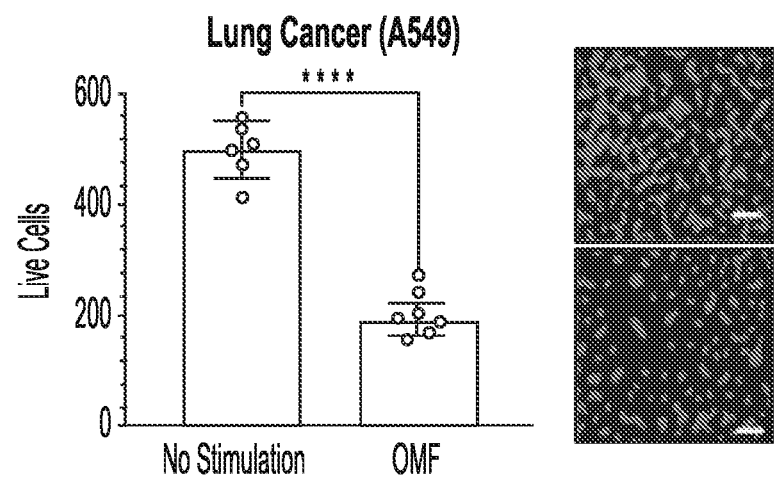
Figure 43C:
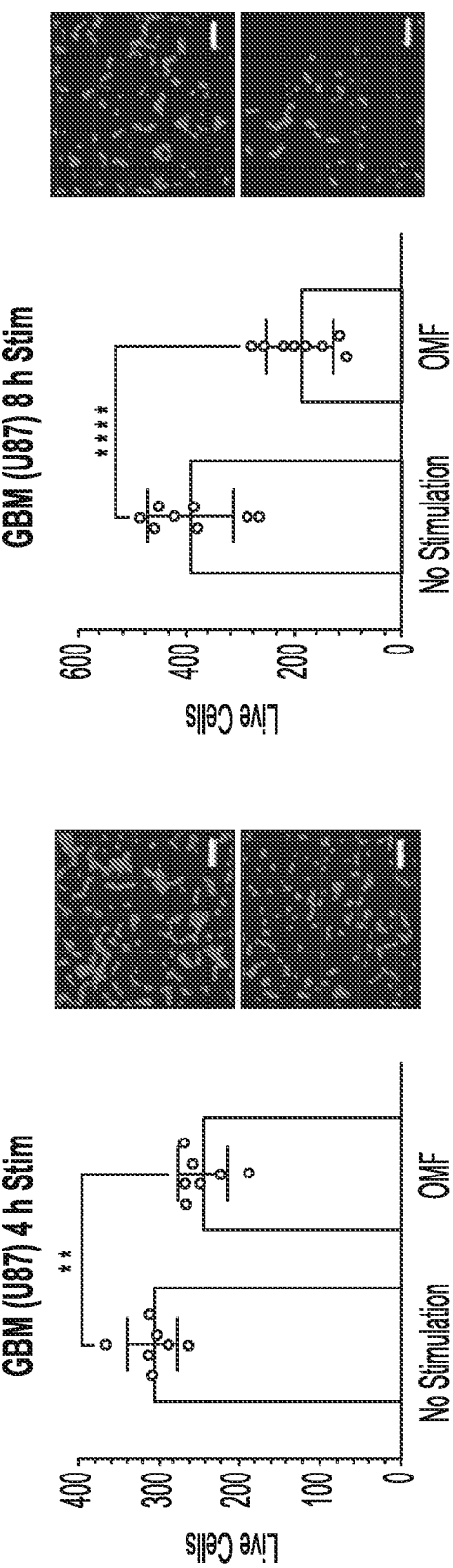
Figures 43D, 43E:
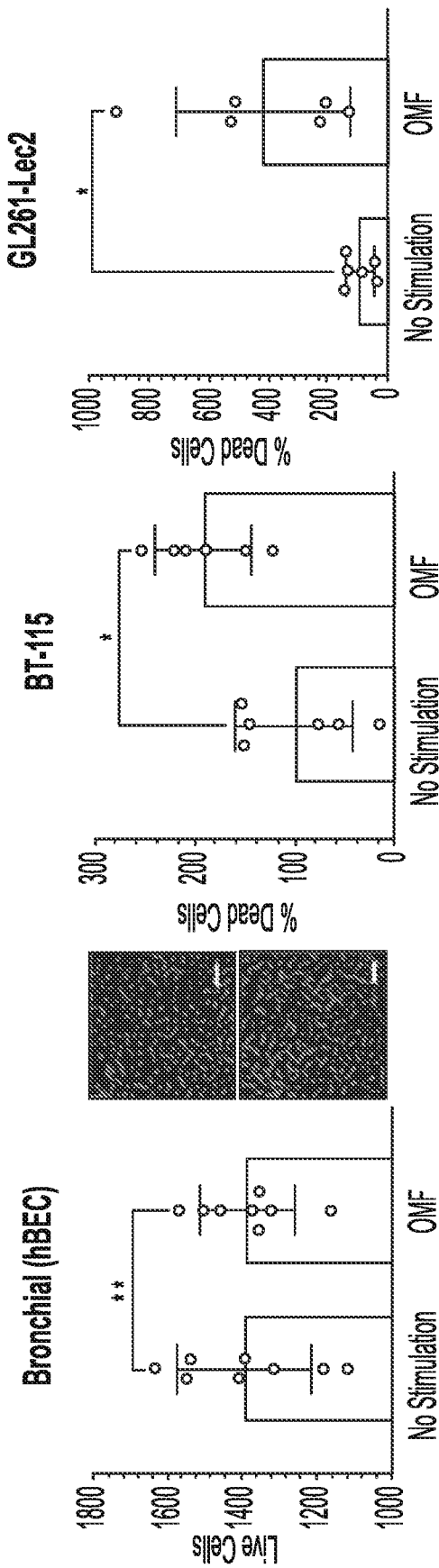

FIG. 43A shows a ~34% reduction in cell count after 24 h. In A549 non-small cell lung carcinoma cells the decrease in cell number after 48 h is ~60% (FIG. 43B). The applicant also tested whether the effect of multiple OMF exposures on successive days was cumulative. This was important to know because during the long pause between the end of stimulation and counting of cells the surviving cells could proliferate and artifactually reduce the observed killing effect of OMF. For this experiment the applicant used a different GBM cell line (U87) because it proliferates faster. In FIG. 43C one see that 24 h after one 4 h session of OMF exposure there is only ~20% decrease in cell count of these cells. However, the count decreases by more than 50% after two 4 h OMF stimulation sessions on successive days. FIG. 43D shows that OMF does not cause a decrease in normal hBEC counts. It was confirmed that the decrease in live cell count in malignant cells is indeed due to cell death by directly counting ethidium homodimer-labelled dead cells (BT115 human GBM and GL261-Luc2 mouse GBM cells) and observing their increase compared to unstimulated control after 4 h OMF exposure (FIG. 43E).

Test of an Alternative Hypothesis of ROS Generation

Magnetically influenced RPM plays a role in ubiquitously expressed flavoproteins called cryptochromes, which can also generate ROS when perturbed by magnetic fields. Cryptochrome agonists have been recently shown to inhibit cancer stem cell proliferation in GBM. This alternative possibility for generation of ROS by OMF was tested. To do this surviving cells were counted after two 4 h sessions of OMF stimulation over 24 h in the presence and absence of a cryptochrome antagonist, KS15. Data shows that there is a significant partial attenuation of the decrease in cell count produced by OMF when cryptochromes are inhibited.

OMF-Induced Prolongation of Survival in a Mouse Xenograft Model of GBM

Data shows that immunodeficient mice with human intracerebral GBM tumor xenografts in two treatment groups stimulated with OMF for 2 or 4 h twice daily for 24 days survived significantly longer than the unstimulated control group. The 2 h group showed 5-day increase in median survival (p<0.00015), while the 4 h group showed a 6-day prolongation (p<0.0015). The last control mouse reached its terminal end point on day 13. The last mouse from the 2 h group reached it on day 16. One mouse from the 4 h treatment group has survived beyond day 300.

The above experiments that short exposures of patient derived GBM cells to intermittent OMF patterns produced by rotating magnets, using the oncoscillators of an Oncomagnetic device, produces rapid (as early as ~2-4 h) apoptosis. The physical parameters of OMF shown to produce this effect include frequencies rising to and falling from a peak frequency in the super-low frequency range (100-300 Hz) and amplitudes in 1-58 mT range. Another cancer cell type (non-small cell lung cancer) is also similarly susceptible to OMF exposure. However, OMF treatment does not have toxic effects on normal cells, such as normal human cortical neurons, astrocytes, and bronchial epithelial cells. The underlying mechanism involves a marked increase in ROS, mitochondrial membrane depolarization, fragmentation of mitochondrial network and activation of caspase 3. These results are consistent with OMF-induced disruption of the electron flow in the mitochondrial electron transport chain through RPM. Furthermore, it is believed that electron transfer in cryptochromes might also be altered by OMF, contributing to increased ROS within cancer cells. It can be surmised that the selective apoptosis in cancer cells, but not in normal cells, is likely due to the fact that cancer cells have abnormally high levels of ROS34 that are poised on the threshold of apoptosis if accentuated further with a targeted ROS-inducing treatment such as OMF. The anticancer effect of OMF was confirmed in vivo in a mouse GBM xenograft model.

FIG. 44 include histograms showing the distribution of H2DCF-stained GBM (U87) (left panel) and normal astroglial (SVGp12) (right panel) cells plotted from flow cytometric data. The percentage of cells is plotted with respect to the normalized fluorescence intensity (intensity/width of forward scatter).

Figure 45A:
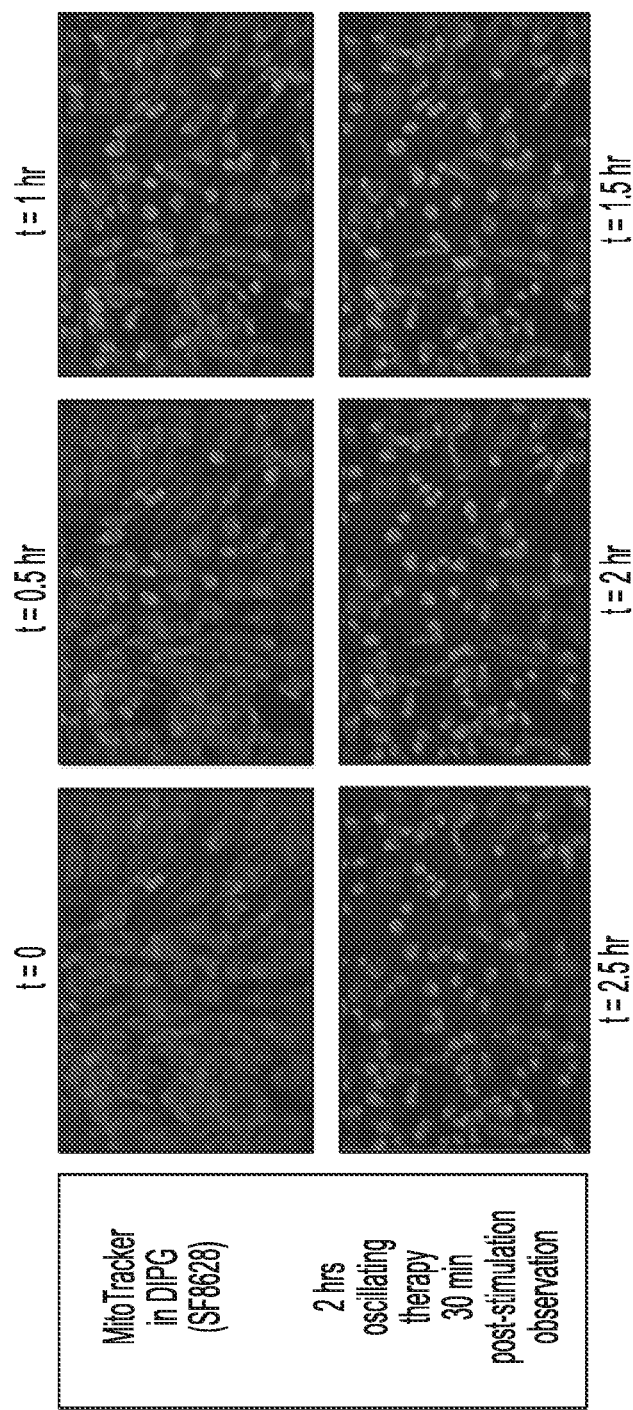
FIGS. 45A-45C illustrate the effect that rotating fields have on cultured SF8628 DIPG cells.
Figure 45C:
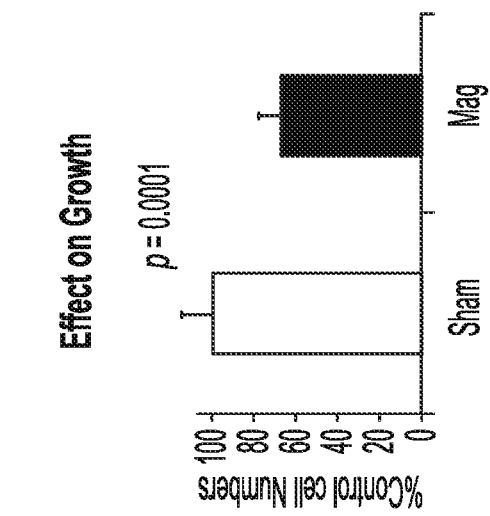
Figure 45B:
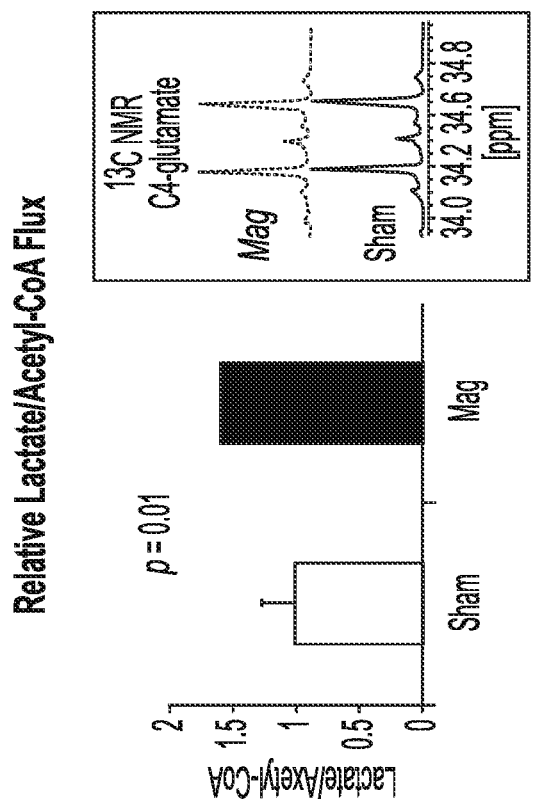

FIGS. 45A-45C illustrate the effect that rotating fields have on cultured SF8628 DIPG cells. Cells loaded with MitoTracker™ were subjected to OMF stimulation for 2 hours, and then observed for a further 30 minutes, at which time simultaneous cell death was observed, SF1A. SF8628 cellular carbon flux was also examined in preliminary experiments using 1H & 13C NMR in cells incubated with 13C-glucose, with cells subjected to 4 hours of OMF or SHAM stimulation. OMF stimulation caused an elevation of flux from glucose into lactate and a decrease in mitochondrial carbon flux from 13C-glucose derived acetyl-CoA. OMF stimulation resulted in the mitochondrial carbon flux falling by ≈25% and the lactate flux rising by ≈16%, and OMF treatment raised the anaerobic/aerobic flux of these DIPG cells by ≈60%, p=0.01, SF1B. In growth studies the effects of 4 hours of OMF or SHAM stimulation, were examined on living SF8628 DIPG cell numbers assayed 44 hours later. Using this regime, a ≈40% drop in viable cells was observed, p<0.0001, SF1C.

Note A

In one study, all patient derived GBM cell lines used were obtained from tumors diagnosed as Grade IV astrocytomas by clinical neuropathologists at our hospital. The tumors were classified as isocitrate dehydrogenase 1 (IDH1) wild-type. BT175 was a newly diagnosed GBM described as an infiltrating glial neoplasm with marked nuclear variability and frequent mitotic figures. BT115 had unmethylated O-6-methylguanine-DNA methyltransferase (MGMT) methylation status and did not show epidermal growth factor receptor (EGFR) amplification. BT157 was obtained from a patient who had recurrent GBM. The GBM cells were spontaneously immortalized.

Implantation of Human GBM Xenografts in Immunodeficient Mice

FOXN1-Nude mice received a subcutaneous injection of buprenorphine SR ~30 mins prior to surgery. They were anesthetized with isoflurane. The method of Iwami and co-workers1 involving intracerebral tumor cell injection through the postglenoid foramen was used as before2. The injection solution (2 μl) consisted of GBM cells (5×10$^4$) in Matrigel™ media (4:6) Animals were randomly assigned to two treated groups and one untreated control group of 9 each.

The following list of aspects reflects a variety of the embodiments explicitly contemplated by the present disclosure. Those of ordinary skill in the art will readily appreciate that the aspects below are neither limiting of the embodiments disclosed herein, nor exhaustive of all of the embodiments conceivable from the disclosure above, but are instead meant to be exemplary in nature.

1. A method for disrupting mitochondrial function in cells, the method comprising: causing, by controlling hardware, one or more magnets along (i) a first axis and a (ii) a second axis substantially orthogonal to the first axis, to oscillate so as to generate an oscillating magnetic field; and applying the oscillating magnetic field to a tissue comprising cells with a mitochondrial impairment to trigger apoptosis, or another mechanism of cell death, in the cells with the mitochondrial impairment.

2. The method of aspect 1, wherein causing the one or more magnets to oscillate further comprises causing the one or more magnets to oscillate along a third axis substantially orthogonal to the first axis and the second axis.

3. A method for inducing apoptosis, or another mechanism of cell death, in cancer cells, the method comprising: generating an oscillating magnetic field by controlling hardware; and applying the oscillating magnetic field to a tissue comprising cancer cells for inducing apoptosis or another mechanism of cell death in the cancer cells through the increased production of reactive oxygen species (ROS).

4. The method of any one of aspects 1-3, wherein applying the oscillating magnetic field to the tissue includes altering the electron flow in the tissue.

5. The method of aspect 4, wherein altering the electron flow in the tissue includes opening of mitochondrial membrane permeability transition pore and inducing rapid fluctuation or sustained depolarization of a mitochondrial membrane potential (MMP) in the tissue to cause fragmentation of mitochondrial networks in the tissue, wherein the altering of the electron flow causes apoptosis, or another mechanism of cell death, in cells with mitochondrial impairment and not in non-cancerous cells without mitochondrial impairment.

6. The method of aspect 4, wherein altering the electron flow in the tissue decreases glucose-derived 13C-acetyl-CoA synthesis in mitochondria of the tissue.

7. The method of aspect 4, wherein alteration of the electron flow in the tissue increases glycolytic flux in the tissue.

8. The method of aspect 2, wherein altering the electron flow in the tissue increases superoxide, peroxide and other reactive oxygen species generation.

9. The method of any one of aspects 1 to 8, wherein the cells with the mitochondrial impairment are cancer cells.

10. The method of aspect 9, wherein the cancer cells are glioblastoma (GBM) cells.

11. The method of aspect 9, wherein the cancer cells are non-small cell lung carcinoma, malignant meningioma, diffuse intrinsic pontine glioma, carcinoma of the breast, esophageal cancer and other cancer cells.

12. The method of any one of aspects 1 to 11, wherein the magnet is axially magnetized at 1.2 Tesla or more.

13. The method of any one of aspects 1 to 12, wherein the magnet is diametrically magnetized at 1.2 Tesla or more.

14. The method of any one of aspects 1 to 13, wherein the magnet is a rare earth permanent magnet.

15. The method of aspect 13, wherein the magnet is N52 neodymium.

16. The method of any one of aspects 1 to 15, wherein causing the magnet to oscillate includes oscillating the magnet using an electric motor with a motor shaft, wherein the magnet is mounted to the motor shaft.

17. The method of aspect 16, wherein causing the magnet to oscillate includes rotating the magnet at a rate of between 200 RPM and 24,000 RPM.

18. The method of aspect 16, wherein the magnet is mounted to the motor shaft either perpendicularly to the motor shaft, coaxially with the motor shaft, or longitudinally to the motor shaft.

19. The method of aspect 16, wherein causing the magnet to oscillate further includes causing the magnet to oscillate either perpendicularly to the motor shaft, coaxially with the motor shaft, or longitudinally to the motor shaft.

20. The method of any one of aspects 1 to 19, wherein applying the oscillating magnetic field to the tissue includes applying the oscillating magnetic field continuously during of a period of between 1 minute and 20 hours.

21. The method of any one of aspects 1-19, wherein applying the oscillating magnetic field to the tissue includes applying the oscillating magnetic field continuously during of a period of between about 20-30 hours.

22. The method of any one of aspects 1 to 21, wherein applying the oscillating magnetic field to the tissue includes applying a series of stimulus pulses of a first duration separated by inter-stimulus pulse intervals of a second duration, wherein the first duration is in a range of about 10 milliseconds to about 5 seconds, and the second duration is in a range of about 10 milliseconds to about 10 minutes.

23. The method of any one of aspects 1-22, wherein applying the oscillating magnetic field to the tissue includes generating a sequence of pulses with a pulse length of approximately 250 ms.

24. The method of aspect 22, wherein applying the series of stimulus pulses includes dynamically varying, during a treatment session, at least one of (i) the first duration, (ii) the second duration, or (iii) a rate at which the magnet oscillates.

25. The method of any one of aspects 1 to 24, wherein applying the oscillating magnetic field to the tissue includes operating a stimulator including the magnet in one of (i) a wearable helmet, (ii) a brace, or (iii) a belt.

26. The method of any one of aspects 1 to 25, wherein applying the oscillating magnetic field to the tissue includes operating a stimulator including the magnet in a bridge frame straddling a body part.

27. The method of any one of aspects 1 to 26, wherein the magnet is integrated into an end of an intraoperative probe.

28. The method of any one of aspects 1 to 27, wherein the magnet is a first magnet included in a plurality of magnets, the method further comprising: causing, by the controlling hardware, the plurality of magnets to oscillate to generate respective components of the oscillating magnetic field.

29. The method of aspect 28, wherein each pair in the plurality of magnets is separated by at least 2 cm at respective magnetic ends.

30. The method of aspect 29 or aspect 30, wherein the plurality of magnets includes a pair of magnets oriented at an angle of at least 60 degrees relative to each other.

31. The method of any one of aspects 29 to 30, wherein applying the oscillating magnetic field to the tissue includes placing the plurality of magnets around the tissue.

32. The method of any one of aspects 29 to 31, wherein generate respective components of the oscillating magnetic field includes varying at least one of (i) a rate of oscillation, (ii) a time of activation, (iii) a duration of stimulus pulses, or (iv) a duration of inter-stimulus pulse intervals for a certain magnet in the plurality of magnets independently of at least one other magnet in the plurality of magnets.

33. The method of any one of aspects 29 to 32, wherein applying the oscillating magnetic field to the tissue includes: causing individual magnets in the plurality of magnets to oscillate in accordance with a programmed protocol specific to a patient.

34. The method of any one of aspects 1 to 33, further comprising: introducing a chemical into the tissue comprising cells with the mitochondrial impairment.

35. The method of aspect 34, wherein the chemical is a ketone body, or a free fatty acid.

36. The method of aspect 35, wherein the ketone body is a β-hydroxybutyrate.

37. The method of aspect 35, wherein the ketone body is acetoacetate.

38. The method of aspect 35, wherein the free fatty acid is octanoate, stearic acid or palmitate.

39. The method of aspect 34, wherein the chemical is a branched chain amino acid.

40. The method of aspect 39, wherein the branched chain amino acid is leucine, isoleucine or valine.

41. The method of aspect 34, wherein the chemical is a cryptochrome agonist.

42. The method of aspect 41, wherein the cryptochrome agonist is KL001.

43. The method of aspect 34, wherein the chemical is an O(6)-Methylguanine-DNA methyltransferase (MGMT) inhibitor.

44. The method of any one of aspects 34-43, further comprising introducing a DNA alkylating agent to the subject.

45. The method of any one of aspects 35-43, further comprising introducing a DNA methylating agent to the subject.

46. A method for oncomagnetic treatment of tumor, the method comprising:
introducing a chemical into a tissue comprising the tumor;
generating, by controlling hardware, an electromagnetic signal parameterized to treat the tumor by (i) preventing cell division or growth, and/or (ii) causing cell death; and
applying the electromagnetic signal to the tissue to alter electron flow in the tissue, wherein the chemical potentiates the treatment of the tumor.

47. The method of aspect 46, wherein the oscillating magnetic field and chemical are administered concurrently.

48. The method of aspect 46, wherein the oscillating magnetic field and chemical are administered at separate times or consecutively.

49. The method of aspect 48, wherein the oscillating magnetic field is applied prior to administering the chemical.

50. The method of aspect 48, wherein chemical is administered prior to applying the oscillating magnetic field.

51. The method of aspect 46, wherein the chemical is a ketone body.

52. The method of aspect 51, wherein the ketone body is a β-hydroxybutyrate.

53. The method of aspect 51, wherein the ketone body is acetoacetate.

54. The method of aspect 46, wherein the chemical is a free fatty acid.

55. The method of aspect 54, wherein the free fatty acid is an octanoate.

56. The method of aspect 54, wherein the free fatty acid is a palmitate.

57. The method of aspect 46, wherein the chemical is a branched chain amino acid.

58. The method of aspect 57, wherein the branched chain amino acid is leucine, isoleucine or valine.

59. The method of aspect 46, wherein the chemical is a cryptochrome agonist.

60. The method of aspect 59, wherein the cryptochrome agonist is KL001.

61. The method of aspect 46, wherein the chemical is an O(6)-Methylguanine-DNA methyltransferase (MGMT) inhibitor.

62. The method of aspects 46-61, further comprising introducing a DNA alkylating agent to the subject.

63. The method of aspects 46-61, further comprising introducing a DNA methylating agent to the subject.

64. A system for disrupting mitochondrial function in cells, the system comprising: at least one stimulator including a magnet; and a controlling hardware configured to cause the magnet to oscillate so as to generate an oscillating magnetic field that, when applied to a tissue comprising cells with a mitochondrial impairment, triggers apoptosis, or another mechanism of cell death, in the cells with the mitochondrial impairment.

65. The system of aspect 64, wherein the magnet is axially magnetized at 1.2 Tesla or more.

66. The system of aspect 64 or aspect 65, wherein the magnet is diametrically magnetized at 1.2 Tesla or more.

67. The system of any one of aspects 64 to 66, wherein the magnet is a rare earth permanent magnet.

68. The system of any one of aspects 64 to 67, wherein the magnet is N52 neodymium.

69. The system of any one of aspects 64 to 68, wherein the stimulator includes an electric motor with a motor shaft, wherein the magnet is mounted to the motor shaft.

70. The system of any aspect to 69, wherein the controlling hardware causes the magnet to oscillate includes rotating the magnet at a rate of between 200 RPM and 24,000 RPM.

71. The system of aspect 69 or aspect 70, the magnet is mounted to the motor shaft either perpendicularly to the motor shaft, coaxially with the motor shaft, or longitudinally to the motor shaft.

72. The system of any one of aspects 69 to 71, wherein the controlling hardware causes the magnet to oscillate either perpendicularly to the motor shaft, coaxially with the motor shaft, or longitudinally to the motor shaft.

73. The system of any one of aspects 64 to 72, wherein the controlling hardware is configured to apply the oscillating magnetic field to the tissue continuously during of a period of between 1 minute and 18 hours.

74. The system of any one of aspects 64 to 73, wherein the controlling hardware is configure to generate a series of stimulus pulses of a first duration separated by inter-stimulus pulse intervals of a second duration, wherein the first duration is in a range of about 10 milliseconds to about 5 seconds, and the second duration is in a range of about 10 milliseconds to about 10 minutes.

75. The system of any one of aspects 64 to 74, wherein the controlling hardware is configured to dynamically vary during a treatment session, at least one of (i) the first duration, (ii) the second duration, or (iii) a rate at which the magnet oscillates.

76. The system of any one of aspects 64 to 75, further comprising: a plurality of stimulators including the at least one stimulator, each stimulator including a respective magnet; wherein the controlling hardware is configured to activate the plurality of stimulators according to a stimulation pattern.

77. The system of aspect 76, wherein the plurality of stimulators are mounted in one of (i) a wearable helmet, (ii) a brace, or (iii) a belt.

78. The system of aspect 76 or aspect 77, wherein each pair in the plurality of magnets is separated by at least 2 cm at respective magnetic ends.

79. The system of any one of aspects 76 to 78, wherein plurality of stimulators includes a pair of magnets oriented at an angle of at least 60 degrees relative to each other.

80. The system of any one of aspects 64 to 79, wherein the controlling hardware includes: one or more processors, and a non-transitory computer-readable medium storing software instructions that, when executed by the one or more processors, cause the controlling hardware to generate signals that cause the magnet to oscillate.

81. The system of aspect 80, further comprising: a peripheral interface via which the controlling hardware provides the signals to the magnet.

82. A method for disrupting mitochondrial function in cells, the method comprising: introducing a ketone body into a tissue comprising cells with a mitochondrial impairment; generating, by controlling hardware, an alteration of electron flow parameterized to treat the tumor by at least one of (i) preventing cell division or growth, or (ii) causing cell death; and applying an oscillating magnetic field to the tissue, wherein the chemical potentiates the treatment of the tumor.

83. The method of aspect 82, wherein the ketone body is a β-hydroxybutyrate or acetoacetate.

84. The method of aspect 82 or 83, wherein alteration of electron flow in the tissue includes altering the electron flow using an oscillating magnetic field.

85. The method of aspect 84, wherein alteration of electron flow using the oscillating magnetic field includes causing, by the controlling hardware, a magnet to oscillate so as to generate the oscillating magnetic field.

86. The method of aspect 85, wherein alteration of electron flow in the tissue includes opening of the mitochondrial permeability transition pore and inducing rapid fluctuation or sustained depolarization of a mitochondrial membrane potential (MMP) in the tissue to cause fragmentation of mitochondrial networks in the tissue, wherein the inducing rapid fluctuation or sustained depolarization of the MMP causes apoptosis, or another mechanism of cell death, in the cells with the mitochondrial impairment and not in non-cancerous cells without mitochondrial impairment.

87. The method of aspect 83 to 85, wherein alteration of electron flow in the tissue decreases glucose-derived 13C-acetyl-CoA synthesis in mitochondria of the tissue.

88. The method of aspect 85, wherein alteration of electron flow in the tissue increases glycolytic flux in the tissue.

89. The method of aspect 85, wherein alteration of electron flow in the tissue increases superoxide, peroxide and other reactive oxygen species generation.

90. The method of any one of aspects 82 to 89, wherein the cells with the mitochondrial impairment are cancer cells.

91. The method of aspect 90, wherein the cancer cells are glioblastoma (GBM) cells.

92. The method of aspect 90, wherein the cancer cells are non-small cell lung carcinoma, malignant meningioma, diffuse intrinsic pontine glioma, carcinoma of the breast and other cancer cells.

93. The method of any one of aspects 82 to 92, wherein the magnet is axially magnetized at 1.2 Tesla or more.

94. The method of any one of aspects 82 to 92, wherein the magnet is diametrically magnetized at 1.2 Tesla or more.

95. The method of any one of aspects 82 to 94, wherein the magnet is a rare earth permanent magnet.

96. The method of aspect 95, wherein the magnet is N52 neodymium.

97. The method of any one of aspects 82 to 96, wherein causing the magnet to oscillate includes oscillating the magnet using an electric motor with a motor shaft, wherein the magnet is mounted to the motor shaft.

98. The method of any one of aspects 82 to 97, wherein causing the magnet to oscillate includes rotating the magnet at a rate of between 200 RPM and 24,000 RPM.

99. The method of aspect 97, wherein the magnet is mounted to the motor shaft either perpendicularly to the motor shaft, coaxially with the motor shaft, or longitudinally to the motor shaft.

100. The method of aspect 95 or aspect 99, wherein causing the magnet to oscillate includes causing the magnet to oscillate either perpendicularly to the motor shaft, coaxially with the motor shaft, or longitudinally to the motor shaft.

101. The method of any one of aspects 82 to 100, wherein applying the oscillating magnetic field to the tissue includes applying the oscillating magnetic field continuously during of a period of between 1 minute and 20 hours.

102. The method of any one of aspects 82 to 100, wherein applying the oscillating magnetic field to the tissue includes applying a series of stimulus pulses of a first duration separated by inter-stimulus pulse intervals of a second duration, wherein the first duration is in a range of about 10 milliseconds to about 5 seconds, and the second duration is in a range of about 10 milliseconds to about 10 minutes.

103. The method of aspect 102, wherein applying the series of stimulus pulses includes dynamically varying, during a treatment session, at least one of (i) the first duration, (ii) the second duration, or (iii) a rate at which the magnet oscillates.

104. The method of any one of aspects 82 to 103, wherein applying the oscillating magnetic field to the tissue includes operating a stimulator including the magnet in one of (i) a wearable helmet, (ii) a brace, or (iii) a belt.

105. The method of any one of aspects 82 to 104, wherein applying the oscillating magnetic field to the tissue includes operating a stimulator including the magnet in a bridge frame straddling a body part.

106. The method of any one of aspects 82 to 104, wherein the magnet is integrated into an end of an intraoperative probe.

107. The method of any one of aspects 82 to 106, wherein the magnet is a first magnet included in a plurality of magnets, the method further comprising: causing, by the controlling hardware, the plurality of magnets to oscillate to generate respective components of the oscillating magnetic field.

108. The method of aspect 107, wherein each pair in the plurality of magnets is separated by at least 2 cm at respective magnetic ends.

109. The method of aspect 107 or aspect 108, wherein the plurality of magnets includes a pair of magnets oriented at an angle of at least 60 degrees relative to each other 110. The method of any one of aspects 107 to 109, wherein applying the oscillating magnetic field to the tissue includes placing the plurality of magnets around the tissue.

111. The method of any one of aspects 107 to 110, wherein generate respective components of the oscillating magnetic field includes varying at least one of (i) a rate of oscillation, (ii) a time of activation, (iii) a duration of stimulus pulses, or (iv) a duration of inter-stimulus pulse intervals for a certain magnet in the plurality of magnets independently of at least one other magnet in the plurality of magnets.

112. The method of any one of aspects 107 to 111, wherein applying the oscillating magnetic field to the tissue includes: causing individual magnets in the plurality of magnets to oscillate in accordance with a programmed protocol specific to a patient.

113. The method of any one of aspects 82 to 112, wherein applying the oscillating magnetic field to the tissue comprises applying an oscillating magnetic field configured to trigger apoptosis, or another mechanism of cell death, in the cells with the mitochondrial impairment.

114. A device for providing an oscillating magnetic field (OMF) treatment to a patient, the device comprising a plurality of ribs configured to articulate relative to a frame so as to fit around a head of a patient; and a plurality of inserts, each configured to attach to at least one of the plurality of ribs and support one or more magnetic stimulators to generate an oscillating magnetic field for application to the head of the patient.

115. The device of aspect 114, wherein the plurality of ribs is in an antero-posterior orientation relative to the head.

116. The device of aspect 114, wherein the plurality of ribs is connected to the frame by respective ball joints.

117. The device of aspect 114, wherein the plurality of ribs is configured to be angularly fixed relative to the frame using a locking mechanism.

118. The device of aspect 114, wherein the frame is a ring.

119. The device of aspect 114, wherein the plurality of ribs is made of aluminum.

120. The device of aspect 114, wherein the plurality of ribs is made of non-magnetic material.

121. The device of aspect 114, wherein the plurality of inserts is made of plastic.

The invention claimed is:

1. A method for disrupting mitochondrial function in cells, the method comprising:
   causing, by controlling hardware, one or more magnets along (i) a first axis and a (ii) a second axis substantially orthogonal to the first axis, to oscillate so as to generate an oscillating magnetic field (OMF);
   generating a sequence of pulses including multiple pulse train with (i) a duration of each pulse train being between 250 ms and 500 ms, and (ii) an inter-pulse train interval being between 250 ms and 2,000 ms including ramping a frequency of the OMF to a peak frequency over a period of 75 ms to 100 ms; and
   applying the oscillating magnetic field to a tissue comprising cells with a mitochondrial impairment to trigger cell death in the cells with the mitochondrial impairment.

2. The method of claim 1, wherein causing the one or more magnets to oscillate further comprises causing the one or more magnets to oscillate along a third axis substantially orthogonal to the first axis and the second axis.

3. The method of claim 1, wherein the peak frequency is between 100 and 350 Hz.

4. The method of claim 1, wherein applying the oscillating magnetic field includes generating a peak to peak amplitude of 3 mT for the OMF.

5. The method of claim 1, wherein applying the oscillating magnetic field includes generating, in the tissue, a magnetic field strength of 1 to 200 mT.

6. The method of claim 1, wherein causing the one or more magnets to oscillate includes communicating rotation to at least one permanent magnet.

7. The method of claim 6, wherein communicating rotation to at least one permanent magnet includes rotating the magnet at a rate of between 200 RPM and 24,000 RPM.

8. The method of claim 1, wherein causing the one or more magnets to oscillate includes communicating translation oscillation to at least one permanent magnet.

9. The method of claim 1, wherein each of the one or more magnets is axially magnetized at at least 1.2 Tesla.

10. The method of claim 1, wherein each of the one or more magnets is diametrically magnetized at at least 1.2 Tesla.

11. The method of claim 1, wherein applying the oscillating magnetic field to the tissue includes inducing an alteration of electron flow in the tissue.

12. The method of claim 11, wherein inducing the alteration of electron flow in the tissue includes loss of mitochondrial integrity and/or opening of mitochondrial membrane permeability transition pores and/or inducing rapid fluctuation or sustained depolarization of a mitochondrial membrane potential (MMP) in the tissue to cause fragmentation of mitochondrial networks in the tissue, wherein inducing the alteration of the electron flow causes cell death in cells with mitochondrial impairment and not in non-cancerous cells without mitochondrial impairment.

13. The method of claim 1, wherein each of the one or more magnets is a rare earth permanent magnet.

14. The method of claim 1, further comprising:
   introducing a chemical into the tissue comprising cells with the mitochondrial impairment.

15. The method of claim 14, wherein the chemical is a ketone body, or a free fatty acid.

16. A device comprising:
   a first magnetic assembly configured to rotate a first diametrically magnetized magnet around a first axis;
   a second magnetic assembly configured to rotate a second diametrically magnetized magnet around a second axis substantially orthogonal to the first axis;
   a controlling hardware configured to operate the first magnetic assembly and the second magnetic assembly so as to generate an oscillating magnetic field (OMF), including:
      generate a sequence of pulses including multiple pulse train with (i) a duration of each pulse train being between 250 ms and 500 ms, and (ii) an inter-pulse train interval being between 250 ms and 2,000 ms including ramping a frequency of the OMF to a peak frequency over a period of 75 ms to 100 ms, and
      apply the oscillating magnetic field to a tissue comprising cells with a mitochondrial impairment to trigger cell death in the cells with the mitochondrial impairment.

17. The device of claim 16, further comprising:
   a third magnetic assembly configured to rotate a third diametrically magnetized magnet around a third axis orthogonal to the first axis and the second axis.

18. The device of claim 16, wherein the peak frequency is between 100 and 350 Hz.

19. The device of claim 16 configured to generate a peak to peak amplitude of 3 mT for the OMF.

20. The device of claim 16 configured to generate in the tissue, a magnetic field strength of 1 to 200 mT.

* * * * *